United States Patent [19]
Goodfellow

[11] Patent Number: 6,015,670
[45] Date of Patent: Jan. 18, 2000

[54] METHODS FOR IDENTIFYING A MUTATION IN A GENE OF INTEREST WITHOUT A PHENOTYPIC GUIDE USING ES CELLS

[75] Inventor: Peter N. Goodfellow, Belsize Park, United Kingdom

[73] Assignee: Hexagen Technology Limited, Cambridge, United Kingdom

[21] Appl. No.: 08/970,740

[22] Filed: Nov. 14, 1997

Related U.S. Application Data

[63] Continuation-in-part of application No. 08/857,946, May 16, 1997.
[60] Provisional application No. 60/017,824, May 17, 1996.

[51] Int. Cl.[7] .............................. C12Q 1/68; C12P 19/34
[52] U.S. Cl. ............................................. 435/6; 435/91.2
[58] Field of Search ........................................ 435/6, 91.2

[56] References Cited

U.S. PATENT DOCUMENTS

| | | | |
|---|---|---|---|
| 5,045,450 | 9/1991 | Thilly et al. | 435/6 |
| 5,190,856 | 3/1993 | Borresen | 435/6 |
| 5,347,075 | 9/1994 | Sorge | 800/2 |
| 5,364,783 | 11/1994 | Ruley et al. | 435/235.1 |
| 5,429,923 | 7/1995 | Seidman et al. | 435/6 |
| 5,650,550 | 7/1997 | Korach et al. | 800/2 |
| 5,780,236 | 7/1998 | Dove et al. | 435/6 |

OTHER PUBLICATIONS

Kaneko et al., Laboratory Animals 29(4), 442–446 (Oct. 1995).
Gordon et al., Mutation Research 243, 145–149 (1990).
Bode et al., 1988, hph–1: a mouse mutant with hereditary hyperphenylalaninemia induced by ethylnitorsourea mutagenesis, *Genetics*, 118: 299–305.
Casadaban and Cohen, 1979, Lactose genes fused to exogenous promoters in one step using a Mu–lac bacteriophage: In vivo probe for transcriptional control sequences, *Proc. Natl. Acad. Sci. U.S.A.*, 76: 4530–4533.
Chiocca et al., 1992, Genotypic analysis of N–ethyl–N–nitrosourea–induced mutations by Taq I restriction fragment length polymorphism/polymerase chain reaction in the c–H–ras 1 gene, *Proc. Natl. Acad. Sci. U.S.A.*, 89: 5331–5335.
Colledge et al., 1995, Generation and characterization of a delta F508 cystic fibrosis mouse model, *Nature Genetics*, 10: 445–452.
Ellison et al., 1993, Efficacy of fluorescence–based PCR–SSCP for detection of point mutations, *Biotechniques*, 15: 684–691.
Faham and Cox, 1995, A novel in vivo method to detect DNA sequence variation, *Genome Res.*, 5: 474–482.
Favor, 1986, The frequency of dominanat cataract and recessive specific–locus mutations in mice derived from 80 or 160 mg ethylnitrosourea per kg body weight treated spermatogonia, *Mutat. Res.*, 162(1): 69–80.

Glavac and Dean, 1993, Optimization of the single–strand conformation polymorphism (SSCP) technique for detection of point mutations, *Hum. Mutat.*, 2: 404–414.
Harding et al., 1992, Sar: A genetic mouse model for human sarcosinemia generated by ethylnitrosourea mutagenesis, *Proc. Natl. Acad. Sci. U.S.A.*, 89: 2644–2648.
Johnson and Lewis, 1981, Electrophoretically detected germinal mutations induced in the mouse by ethylnitrosourea, *Proc. Natl. Acad. Sci. U.S.A.*, 78(5): 3138–3141.
Khrapko et al., 1994, Constant denaturan capillary electrophoresis (CDCE): a high resolution approach to mutational analysis, *Nucleic Acids Res.*23(3): 364–369.
Lewis et al., 1985, A mutation in the β–globin gene detected in the progeny of a female mouse treated with ethylnitrosourea, *Proc. Natl. Acad. Sci. U.S.A.*, 82(17): 5829–5831.
McWhir et al., 1993, Mice with DNA repair gene (ERCC–1) deficiency have elevated levels of p53, liver nuclear abnormalities and die before weaning, *Nature Genetics*, 5: 217–224.
Palombo et al., 1992, Non–phenotypic selection of N–methyl–N–nitrosourea–induced mutations in human cells, *Nucleic Acids Res.*, 20: 1349–1354.
Rossant et al., 1992, Of fin and fur: mutational analysis of vertebrate embryonic development, *Genes Dev.*, 6: 1–13.
Russell et al., 1979, Specific–locus test shows ethylnitrosourea to be the most potent mutagen in the mouse, *Proc. Natl. Acad. Sci. U.S.A*, 76: 5818–5819.
Russell et al., 1982, Dose–response curve for ethylnitrosourea–induced specific–locus mutations in mouse spermatogonia, *Proc. Natl. Acad. Sci. U.S.A.*, 79: 3589–3591.
Russell et al., 1989, Chlorambucil effectively induces deletion mutations in mouse germ cells, *Proc. Natl. Acad. Sci. U.S.A.*, 86: 3704–3708.
Sadlack et al., 1993, Ulcerative colitis–like disease in mice with a disrupted interleukin–2 gene, *Cell*, 75: 253–261.
Sheffield et al., 1993, The sensitivity of single–strand conformation polymorphism analysis for hte detection of single base substitution, *Genomics*, 16: 325–332.
Solnica–Krezel et al., 1994, Efficient recovery of ENU–induced mutations from the zebrafish germline, *Genetics*, 136: 1401–1420.
Stevanovic et al., 1994, The cDNA sequence and chromosomal location of the human SOX2 gene, *Mammalian Genome*, 5: 640–642.
Yuan et al., 1995, Developmental–specific activity of the FGF–4 enhancer requires the synergistic action of Sox2 and Oct–3, *Genes Dev.*, 9: 2635–2645.

*Primary Examiner*—Kenneth R. Horlick

[57] ABSTRACT

The invention encompasses methods of identifying a mutation in a gene of interest in an organism which include identifying in a test DNA sample from a mutated organism or a mutated cell from an organism a mutation in a gene of interest without the prior observation of a phenotypic alteration in the mutated organism or cell.

4 Claims, 2 Drawing Sheets

METHODS FOR IDENTIFYING A MUTATION IN A GENE OF INTEREST WITHOUT A PHENOTYPIC GUIDE USING ES CELLS

This is a continuation-in-part of application Ser. No. 08/857,946, filed May 16, 1997, which claims the benefit of U.S. Provisional Application No. 60/017,824, filed May 17, 1996.

FIELD OF THE INVENTION

The invention relates in general to animal models for identification and characterization of a mutation in a gene of interest.

BACKGROUND OF THE INVENTION

Detection of non-naturally occurring nucleotide sequence mutations has been approached by performing studies on cells in culture or on live animals based on alterations in phenotype. Tests on cells in culture using bacterial or animal cells or cell lines permits the rapid screening of a large number of cells for the appearance of an altered phenotype. The appearance of an altered phenotypic trait reflects the occurrence of a mutation in the test gene.

Previous attempts to identify genetic mutations have involved genetic mutation analysis based on phenotypic screening (Russell et al., 1979, *Proc. Natl. Acad. Sci. U.S.A.* 76: 5818; Russell et al., 1982, *Proc. Natl. Acad. Sci. U.S.A.* 79: 3589). That is, a phenotypic abnormality, such as alteration from cwild-type (e.g. coat color in mice), is detected in the F1 offspring of a mutated animal, or in subsequent generations. Thus, Russell et al. assess mutation frequencies in a number of loci by identifying a mutant phenotype and correlating phenotype with a mutation at a corresponding locus. This is known as the 'specific-locus method' of calculating the frequency of mutations in a given locus. However, observation of a mutant phenotype does not directly identify the gene which is mutated, although for phenotypes known to be the result of mutation of a particular gene, it may be inferred and subsequently tested. Phenotypes of interest can serve as a guide to study particular genes, using conventional mapping and positional cloning techniques to identify a gene or genes relating to the phenotype. This approach relies on the occurrence of a phenotype which is used to score for a mutation, and the phenotype acts as a guide to the mutated gene.

Johnson et al., (1981, *Proc. Natl. Acad. Sci. U.S.A.* 82:5829) and Lewis et al., (1985, *Proc. Natl. Acad. Sci. U.S.A.* 82:5829) disclose a protein phenotype screen which detects electrophoretic mobility changes in proteins to test for induced genetic mutations. Protein extracts are isolated from a number of mutagenized animals, and specific proteins are assayed to look for abnormal electrophoretic migrations. This system identifies a change in phenotype in a protein in order to find a mutation in its corresponding gene.

The disadvantage of phenotypic screening for gene mutations is that the analysis of mutation distribution is always based on the window of observation that is permitted by the selective mutation system used, in which an alteration in a cell phenotype indicates that a mutation has occurred in a particular gene. The chief drawback of mutation assays involving phenotypic selection is that mutation analysis is confined to those genetic alterations which produce an altered gene product which is detectable via a phenotypic screen. Therefore, a phenotype must be matched with the mutation prior to detection or characterization of the mutant gene itself. For example, U.S. Pat. No. 5,347,075 discloses mutagenesis testing using a transgenic animal carrying a lacZ reporter test gene, wherein either cells containing the test gene or the animal itself is mutated, the 'mutated' test gene is cloned in bacteria and then grown on X-gal indicator plates. Mutations in the reporter test gene are thus indicated phenotypically as white plaques rather than blue plaques.

Previous attempts to identify genetic mutations have also involved purely genotypic mutation analysis *in vitro*, or non-phenotypic selection of mutations (Palombo et al., 1992, *Nucleic Acids Res.* 20:1349; Chiocca et al., 1992, *Proc. Natl. Acad. Sci. U.S.A.* 78:3138). In these analyses, cells in culture are mutagenized, the DNA isolated, and tests are performed to detect mutations, for example, via changes in specific restriction endonuclease sites (RFLP analysis). Although this procedure tests DNA directly for induced mutations, it has been adapted solely for mutagenesis of cultured cells.

U.S. Pat. No. 5,045,450 discloses a method of determining a mutation spectrum in a DNA sequence of interest that is present in a population of cells. The method includes detecting spontaneous mutations in a DNA sample wherein DNA is extracted from the tissue to be analyzed, hybridized to form duplexes with nonmutated DNA, and subject to DNA gradient gel electrophoresis to detect single base changes.

Mutation detection can be divided into two categories: the detection of mutations in candidate disease genes; and the identification of mutations in known disease genes, each of which have different requirements. The detection of mutations in candidate disease genes has been based on the mapping of a particular phenotype to a particular chromosome region and the examination of all genes mapping to this region for mutations in order to identify the gene responsible for the disease.

Animal models of disease have been produced in the prior art via phenotypic observation of a mutated animal. See, for example, Harding et al., 1992, Proc. Nat. Aca. Sci. 89:2644, in which a mouse mutant with sarcosinemia was found by screening the progeny of ENU-mutagenized mice for aminoacidurias; and Bode et al, 1988, *Genetics* 118:299, in which ENU-mutagenesis was used to screen for defects in phenylalanine metabolism by detecting elevated serum levels of phenylalanine. Mouse models of disease have also been produced via targeted mutagenesis involving targeting of a specific gene in ES cells, production of a mouse from the mutated ES cells, and ascertainment of phenotype. In such targeted mutations, the mutated gene is typically a "knockout", i.e., in which a mutation is generated which fully or partially inactivates the gene. For example, see Sadlack et al., 1993, *Cell* 75:253, in which mice deficient for IL-2 were constructed; and Colledge et al., 1995, *Nat. Genet.* 10:445, in which mice were generated carrying a mutation in the cystic fibrosis gene.

One object of the invention is to provide mutational screening methods based on genomic and genetic techniques, rather than on phenotypic observation, to identify and characterize a mutation in a gene of interest.

Another object of the invention is to identify and charactertize genes via mutagenesis in order to identify genes encoding products which may have therapeutic benefit.

Another object of the invention to provide methods for identifying mutations in a gene of interest which do not rely solely upon prior matching of a gene with a disease.

Another object of the invention is to provide methods for identifying mutations in a gene of interest which do not rely upon prior matching of a phenotypic mutation to a gene.

There is a need in the art for a direct test for mutations in the DNA of animals without using a phenotypic guide.

SUMMARY OF THE INVENTION

The invention is based on a novel method of identifying induced mutations in any particular gene in the genome of an organism without observing the phenotypic effects of the mutation prior to identifying the mutation.

In one aspect, the invention encompasses a method of identifying a mutation in a gene of interest in an organism, comprising testing a DNA sample from a mutated organism for a mutation in a gene of interest without the prior observation of a phenotypic alteration in the mutated organism.

This method may further comprise prior to the testing step, the step of mutagenizing an organism so as to produce the mutated organism.

The invention also encompasses a method of identifying a mutation in a gene of interest in an organism, comprising the steps of (in the following order): mutagenizing an organism to produce a mutated organism, testing a DNA sample from a mutated organism for a mutation in a gene of interest without the prior observation of a phenotypic alteration in the mutated organism, and optionally subsequently observing the phenotype of an organism which has been identified as containing a mutation in the gene of interest.

In another aspect, the invention encompasses a method of identifying a mutation in a gene of interest in an organism, comprising the steps of (in order): mutagenizing a plurality of the same organism to produce mutated organisms; and testing a mixture of pooled DNA samples containing a plurality of DNA samples from a corresponding plurality of mutated organisms for a mutation in a gene of interest without the prior observation of a phenotypic alteration in the mutated organisms, and optionally observing the phenotype of the organism containing the mutated gene of interest.

As used herein, a "plurality" refers to a large number of organisms, e.g., 100, 1,000, 10,000 and even up to 100,000.

The mutated organism (i.e., the organism whose DNA is tested for a genetic mutation) may be the same as the organism which is mutagenized; alternatively, the mutated organism may be the offspring of the organism which is mutagenized, for example, the F1 generation of the organism which is mutagenized, or the F2 or a subsequent generation of the organism which is mutagenized. If, after a mutation is detected in an organism, it is desired to generate offspring from it, it is obviously preferable that the mutated organism be the offspring of a mutangenised organism. This ensures that the mutations carried throughout its somatic and germline cells correspond, such that any offspring from the mutated organism carry the same mutation as was detected.

Preferably, the testing step comprises hybridization of a DNA (or equally, RNA) probe to the sample or the mixture, the probe being unique to the gene of interest. Alternatively, the testing step comprises hybridization of a mixture of multiple DNA probes to the sample or the mixture, the multiple DNA probes differing in sequence from each other and being unique to the gene of interest.

In another aspect, the invention encompasses a method of identifying a mutation in a gene of interest in an organism, comprising mutagenizing the germline DNA of an organism; mating the mutagenized organism to produce F1 offspring; and testing a DNA sample from an F1 offspring for a mutation in the gene of interest without the prior observation of a phenotypic alteration in the F1 offspring.

In this method, the geniline DNA may be from a female or male organism, but is preferably from a male organism.

In another aspect, the invention encompasses a method of identifying a mutation in a gene of interest of an organism, the method comprising the steps of a) providing a mixture of pooled DNA samples, each DNA sample of the pool being from a mutated organism; b) providing a nucleic acid probe unique to a gene of interest; c) testing the mixture for a mutation in the gene of interest by hybridizing the probe to the mixture without the prior observation of a phenotypic alteration in each the mutated organism.

The method may further comprise the steps of d) detecting a mutation in the mixture; and e) testing each DNA sample individually for a mutation in the gene of interest.

The method also may further comprise prior to step a), the step of mutagenizing a plurality of organisms.

In any of the above-described inventive steps each mutated organism has been mutagenized such that about 1 mutation occurs in every 10,000–1,000 genes.

In another aspect, the invention encompasses a method of identifying a mutation in two or more genes of interest in an organism, the method comprising the steps of a) providing a DNA sample from a given tissue of a mutated organism, wherein the mutated organism contains about 1 mutation in 1000 genes; b) providing plural nucleic acid probes, each probe being unique to a given gene of interest; and c) testing the DNA sample for a mutation in a gene of interest.

The method also may comprise prior to step a) the step of mutagenizing an organism to produce the mutated organism.

Preferably, the mutagenizing step in any of the above-described methods comprises inducing a genetic mutation into a gene of interest in an organism at an average frequency of 1/500, preferably 1/1000,–1/10,000 organisms.

Preferably, the mutation in any of the above-described methods is a single base pair mutation or a short insertion or deletion mutation, for example, in the range of about 1–10 base pairs.

One preferred method of mutagenesis according to the invention comprises exposing the organism to an alkylating agent, such as ENU or MNU.

One preferred method of mutagenesis according to the invention involves mutating germline DNA of the organism.

It is preferred according to the invention that the probe or probes comprises a pair of unique PCR primers, and that the testing for a mutation in the gene of interest comprises amplification of a segment of the gene of interest and sequencing of the amplified segment.

One preferred method of testing for a mutation in the gene of interest is fSSCP analysis.

As used herein, "organism" refers to a multicellular organism that undergoes development from an embryonic stage to an adult stage. The term "organism" may include insects, as well as vertebrates and invertebrates, the latter two categories of which fall within the term "animal". The invention is useful with respect to animals such as a nematode, a fish, such as a zebrafish, or a mammal, e.g., a rodent such as a mouse or a rat.

In another aspect, the inventive method comprises an improvement over previous methods of mutagenesis and testing for mutations. Therefore, in a method of inducing and identifying a mutation in a gene of interest in an organism, wherein the organism is exposed to a mutagen so as to induce a mutation in the genome of the organism, and the organism is then mated to produce an offspring containing the gene of interest, the improvement comprising the step of testing the gene of interest for a mutation without the prior selection of a phenotypic characteristic in the offspring.

Preferably, the improvement comprises testing the gene of interest for a mutation by hybridization of a DNA probe to a DNA sample of the offspring, the probe being unique to the gene of interest, or the improvement comprises testing the gene of interest for a mutation using a DNA probe which comprises a mixture of multiple DNA probes differing in sequence from each other and being unique to the gene of interest. Preferably, the DNA probe comprises a pair of unique PCR primers, and the testing step comprises amplification of a segment of the gene of interest and sequencing of the amplified segment. One preferred testing step comprises fSSCP analysis.

According to this aspect of the invention, in the method which is improved, the induced mutation is preferably a single base pair mutation or a short insertion or deletion mutation; and the mutagen comprises an alkylating agent, such as ENU or MNU.

It is preferred in the method which is improved, that the organism be exposed to a mutagen by mutating germline DNA of the organism.

In this aspect of the invention, a preferred animal which is mutated and whose DNA is tested for a mutation in a gene of interest is a mammal, such as a rodent, for example, a mouse.

The invention also encompasses a method of identifying a mutation in a gene of interest in a tissue, comprising mutagenizing an ES cell to produce a mutated ES cell; and testing DNA from the mutated ES cell for a mutation in the gene of interest without the prior observation of a phenotypic alteration in the mutated ES cell.

As used herein, the term "ES" cell refers to an embryonic stem cell.

The invention also encompasses a method of identifying a mutation in a gene of interest in a tissue, comprising mutagenizing plural ES cells to produce a plurality of mutated ES cells; and testing a DNA sample from each mutated ES cell or a DNA sample comprising DNA from a plurality of mutated ES cells for a mutation in the gene of interest without the prior observation of a phenotypic alteration in the mutated ES cell.

It is preferred that the steps of these methods be performed in their stated order.

Preferably, in these methods, the testing step includes PCR amplification and fSSCP analysis using a pair of PCR primers from a region of the gene of interest. Preferably, the methods also include the steps of transferring the mutated ES cell to a developing embryo of the same organism species from which the ES cell is derived; and permitting the embryo to develop into a newborn.

The inventive methods are particularly advantageous in that they permit direct testing of mutagenized DNA, and are thus independent of screening for a potential phenotype caused by mutations in the tested gene.

Methods of the invention provide a mutagenized organism containing a mutant gene which may be identified significantly more rapidly and at a lower cost than an analogous organism generated using for example transgenic technology.

Identification of an organism containing a mutant gene according to the invention permits the subsequent assessment of phenotypes resulting from the alteration of gene function, and provides a model organism to further disease diagnosis and drug development for both human and non-human diseases. A mutant gene identified according to the invention, or its wild-type counterpart, may encode a product which is useful as a therapeutic or as a target for a therapeutic.

The combination of organism mutagenesis and highly efficient mutation detection according to the invention permits the analysis of a range of different mutations in single genes, and enables analysis of classes of genes, such as gene families and genes known or suspected to be commonly involved in a developmental process or disease. This includes candidate genes identified through positional cloning experiments.

The inventive screening methods confer significant advantages over prior art methods in that the inventive methods are significantly less expensive and significantly faster.

As used herein, "mutation" refers to an alteration in the nucleotide sequence of a given gene or regulatory sequence from the naturally occurring or normal nucleotide sequence. A mutation may be a single nucleotide alteration (deletion, insertion, substitution), or a deletion, insertion, or substitution of a number of nucleotides. The term "mutation" also includes chromosomal rearrangements.

"Induced mutation" refers to those mutations which are caused to occur by subjecting an organism, or cells of its germline, to a mutation inducing condition, whether the inducing agent be a chemical or other mutagen or a gene mutation which induces mutations in the genome. For example, an "induced mutation" according to the invention may occur as a result of the use of a chemical mutagen or radiation mutagenesis in the laboratory. In addition, an "induced mutation" according to the invention may occur as a result of a mutation in a housekeeping gene of an organism which gives rise to additional mutations in the genome; for example, a mutation in a gene which encodes a DNA repair enzyme gives rise to numerous additional mutations in the genome of the organism. Induced mutations thus encompass non-naturally occurring mutations and do not encompass spontaneous mutations, which are defined by their exceedingly low frequency of occurrence (<1/100,000).

"Phenotype" refers to the biological appearances, including chemical, structural, and behavioral attributes of an organism, such as an organism or tissue thereof, and excludes its genetic constitution. "Genotype" defines the genetic material that an organism inherits from its parents. The phenotype changes with time as the appearance of an organism changes, whereas the genotype remains relatively constant except for genetic changes known as mutations. Phenotypic information refers to both obvious changes in the visual appearance of an organism, e.g., coat color; and also to less obvious changes, such as in cellular growth of a tissue of an organism or a cultured cell line, e.g., the adaptive ability to grow in the presence of a particular toxic chemical, or alterations in the electrophoretic mobility of a protein.

Where mutational screening is performed on tissue from an organism that has been subjected to induced mutagenesis "without phenotypic information" or "without regard to phenotype" of the mutated organism, a genetic, genotypic, or gene analysis (i.e., all referring to analytical techniques based on nucleotide sequence or nucleic acid analysis) is performed prior to any optional observation of phenotype which is associated with the induced genetic mutation. That is, where a DNA sample is tested for a mutation in a gene of interest "without the prior observation of a phenotypic alteration" in the mutated organism, this means that, following mutagenesis of DNA, there is no testing, detection, or selection of an associated phenotype, i.e., observations as to changes in subcellular (other than changes in DNA sequence or modification), cellular or organism behavior, metabolism, etc.

The term "gene" refers to a segment of DNA which may be transcribed into RNA, and which may contain an open reading frame and encode a protein, and also includes the DNA regulatory elements which control expression of the transcribed region. Therefore, a mutation in a gene may occur within any region of the DNA which is transcribed into RNA, or outside of the open reading frame and within a region of DNA which regulates expression of the gene (i.e., within a regulatory element). In diploid organisms, a gene is composed of two alleles.

The above-described methods of the invention also may consist essentially of the described steps. Unless indicated otherwise, "consist essentially of" refers to a series of steps which include a step of testing or screening for a mutation in a gene of interest and which exclude a step in which observation of a mutant phenotype in an organism or tissue thereof is performed after mutagenesis of the organism or tissue but prior to testing for a mutation in the gene of interest.

Further features and advantages of the invention will become more fully apparent in the following description of the embodiments and drawings thereof, and from the claims.

DESCRIPTION

Figure 1:
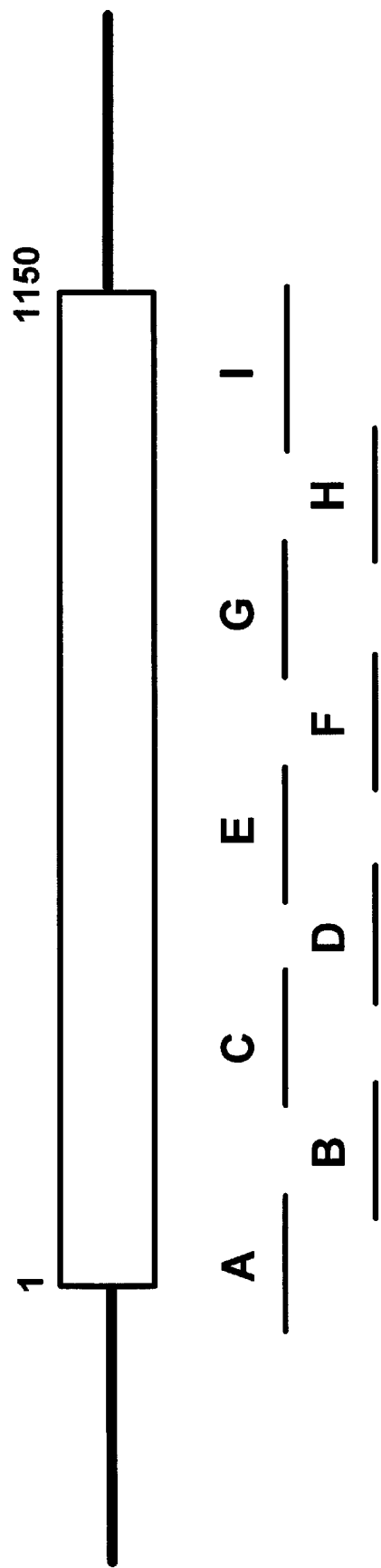
FIG. 1 is a diagram of the Sox3 gene showing the location of primers which are useful according to the invention for detection of mutations in the Sox3 gene.

The contents of references referred to herein are hereby incorporated by reference.

The current challenge in biology is in understanding the function of the 50–100,000 unique human genes in normal development and the role any given gene may play in disease. The identification of genes is proceeding rapidly, but ascribing function to any particular gene is slow. For example, the use of expressed sequence tags (ESTs) has rapidly provided over 30,000 unique gene sequences, very few of which have been characterized. For some of these gene sequences, similarity to a gene family of known function may provide evidence suggesting possible function, but determining a function for the gene is difficult and laborious. Another important advance has been the development of positional cloning to identify specific human genes involved in human disease. Genes identified by both sequence similarity and by positional cloning may potentially serve as therapeutic agents or targets for therapeutics if the gene function can be identified. In either case, it may be straightforward to deduce the primary sequence of the protein, but deducing a mode of action for the gene product is not straightforward. The biological role of proteins is best studied in vivo using animal models, as humans do not lend themselves well to these studies. A traditional route to ascribing function to a given gene has been to use phenotypic analysis of potential gene mutants to identify an aberrant phenotype and correlate the aberrant phenotype with a mutation in a gene or at a locus suspected to contain the gene.

The invention provides a first step in the analysis of gene function by permitting identification of a mutation in a gene of interest which may not have an ascribed function, but for which at least some nucleotide sequence information is known, i.e, at least enough to provide a unique probe for the gene. The invention thus provides a much preferred alternative to traditional genetic analysis of gene function, wherein gene mutations are induced and their existence identified initially via their phenotypic effects.

Non-human mammalian models, for example, a rodent such as the mouse, are preferred model organisms for the study of mammalian gene function and are commonly used as model systems for human disease. This is due to the similarity of the human and non-human mammalian developmental and biochemical pathways, (which is reflected in similarities in genes and genomic structure) and to the relative ease with which some mammals, such as mice, rats, hamsters, etc., can be housed and bred. Investigation of the mammalian equivalents of human genes allows determination of the spatial and temporal pattern of gene expression during critical developmental time points and in specific tissues, contributing to the understanding of protein function. However, it is by studying abnormal forms of the gene in vivo that the scope of the gene function can be assessed and therapeutic treatments can be developed. The most powerful tool for determining the biological function of a gene is the use of targeted mutagenesis, a procedure which has been developed for different organisms, ranging from invertebrates to vertebrates. This technology has been used to modify specific genes.

1. Prior attempts to modifying the mouse genome

Direct evidence for gene function has come from the observation of phenotypes conferred on individuals as the result of mutations in that gene. The phenotypic changes produced in the mutated organism can provide insight into the activity of a given gene. In some instances, gene modifications were made specifically to provide an animal model for human disease, e.g., for cystic fibrosis. In other cases, genes have been modified (usually inactivated) as a means to determine their function. In some cases, the modification may produce a phenotypic change which can be related to the human disease. For example, the Interleukin-2 gene produces a hormone which is thought to have a key role in the immune response of mammalian cells. The function of this gene was examined by deleting it through targeted mutagenesis in the mouse. Half of the mice died from immune system dysfunction, but all surviving mice develop an ulcerative colitis with striking clinical and histological similarity to inflammatory bowel disease in humans, providing evidence for a primary role of the immune system in ulcerative colitis and a new focus for the treatment of this disease in humans.

The invention provides advantages over the above-described prior art in that it provides methods of gene analysis which ultimately lead to a better understanding of the full range of activity and function of a gene for which a function may already be ascribed, such as those described above. The invention permits the identification of numerous mutations in a gene of interest and the generation of, for example, mutant organism gene homologs of a human gene of interest without relying on an aberrant phenotype to identify the presence of a mutation in the gene.

2. The Inventive Methods

The invention is based on the discovery that a gene of interest in an organism, that is any given gene of interest in an organism, may be tested for the presence of a mutation in the gene, without first observing the mutated organism with respect to a phenotypic effect of the mutation.

According to the invention, a mutation in a gene of interest is rapidly identified in a mutagenized organism via DNA analysis. In a preferred embodiment of the invention, mutations are chemically induced in the germline of an organism. Breeding of the mutagenized males to normal females results in offspring with one set of genes which is normal (from the mother) and one set of genes which has been exposed to the mutagen (from the father). Therefore, any mutations are heterozygous (present in only one of two copies of each gene) in the first generation (F1) organisms. As an alternative to breeding, nuclear transfer may be used according to the invention and Wilmut et al., 1997, Nature, 385: 810–813. A gene of interest is tested for mutations in a sufficient number of organisms to identify those with mutations in the gene. Thus, it is advantageous according to the invention to generate mutations in the organism's DNA at high frequency, and to perform mutational analysis on large numbers of organisms.

3. The inventive screening methods are significantly more powerful than conventional transgenic techniques.

Each mammalian gene has natural variants (alleles) within a population. Inheritance of unique combinations of alleles from each parent result in offspring with unique phenotypes. Some variants may cause, contribute or predispose to disease. Mutations in a gene which result in complete loss of function (a null allele) will often have a severe effect on phenotype. However the null allele is not the only disease causing modification. Other, more subtle changes to the genes may produce drastically different phenotypes, and different mutations in the same gene can cause different disease. For example, in humans, certain mutations of the WT1 gene can result in the development of kidney tumors, while other WT1 mutations result in the failure of male sexual development in chromosomal male individuals. Similarly, different mutations in the human FGFR2 gene cause the three distinct diseases; Pfieffer syndrome, Crouzon syndrome and Apert syndrome. It is more appropriate to consider genes as having a wide, if not continuous phenotypic potential depending on where the modification is found within the gene. Prior art methods of identifying a mutation in a gene of interest such as WT1 or FGFR2 in an organism require observation of a number of organisms for potentially vastly different phenotypes.

An advantage of the methods of the invention is that a typical screen of 10,000 organisms is expected to identify 5-15 independent and different protein altering mutations for each gene tested. No phenotypic screening is necessary to identify the mutations. The screen may also be performed on successive new organisms at a rate of 2000 per month until the appropriate type or number of mutations is identified. The ability to study an "allelic series" of mutations in a particular gene is crucial to the understanding of the full range of disease phenotypes associated with the gene. The organisms carrying these mutations may also be interbred providing a vast array of possible combinations, any of which may give insight into the disease state in humans.

4. The invention provides a complementary technique to positional cloning

Positional cloning relies on the ability to associate a region of the genome with a particular genetic disorder. Some gene research is based on the premise that disease genes can be mapped and cloned by identifying regions of the human genome that are associated with human disease phenotypes. This is done by collecting large numbers of phenotypically affected and control individuals and testing the entire genomes for regions which show linkage to the disease phenotype. The result of the analysis is the identification of a region of the genome which presumably contains genes contributing to the disease. This region is then searched for genes which become candidates based upon their position in the genome.

One of the major obstacles for positional cloning is in determining which of a number of candidate genes is the correct gene. The standard approach to assessing the candidate genes for their role in disease is to investigate the gene in individuals with the disease. Mutations in the gene that correlate with the presence of disease provide evidence for involvement of the gene in the disease. This analysis can be confounded by the presence of natural variation in the gene, or can be exceedingly complex where the disease is the result of complex interactions of genes such that any given individual will have mutation in a subset of all of the possible genes which can lead to the disease. Where more than one gene contributes to the disease phenotype, many of the patients will have a normal gene at that location and mutations elsewhere in the genome. In these cases the mutations may be more subtle variations that are difficult to detect rather than mutations that directly obviate gene function.

Methods of the invention have advantages which will alleviate these difficulties. Genes identified as candidates through positional cloning can be rapidly tested according to the invention by first identifying organisms with mutations in the candidate genes, and then subsequently testing these organisms for the disease phenotype. The invention therefore also provides methods for determining the function of a whole collection of candidate genes of unknown function. Where the mutated organism is an animal, mutant animals which are identified in this type of screen may then be interbred to produce animal models for complex polygenic diseases. The invention thus also provides animal models for diseases involving polygenic interactions.

METHODS OF THE INVENTION

It is contemplated according to the invention that large numbers of DNA samples, e.g., from a large number of different organisms, may be screened in a single procedure. For example, the invention contemplates high throughput screening of as many as 10,000–100,000 DNA samples. Where a large number of organisms is screened, the limits of such screening is found in the limits of production of a large number of organisms. Therefore, it is preferred that the choice of organism for mutagenesis and mutation detection be based on convenience of handling a given organism and the number of organisms which may be subjected to mutagenesis and screening, or, where the F1 generation of organisms is tested, the number of organisms which may be produced, e.g., by mating. It is also preferred that inbred organisms are used in mating, thereby ensuring that any differences in the DNA sequence of the offspring arises as a result of mutagenesis, and is not a natural polymorphism in the population.

Therefore, according to the invention, where a gene of interest is identified for mutation detection, for example a human gene of interest, an organism is chosen for mutagenesis, which is a good model for human disease, such as a mammal. Once the mammal is identified as being a good candidate for mutagenesis, a mutagenesis technique is selected according to the guidance provided below. After the animal is mutated, a body tissue is chosen ior DNA extraction and analysis of mutations in the gene of interest. Any one of a number of mutation detection techniques may be selected for identification of one or more mutations in the gene of interest.

Alternatively, where it is desired that fewer animals be subject to mutagenesis or where it is desired that more than one gene of interest be analyzed for mutations, the animals are mutagenized, DNA extracted from a selected tissue and subject to mutation detection using plural DNA probes for the gene of interest, each probe having a unique DNA sequence.

MUTAGENESIS ACCORDING TO THE INVENTION

The invention encompasses mutagenesis of whole organisms or of a selected tissue of an organism including but not limited to, for example, mutagenesis of germline cells of an organism, such as sperm stem cells or ova, or mutagenesis of embryonic stem (ES) cells of an organism, or introduction of a mutant gene into an organism which results in an increased frequency of mutations in the genome. Following mutagenesis of an organism, the organism may be analyzed directly for mutations, or it may be mated and the offspring analyzed for a mutation in a gene of interest. Obviously, it is preferred to analyze offspring in order to ensure that any mutation which is detected can be predictably passed on to further generations. Alternatively, following DNA analysis of a specific tissue for a mutation in a gene of interest, such as mutated ES clones in culture, the cells are transferred to the developing embryo. Mutagens and mutagenesis techniques which are applicable to organisms or cell mutagenesis are described below.

1. Types of DNA mutations.

Mutations in DNA may be (a) large lesion mutations, such as chromosomal breaks, rearrangements, and large insertions or deletions (on the order of kilobases); (b) small lesion mutations, such as cytogenetically visible deletions within a chromosome; and (c) small alterations, such as point mutations, insertions and small deletions (on the order of several-tens of bases). Any type of mutation may be analyzed according to the invention, although mutations which do not result in complete deletion of the gene of interest are preferred.

The invention is most useful for analyzing the latter category of mutations, i.e., point mutations, insertions and small deletions, and therefore it is preferred that the mutagenesis technique used to induce mutations according to the invention induce these types of mutations.

2. Selection of Mutagenesis Technique.

The selection of a mutagenesis technique useful according to the invention is dependent upon several factors. Some mutagens cause a wide spectrum of mutation types at a fixed condition(s). Some mutagens cause different types of mutations depending upon the mutagen dosage, mode of delivery, and the developmental stage at which the mutagen is administered to the organism. In addition, a mutagen may induce mutations at different frequencies depending upon the dosage regimen, mode of delivery, and the developmental stage of the organism or cell upon mutagen administration, all parameters of which are disclosed in the prior art for different mutagens or mutagenesis techniques. In addition, a defect in a gene which in wild-type form prevents mutations from occurring or repairs mutations may result in the failure to repair DNA mutations and thus provide a mutagenized genome for analysis according to the invention. Finally, the mutation rate from tissue to tissue will vary.

A mutagen or method of inducing mutations is considered useful according to the invention which provides the highest number of mutations per genome which does not kill the mutated organism.

Therefore, the following guidelines are important for selection of a mutagenesis technique or a mutagen for use according to the invention. First, the number of potentially mutant organisms which are generated for screening must be technically feasible. Second, the technique used to screen the generated organisms for mutations in a given gene or genes must be technically feasible. Third, the type of mutation induced in a gene of interest must leave the gene intact in the genome to the extent that it is detectable as described herein, with small deletions/insertions/substitutions, such as single base pair to several base pairs, being preferred. With these considerations in mind, it is possible to screen organisms which have been mutagenized at a high frequency or at a low frequency.

Those mutagens or mutagenesis techniques which result in mutations which occur within a gene, i.e., a region of DNA from which RNA is transcribed, or within the regulatory elements controlling expression of the gene are most useful according to the invention. Chemical mutagens which result in such mutations include but are not limited to mutagens which are alkylating agents which cause single nucleotide changes.

Therefore, according to the invention, mutations are induced in an organism at a high enough frequency such that the number of organisms needed to screen for a mutation in a gene of interest is not prohibitive. For example, it is particularly useful according to the invention to induce mutations at a high frequency in order to decrease the number of organisms screened. ENU mutagenesis is particularly useful according to the invention because, in the offspring of ENU mutagenized male mice, a mutation in any given gene will occur at a frequency of approximately 1 per 1000 mice. Thus, approximately 1000 mice are screened in order to detect a mutation in a particular gene. Although the ratio of 1/1000 has been calculated in the prior art based on phenotypic assays, it is the only way of assessing the relative mutational frequencies of mutagens or mutagenesis techniques useful according to the invention, as direct DNA analysis of the frequencies of mutations induced by a given mutagen or mutagenesis technique has not been performed. Because phenotypic mutation frequencies are based on DNA mutations which alter or destroy the function of a protein such that it causes a phenotypic change, the number of changes in the DNA of these mice in a given gene will be higher than 1/1000 due to "silent" mutations, i.e., which do not result in a phenotypic change. The same type of mutation frequency is obtained using other chemical mutagens, such as MNU, PRC, and MMS. Additional mutagens which may be considered equally useful according to the invention include chlorambucil and melphalan, and those listed below and in Table 1.

Although the mouse is specifically embodied herein as a representative organism that is useful according to the invention for inducing mutations and screening for mutations in a gene of interest, the invention is not limited to the use of mice. For example, other rodents such as a rat or hamster also provide representative animal models. However, the invention is not limited to mutagenesis and mutational analysis of a rodent. Non-rodent animals are equally appropriate, for example, organisms such as insects, nematodes, or fish, such as the zebrafish or medaka fish.

The zebrafish is a striped 2-inch long fish from the Ganges River. The zebrafish has been used as a genetic system and conditions for gamma-ray mutagenesis and screening are well-established (Chakrabarti et al., 1983, *Brachydonio Genetics* 103:109; Walker and Streisinger, 1983, *Genetics* 103:125). The advantages of zebrafish over the mouse for genetic analysis is its small size, the ability to house a large number of animals cheaply, and the large number of embryos produced from one female (usually a few hundred but as many as 1000 eggs). The time from fertilization to gastrulation is only about 5 hours at 28° C.; somites form between 10–20 hours; and by 24 hours postfertilization, a recognizable animal with rudimentary eyes and brain has formed. Thus, the early development of this vertebrate takes only about as long as a phage plaque assay. Rossant et al., 1992, *Genes Dev.* 6:1, describe mutational strategies for mutagenesis of zebrafish, including ENU mutagenesis.

Briefly, a three-generation cross in which F2 females, heterozygous for a number of induced mutations, are backcrossed to their father and mated to their brothers to reveal homozygous mutant phenotypes. A locus-specific mutation frequency of 1/1000 gametes scored is achievable in zebrafish using ENU mutagenesis. Therefore, one would need to screen at least 3,000 mutagenized gametes to approach saturation mutagenesis, and fewer than 2,000 gametes, i.e., on the order of about 1,000 gametes to perform mutational analysis according to the invention. ENU and EMS mutagenesis has been used to induce mutations in isolated sperm from zebrafish (Halpern et al., 1993, *Cell* 75:1; and Solnica-Knezel et al., 1994, *Genetics* 136:1401). The small teleost fish Medaka has also been subjected to ENU mutagenesis (Shiva et al., 1991, *Proc. Natl. Acad. Sci. U.S.A.* 88:2545), and also is encompassed within the invention. Zebrafish have been used in large-scale mutagenesis to search for genes controlling development in vertebrates (Mullins et al., 1994, *Curr. Biol.* 4:189).

In addition to mutagenized animals, lower organisms are useful according to the invention, such as mutagenized insects, e.g., Drosophila. EMS mutagenesis has been performed extensively on Drosophila melanogaster (Ashbumer, 1989, *Drosophila, A Laboratory Handbook*, Cold Spring Harbor Laboratory, Cold Spring Harbor, N.Y.; Grell et al., 1981, *Drosophila Environ. Mutagen.* 3:381; Ondrej, 1971, *Drosophila melanogaster Mut. Res.* 12:159). Non-insect primitive organisms such as the round worm, *Caenorhabditis elegans,* may also be used according to the invention. EMS has been used to mutagenize *C. Elegans* (Wood, 1988, *The Nematode C. Elegans*, Cold Spring Harbor Laboratory, Cold Spring harbor, N.Y.).

Non-mammalian organisms, such as fish, nematodes, and insects, are particularly useful according to the invention in identifying mutations in genes which are suspected to play a role in early development of the organism, e.g., in embryonic development, such as pattern-forming genes, limb-forming genes, or organ-forming genes.

From the above description, it is evident that, in order to be useful according to the invention, mutations also may be induced in an organism at a lower frequency (for example, where a mutagen is used having a lower mutation-induction frequency), provided a higher number of organisms or tissue samples from organisms are screened for a mutation in a gene of interest. The number of organisms tested is generally limited by the following: the number of mutant organisms that are generated, and the number of organisms that are screened. It may be possible to generate and screen a sufficient number of organisms to detect even an exceedingly low frequency of mutation, e.g., 1 mutation/50,000 organisms–1/75,000. Although screening for mutations which occur at a given frequency may be labor-intensive, a screening procedure must be employed which is feasible.

The invention therefore contemplates the use of any type of mutagenesis technique, including chemical mutagenesis, radiation mutagenesis, and to mutagenesis techniques which are based on molecular biology, such as introduction into an organism of a gene encoding a defective DNA repair enzyme, retroviral insertion mutagenesis and promoter- and gene-trapping mutagenesis, as described below.

The invention is particularly useful where the mutagenesis results in germline mutations, i.e., which are passed onto offspring which are tested for mutations, and therefore relates to mutations which are induced in the germline of a parent organism.

In a preferred aspect of the invention, a mutagenesis technique is employed which confers a mutation rate in the range of 1 mutation per 500 genes–1 mutation per 10,000 genes, or 1 mutation per gene per 100 organisms–1 mutation per gene per 10,000 organisms, optimally at least 1 mutation per 1000 genes, or 1 mutation per gene per 1000 organisms. It is desired according to the invention that the mutation frequency possess an upper limit that is below the frequency of inducing a dominant lethal mutation in every organism.

A) Chemical Mutagenesis and Mutagens.

Chemical mutagens are classifiable by chemical properties, e.g., alkylating agents, cross-linking agents, etc. The following chemical mutagens are useful according to the invention.

The following four mutagens are particularly useful for mutagenesis of male germ cells:

N-ethyl-N-nitrosourea (ENU)

N-methyl-N-nitrosourea (MNU)

procarbazine hydrochloride chlorambucil

Other chemical mutagens which are useful are as follows:

cyclophosphamide methyl methanesulfonate (MMS)

ethyl methanesulfonate (EMS)

diethyl sulfate acrylamide monomer triethylene melamin (TEM)

melphalan nitrogen mustard vincristine dimethylnitrosamine

N-methyl-N'-nitro-Nitrosoguanidine (MNNG)

7,12 dimethylbenz(a)anthracene (DMBA)

ethylene oxide hexamethylphosphoramide bisulfan

TABLE 1

Specific-locus mutation rates induced by chemicals that are mutagenic in post-cell stages of spermatogenesis

| Chemical | Ref. | Period of maximum effect. days(4) | Exposure(2) mg/kg | mol × $10^{-5}$ | Induced mutation rate(1) per locus ×$10^{-5}$(5) | per mol | Lethal(3)/tested mutations |
|---|---|---|---|---|---|---|---|
| Cp | A | 1–14 | 120 | 46.0 | 24.3 | 0.5 | 3/5 |
| McMs | B | 5–12 | 40 | 36.3 | 24.0 | 0.7 | 10/14 |
| EtMs | B | 5–12 | 175 | 141.0 | 20.9 | 0.1 | 0/1 |
| $Et_2SO_4$ | C | 5–12 | 200 | 129.7 | 11.2 | 0.1 | 4/4 |
| AA | I | 8–14 | 250 | 351.6 | 18.2 | 0.1 | 1/2 |
| TEM | D | 8–21 | 0.2 | 0.1 | 33.9 | 346.2 | 7/8 |
| Chl | I | 15–21 | 10 | 3.3 | 127.3 | 38.7 | 1/4 |
| Prc | E,F | (8) | 600 | 232.8 | 21.6 | 0.1 | 1/4 |
| ENU | G | 32–38 | 50 | 42.7 | 10.6 | 0.2 | 0/5 |
| MNU | H | 36–42 | 75 | 72.7 | 90.2 | 1.2 | 0/17 |

Cp, cyclophosphamide; MeMS, methyl methanesulforate; EtMs, ethyl methanesulforate; $Et_2SO_4$, diethyl sulfate; AA, acrylamide monomer; TEM, triethylene melamine; Chl, chlorambucil; Prc, phocarbazine hydrochloride; ENU, N-ethyl-N-nitrosourea; MNU, N-methyl N-nitrosourea.
(1)Expressed per kg of body weight. When results for more than one exposure level of a chemical were available, we list the one that the investigator(s) found most suitable for generating mutation-rate data.
(2)Experimental minus historical control, 43/801, 406, for period of maximum response.
(3)Lethals excluded. For chlorambeuil, the number includes mutations for which there is genetic, cytogenetic, and/or molecular evidence for deletion.
(4)Postexposure.
(5)Number of mutations in sample is shown in parentheses.
(8)Experiment did not involve sequential matings.

References:
A. Ehling, U. H. & Neuhauser-Klaus, A. (1988) *Mutat. Res.* 199, 21–30.
B. Ehling, U. H. & Neuhauser-Klaus, A. (1984) in *Problems of Threshold in Chemical Mutagenesis*, eds. Tazima, Y., Kondo, & Kuroda, Y. (Environ, Mutagen. Soc. Jpn., Mishima, Japan), pp. 15–25.
C. Ehling, U. H. & Neuhauser-Klaus, A. (1979) *Mutat. Res.* 199, 191–198.
D. Cattanech, B. M. (1967) *Mutat. Res.* 4, 73–82.
E. Ehling, U. H. & Neuhauser-Klaus, A. (1979) *Mutat. Res.* 59, 245–256.
F. Kratochvilova, J., Pavor, J. & Neuhauser-Klaus, A. (1988) *Mutat. Res.*, 198, 295–301.
G. Russell, W. L. & Hunsicker, P. R. (1983) *Environ. Mutagen.* 5, 498 (abstr.).
H. Russell, W. L. & Hunsicker, P. R. (1984) *Environ. Mutagen.* 6, 390 (abstr.).
I. Russell et al., 1989, *Proc. Natl. Acad. Sci U.S.A.* 86:3704

ENU Mutagenesis in Particular

One particularly useful mutagen according to the invention is the chemical mutagen ethylnitrosourea (ENU). ENU may be used to induce genomic mutations in any organism, including but not limited to lower organisms such as insects and worms, as well as higher organisms such as vertebrates, e.g., mammals, e.g., rodents such as mice and rats, hamsters, primates, and zebra fish, cows, sheep, pigs, and dogs. Mutagenesis and DNA mutation screen also may be applied to other organisms which are used as model systems for human disease. Rats are a good candidate for practical reasons, i.e., since mouse-based animal facilities are able to breed and maintain rats. The inventive methods are easily applicable to the rat and provides a method for producing and identifying mutations in specific rat genes.

Described below is the applicability of ENU mutagenesis of mice.

The animals are housed in a mouse facility which conforms to government regulations for animal care. There are several veterinarians who supervise and monitor the animal welfare. C3H male mice are injected interperitoneally with ENU. We have about 150 males injected every 3 weeks to provide breeding stock. They are mated with either one or two untreated females in a cage (a plastic box with wire lid). Every couple of days the males are put in with new females, each of which will have 5–6 offspring (F1). The females are pregnant for 3 weeks (21 days) and after birth the babies are kept with their mothers for 3 weeks, at which time they are weaned, and a little clip of tail is taken before the babies are transferred into single sex cages (boxes), each housing 6–7 mice. The tail clip is taken at this time because mice of that age do not react to the clip; apparently there is no pain. At later ages they do react, and would need anesthetic, while at earlier ages the tail is smaller, yielding less DNA. Also it is convenient, as at weaning the mice are given a unique identifying number and are being handled anyway for transfer to another cage. A room holds about 300 cages, with roughly 1750 mice per room. Hexagen has six such rooms. The population of mice is kept at ~10,000 (there are 8000 now, but will be 10,000 in July). Once at 10,000 population, 2,000 new arrive each month and the 2,000 oldest (aged 5 months) depart. This is done because virgin female mice will not mate after a few months, although we can always obtain eggs from them and use IVF to recover. Male mice also lose interest in mating after approximately 9–12 months.

Previous mutagenesis experiments used in excess of 500,000 mice for which mutagenesis was induced by the chemical mutagen ENU. The genes involved were assayed indirectly by observation of phenotypic changes in the mice. ENU is believed to produce mutations at random throughout the genome, and the frequency of mutations, determined for numerous genes, is in the range of 0.5–1.5 mutant mice per 1000 mice, irrespective of the gene screened. In the past, the presence of mutations could only be inferred on the basis of a phenotype in the mutated mice. Most of these mutations do not produce an obvious phenotypic change in the heterozygous state and required additional breeding to make the mutations homozygous (F2 and F3 generations) to observe the effect of the mutation. Mutagenesis and mutant screening according to the invention does not require a previously-determined mutant phenotype, as the F1 generation mouse DNA is analyzed directly for the presence of a mutation in the gene of interest. In 1000 mice, 0.5–1.5 mutations in any gene may be detected. By screening 10,000 mice, it is possible to identify 5–15 mice, each carrying heterozygous mutations in a target gene. Any number of genes can be screened in these same 10,000 mice. Assuming 100,000 genes in a mammalian genome, then each mutagenized mouse is carrying mutations in one copy of approximately 100 different genes. The additional mutant genes in each mouse are easily removed by breeding. ENU mutagenesis of mice is performed as described in Example 1.

Using ENU mutagenesis, it is expected that the gene of interest will be mutated to produce a phenotype once in 1000 mice. If a given animal genome contains, for example, 100,000 genes, then each ENU mutated animal will contain in its ENL mutated genome one protein-altering mutation in one allele of every 100 genes.

ENU mutagenesis also may be carried out on rats, following a procedure similar, if not identical to ENU mutagenesis of mice.

ENU mutagenesis also may be carried out on zebrafish, as described herein for ENU mutagenesis of mice.

B) Radiation Mutagenesis.

In general, Xrays, gamma rays, neutrons, etc., cause DNA breakage. Cellular repair mechanisms of DNA breaks result in regions of DNA which contain large lesions, including rearrangements and deletions. Although analysis of other types of mutations are preferred according to the invention, analysis of radiation induced mutations, which tend to be larger in that they encompass more bases, are also encompassed by the invention.

UV light-induced mutations are largely single nucleotide alterations. However, because UV light does not penetrate an animal, it is used for inducing mutations in cells in culture or on exposed tissues of an animal, e.g., eyes, skin. UV mutagenesis is useful according to the invention for mutagenizing ES cells.

In addition to chemical or radiation induced mutations, mutations may be induced in an animal using insertional mutagenesis techniques, as follows.

C) Retroviral Insertion Mutagenesis

Retroviruses can be used to cause insertional mutations, and retroviral insertions are usually simple and cause little or no alteration in surrounding host DNA. Retroviral vectors are easy to use, infect a wide variety of cell types, including ES cells, are stable through multiple generations, and do not cause rearrangements of the host genome when integrated. The mutation frequency from retroviral insertion is estimated at about 1 mutation/$1.5 \times 10^6$ cells (Keuhn et al., 1987, *Nature* 326:295). (For retrovirally induced mutations in the mouse, see Harbers et al., 1984, *Proc. Natl. Acad. Sci. U.S.A.* 3:162; Soriano et al., 1987, *Genes Dev.* 1:366; and Gridley et al., 1987, *Trends Genet.* 109:235).

Untargeted retroviral insertion mutagenesis is performed on ES cells as follows. Briefly, ES cells are transfected with a retrovirus which integrates into the genome at random (e.g., 1 integration per genome). If the insertion lands in a gene or control element of a gene, the insertion will result in inactivation of the gene. Mice may be made from the ES cells and then introduced into the germ line for breeding. A detailed description of retroviral insertion mutagenesis is found in *Methods Enzymol.*, vol. 225, 1990.

D) Promoter- or Gene-Trapping Mutagenesis

Entrapment vectors, first described in bacteria (Casadaban and Cohen, 1979, *Proc. Natl. Acad. Sci. U.S.A.* 76:4530; Casadaban et al., 1980, *J. Bacteriol.* 143:971) permit selection of insertional events that lie within coding sequences. Entrapment vectors can be introduced into pluripotent ES cells in culture and then passed into the geinline via chimeras (Gossler et al., 1989, *Science* 244:463; Skarnes, 1990, *Biotechnology (NY)* 8:827). Promoter or gene trap vectors often contain a reporter gene, e.g., lacZ, lacking its own promoter and/or splice acceptor sequence upstream. That is, promoter gene traps contain a reporter gene with a splice site but no promoter. If the vector lands in a gene and is spliced into the gene product, then the reporter gene is expressed. Enhancer traps have a minimal promoter which requires an enhancer to function, and contains a reporter gene. If the vector inserts near an enhancer, then the reporter gene is expressed.

The vector may be introduced into the ES cells by electroporation or using a retrovirus. Activation of the reporter gene can only occur when the vector is within an active host gene and requires generation of a fusion transcript with the host gene. The reporter gene activity then provides an easy assay for integrations in expressed genes. These DNA integrations are highly mutagenic because they interrupt the endogenous coding sequence. It is estimated that the frequency of obtaining a mutation in some gene of any in the genome using a promoter or gene trap is about 45%. A detailed description of retroviral insertion mutagenesis is found in *Methods Enzymol.*, vol. 225, 1990.

E) Mutagenesis as a Result of Deficiency of a DNA Repair Enzyme

The invention encompasses mutagenesis as a result of a deficiency in a DNA repair enzyme; i.e., the presence in an organism of a mutant gene encoding a mutant DNA repair enzyme is expected to generate a high frequency of mutations (i.e., about 1 mutation/10,000 genes–1 mutation/10,000 genes) in the genome of the organism to be useful according to the invention. DNA repair enzymes include but are not limited to topoisomerases, helicases, and recombinases. Examples of genes encoding DNA repair enzymes include but are not limited to Mut H, Mut S, Mut L, and Mut U, and the homologs thereof, including mammalian homologs. Such homologs include MSH 1–6, PMS 1–2, MLH 1, GTBP, and ERCC-1.

McWhir et al., 1993, *Nat. Genet.* 5:217 describe a mouse containing a defective DNA repair enzyme resulting from a mutation in the DNA repair gene ERCC-1. In nucleotide excision repair, damaged bases are removed with adjacent residues as an oligonucleotide and the resulting gap is then patched by repair synthesis. ERCC-1 is required for the incision step necessary to remove damaged DNA. Mice were generated containing the defective gene by targeting the excision repair cross complementing gene ERCC-1 in the embryonic stem cell line, HM-1. Homozygous ERCC-1 mutants died before weaning; however, heterozygous ERCC-1 mutants survived and were available for mating. It is contemplated according to the invention that a mammalian organism heterozygous for a mutant gene encoding a DNA repair enzyme may be used to screen for a mutation in a gene of interest.

Where the organism is not an animal, the mutagenesis and breeding procedures may be adapted as necessary. For instance, to produce a mutant population of plants, it may be desired to mutagenize pollen, which can then be used to produce a suitable plurality of mutagenized organisms. The totipotency of plant cells also facilitates the generation of further organisms carrying a mutation of interest, both heterozygotes and homozygotes.

PREPARATION OF DNA SAMPLE AND PROBE

A DNA sample for analysis according to the invention may be prepared from any tissue or cell line, and preparative procedures are well-known in the art. The preparation of genomic DNA from tail tissue is performed as follows. Approximately ⅓ of the tail is removed from a 10-day old mouse, and placed in 500 μl TB buffer (50 mM Tris-HCl, pH 8.0, 100 mM NaCl, 1% SDS, 600 μg/ml proteinase K) and incubated overnight at 55 ° C. The sample is then extracted with 500 μl 1:1 (w/w) phenol/chloroform and precipitated with two volumes ethanol. The DNA pellet is then resuspended in 500 μl H2O.

cDNA samples also may be prepared according to the invention, i.e., DNA that is complementary to RNA such as MRNA. The preparation of cDNA is well-known and well-documented in the prior art.

Tissues which are useful for obtaining a DNA or RNA sample according to the invention include but are not limited to blood cells, brain, gonad, liver, heart, kidney. adrenal, spleen, and muscle.

A probe useful according to the invention is a nucleic acid having a sequence that is unique to the gene of interest and which is preferably no longer than 30–40 nucleotides, and optimally less than 25 nucleotides, e.g., 18–22 nucleotides, with a minimum of 10 nucleotides. The preparation and labeling of nucleic acid probes is well-known and well-documented in the prior art.

MUTATION DETECTION ACCORDING TO THE INVENTION

Mutation detection analysis is performed according to the invention on a number of DNA samples simultaneously in order to increase the efficiency of obtaining as many mutations as possible in a given gene of interest, or as many mutations as possible in a given organism. It is contemplated according to the invention that three general approaches to mutation screening are particularly useful. First, a single gene is examined for mutations using a nucleic acid probe which is unique to that gene, and a number of mutant organisms are screened in order to provide mutation detection in the single gene. Generally, this approach will involve screening a larger number of organisms in order to detect a mutation in a single gene. Second, a single gene is examined for mutations using a mixture of unique nucleic acid probes (a multiplex probe) for that gene, and a number of mutant organisms are screened to provide mutation detection in the gene examined. Generally, this approach to mutation detection involves screening fewer organisms in order to detect a mutation in at least one of the genes being tested. Third, several genes of interest (i.e., two-three) are examined for mutations using a mixture of several probes, each of which is unique for a given gene. Generally, this approach will result in screening of a large number of organisms in order to detect a mutation in one of the genes of interest.

Provided below is a description of a particularly useful combination of mutagenesis and mutation detection according to the invention. This combination involves ENU mutagenesis of male mice, mating to allow production of F1 offspring, and mutation detection using SSCP screening. Other mutation detection techniques which are useful according to the invention, i.e., with ENU mutagenesis or with other mutagenesis techniques, are also disclosed below.

Single Strand Conformation Polymorphism (SSCP) Screening and Fluorescent SSCP Screening One approach to detecting DNA mutations in a mutagenized organism is single strand conformation polymorphism (SSCP) (Glavac et al., 1993, *Hum. Mutat.* 2:404; Sheffield et al., 1993, *Genomics* 16:325). SSCP is a simple and effective technique for the detection of single base mutations. This technique is based on the principle that single-stranded DNA molecules take on specific sequence-based secondary structures (conformers) under nondenaturing conditions. The detection of point mutations by single stranded conformation polymorphism is believed to be due to an alteration in the structure of single stranded DNA. Molecules differing by as little as a single base substitution may form different conformers and migrate diffcrently in a nondenaturing polyacrylamide gel. Mutant single stranded DNAs are identified by an abnormal mobility on polyacrylamide gels. All types of point mutations and short insertions or deletions lying within the probe region (between the PCR primers) can be detected and with apparently equal efficiency. This technique has proven useful for detection of multiple mutations and polymorphisms. SSCP sensitivity varies dramatically with the size of the DNA fragment being analyzed. The optimal size fragment for sensitive detection by SSCP is approximately 150–300 bp.

When single stranded DNA or double stranded DNA is electrophoresed through a gel matrix, the mobility of the DNA fragment is dependent on its size. Small molecules pass through the pores in the matrix more easily than large molecules and so migrate faster. Conventionally, electrophoresis of single stranded DNA involves a 'denaturing' gel which maintains the single strandedness of the molecules. The denaturant in polyacrylamide gels is typically urea and in agarose gels is typically formamide or sodium hydroxide. The SSCP gel is unconventional in that single stranded DNA is loaded on the gel, but the gel does not contain a denaturant, i.e., the gel is 'non-denaturing'. Running single stranded DNA on this type of gel permits intramolecular interactions to occur. In other words, the single stranded DNA is able to (partially) bind to itself. As the DNA is not running as a linear molecule on an SSCP gel, the mobility of the DNA is governed by both its size and tertiary structure (conformation). The tertiary structure of a single stranded DNA fragment is dependent on the sequence of the entire fragment. If a mutation exists in a given fragment, the conformation vill usually be altered. The technique is performed as follows.

One or more test DNA samples are prepared for analysis as described above, and subject to PCR amplification. Oligonucleotide primers are synthesized by standard phosphoramidite chemistry on an Applied Biosystems Model 391 DNA Synthesizer. Amplifications are performed in a total volume of 10 ml containing 50 mM KCl, 10 mM Tris-HCl, pH 9.0 (at 25° C.), 0.1% Triton X-100, 1.5 mM MgCl2, 0.2 mM of dGTP, dATP, dTTP, 0.02 mM of non radioactive dCTP, 0.05 ml [a-33P] dCTP (1,000–3,000 Ci mmol-1; 10 mCi ml-1), 0.2 uM each primer, 50 ng genomic DNA (or 1 ng of cloned DNA template) and 0.1 U Taq DNA polymerase. The PCR cycling profile is as follows: preheating to 94° C. for 3 min followed by 94° C., 1 min; annealing temperature, 30 sec; 72° C., 45 sec for 35 cycles and a final extension at 72° C. for 5 min. Annealing temperature is different for each PCR primer pair. Amplifications using Vent Taq polymerase (New England Biolabs) are performed in a total volume of 10 ul using the buffer provided by the manufacturer with 1 mM each of dGTP, dATP, dTTP. 0.02 mM dCTP, 0.25 ul [a-33P] dCTP (1,000–3,000 Ci mmol-1;10 mCi ml-1), 0.2 uM of each primer, 50 ng of genomic DNA (or 1 ng of cloned DNA template) and 0.1 U of Vent Taq DNA polymerase. Samples are heated to 98° C. for 5 min prior to addition of enzyme and nucleotides. The PCR cycling profile is 98° C., 1 min; annealing temperature, 45 sec; 72° C., 1 min for 35 cycles, followed by a final extension at 72° C. for 5 min.

SSCP analysis is performed as follows. Ten ul of formamide dye (95% formamide, 20 mM EDTA, 0.05% bromophenol blue, 0.05% xylene cyanol) are added to 10 ul of radioactive PCR products. The reactions are denatured at 100° C. for 5 min, then placed on ice. Two ul are loaded onto 8% acrylamide:bisacrylamide (37.5:1), 0.5× TBE (45 mM Tris-borate, 1 mM EDTA), 5% glycerol gels. Electrophoresis is carried out at 25 W at 4° C. for 8 hours in 0.5× TBE. Dried gels are exposed to X-OMAT ARfilm (Kodak) and the autoradiographs are scored for aberrant migration of bands (band shifts).

SSCP may be optimized, as desired, as taught in Glavac et al., 1993, *Hum. Mutat.* 2:404.

fSSCP Analysis

The invention also contemplates screening of multiple samples of mutagenized DNA simultaneously. The high throughput required for mutation screening of a large number of samples is advantageously achieved by pooling and multiplexing of DNA samples in fluorescent SSCP (fSSCP) assays (Makino et al., 1992, *PCR Methods Appl.* 2:10; Ellison et al., 1993, *Biotechniques* 15:684). PCR products are visualized and analyzed using an ABI fluorescent DNA sequencing machine. Different color fluorochromes (4 different fluorochromes are now available) can be used for different primer pairs. The advantages of fSSCP over SSCP is that the latter requires handling of radioactive materials whereas fSSCP does not. Data collection is automated, and data analysis programs can be used to flag aberrant migrating samples, whereas SSCP evaluation involves visual examination, and correction for lane to lane variations in electrophoretic conditions is not possible.

fSSCP Analysis is performed as follows.

Amplifications are performed in a total volume of 10 ul containing 50 mM KCl, 10 mM Tris-HCl, pH 9.0 (at 25° C.), 0.1% Triton X-100, 1.5 mM MgCl2, 0.2 mM of dGTP, dATP, dTTP, dCTP, 0.2 uM primer labeled with one of the fluorochromes HEX, FAM, TET or JOE, 50 ng genomic DNA (or 1 ng of cloned DNA template) and 0.1 U Taq DNA polymerase. The PCR cycling profile is as follows: preheating to 94° C. for 3 min followed by 94° C., 1 min; annealing temperature, 30 sec; 72° C., 45 sec for 35 cycles and a final extension at 72° C. for 5 min. Annealing temperature is different for each PCR primer pair. Amplifications using Vent Taq polymerase (New England Biolabs) are performed in a total volume of 10 ul using the buffer provided by the manufacturer with 1 mM each of dGTP, dATP, dTTP, dCTP, 0.2 uM primer labeled with one of the fluorochromes HEX, FAM, TET or JOE, 50 ng genomic DNA (or 1 ng of cloned DNA template) and 0.1 U of Vent Taq DNA polymerase. Samples are heated to 98° C. for 5 min prior to addition of enzyme and nucleotides. The PCR cycling profile is 98° C., 1 min; annealing temperature, 45 sec; 72° C., 1 min for 35 cycles, followed by a final extension at 72° C. for 5 min. Annealing temperature is different for each PCR primer pair.

Two ul of fluorescent PCR products are added to 3 ul formamide dye (95% formamide, 20 mM EDTA, 0.05% bromophenol blue, 0.05% xylene cyanol), denatured at 100° C. for 5 min, then placed on ice. Thereafter, 0.5–1 ml of Genescan™ 1500 size markers are added as an internal standard. Two ul of the mix is loaded onto 8% or 10% acrylamide:bisacrylamide (37.5:1), 0.5× TBE (45 mM Tris-borate, 1 mM EDTA), 5% glycerol gels and electrophoresis is performed on an ABI 377 DNA sequencing machine. Gel temperature is maintained at 4 to 10° C. by an external cooling unit connected to the internal cooling plumbing and chambers. Electrophoresis is carried out at 2500–3500 volts for 4–10 hours in 0.5× TBE. Data is automatically collected and analyzed with Genescan and Genotype analysis software (ABI).

The SSCP procedure identifies regions of 150–300 base pairs containing a mutation. To specifically identify the sequence change, the fragment which shows the aberrant migration is amplified again from the mutated mouse DNA using non fluorescent primers and the sequence determined using standard DNA sequencing technology.

Although SSCP and fSSCP techniques are preferred according to the invention, any DNA mutation detection system can be employed to test for mutations, including DNA sequencing. Additional DNA detection techniques useful according to the invention are described below.

Denaturing Gradient Gel Electrophoresis

Denaturing gradient gel electrophoresis (DGGE) is a gel system which allows electrophoretic separation of DNA fragments differing in sequence by as little as 1 base pair. The separation is based upon differences in the temperature of strand dissociation of the wild-type and mutant molecules. As the fragments migrate down the gel, they are exposed to an increasing concentration of denaturant in the gel. When the molecules reach a critical denaturant level, the DNA strands begin to dissociate. This causes a significant reduction in the fragment's mobility. The position of this critical point is a function of the Tm, the point at which mobility retardation for wild-type and mutant molecules will be different, thus resulting in their separation. The mutation detection rate of DGGE approaches 100%. It is relatively simple to perform, does not require radioisotopes or toxic chemicals, but does require some specialist equipment. The main difference between DGGE and other mutation scanning techniques is that the behavior of DNA molecules on DGGE gels can be modeled by computer, hence the detectability of a mutation in a given fragment can be accurately predicted. Fragment sizes are limited to between 100 and 800 bp due to the resolution limit of polyacrylamide gels. For a method of efficient transfer of genomic DNA fragments from the gel following DGGE, see U.S. Pat. No. 5,190,856.

Chemical Cleavage of Mismatches

The detection of mutations by chemical cleavage of mismatch (CCM) is another mutation scanning techniques useful according to the invention. It relies upon the chemicals hydroxylamine and osmium tetroxide to react with the mismatch in a DNA heteroduplex. Subsequent treatment with piperidine cleaves the heteroduplex at the point of mismatch. Mutations are detected as fragments smaller than the untreated heteroduplex on denaturing polyacrylamide gels.

The probable 100% detection rate, coupled with the ability to scan DNA fragments up to 1 kb in size, make CCM seem an ideal mutation detection method. CCM is particularly useful where it is desired that all mutations in a fragment of DNA are detected or where it is desired to detect a mutation-free piece of DNA.

Constant Denaturant Capillary Electrophoresis (CDCE) Analysis

CDCE analysis is particularly useful in high throughput screening, i.e., wherein large numbers of DNA samples are analyzed. CDCE analysis combines several elements of replaceable linear polyacrylamide capillary electrophoresis and constant denaturant gel electrophoresis. The method is a fast and high resolution procedure with a high dynamic range, and is automatable. The method is described in detail in Khrapko et al., 1994, *Nucleic Acids Res.* 22:3:364, and involves the use of a zone of constant temperature and a denaturant concentration in capillary electrophoresis. Linear polyacrylamide gels are used at viscosity levels that permit facile replacement of the matrix after each run. For a typical 100 bp fragment of DNA, point mutation-containing heteroduplexes are separated from wild type homoduplexes in less than 30 minutes. Using laser-induced fluorescence to detect fluorescent-tagged DNA, the system has an absolute limit of detection of 3×10(4) molecules with a linear dynamic range of six orders of magnitude. The relative limit of detection is about 3/10,000, i.e., 100,000 mutant sequences are recognized among $3 \times 10^8$ wild type sequences. This approach is applicable to analysis of low frequency mutations, and to genetic screening of pooled samples for detection of rare variants.

RNase Cleavage

Various ribonuclease enzymes, including RNase A, RNase T1 and RNase T2 specifically digest single stranded RNA. When RNA is arnealed to form double stranded RNA or an RNA/DNA duplex, it can no longer be digested with these enzymes. However, when a mismatch is present in the double stranded molecule, cleavage at the point of mismatch may occur. The most commonly used and studied ribonuclease for mutation detection is RNase A.

Ribonuclease A specifically digests single stranded RNA. The enzyme can also cleave heteroduplex molecules at the point of mismatch. The extent of cleavage at single base mismatches is not only dependent on the type of mismatch, but also on the sequence of DNA flanking the mismatch Mutations are detected as fragments smaller than the uncleaved heteroduplex on denaturing polyacrylamide gels.

The technique is based upon forming a heteroduplex between a radiolabelled single stranded RNA probe (riboprobe) and a patient-derived PCR product. The resulting heteroduplex is an RNA/DNA hybrid duplex. When treated with RNase A, if a point mutation is present, the RNA strand of the duplex may be cleaved. The sample is then heated to denature and run on a denaturing polyacrylamide gel. If the RNA probe has not been cleaved, its size will be that of the PCR product. If the probe has been cleaved, its size will be smaller. As with the other mutation detection techniques, deletions as small as 1 bp are easily detectable. Small insertions may not be as easily detected as small deletions, as 'looping-out' occurs on the target strand rather than the probe strand.

Heteroduplex Analysis

Heteroduplex molecules, i.e., double stranded DNA molecules containing a mismatch, can be separated from homoduplex molecules on ordinary gels. The mutation detection rate of heteroduplex analysis is unknown, but it is clearly significantly lower than 100%. It would appear that it is not the nature of the mismatch, but the sequence of DNA flanking the mismatch which affects the detectability. Mismatches in the middle of DNA fragments are detected most easily. Although heteroduplex analysis lacks sensitivity, it may be considered useful according to the invention due to its simplicity.

Mismatch Repair Detection (MRD)

MRD is an in vivo method that utilizes a change in bacterial colony color to detect DNA sequence variation. DNA fragments to be screened for variation are cloned into two MRD plasmids, and bacteria are transformed with heteroduplexes of these constructs. The resulting colonies are blue in the absence of a mismatch and white in the presence of a mismatch. MRD is capable of detecting a single mismatch in a DNA fragment as large as 10 kb in size.

MRD permits high-throughput screening of genetic mutations, and is described in detail in Faham et al., 1995, *Genome Res.* 5:474.

Mismatch Recognition by DNA Repair Enzymes

DNA repair is another system which has the potential for exploitation in mutation detection. The *E.coli* mismatch correction systems are the well-understood. Three of the proteins required for the methyl-directed DNA repair pathway: MutS, MutL and MutH are sufficient to recognize 7 of the possible 8 single base-pair mismatches (not C/C mismatches) and cut/nick the DNA at the nearest GATC sequence. The MutY protein, which is involved in a different repair system can also be used to detect A/G and A/C mismatches. Some mammalian enzymes are also useful: thymidine glycosylase can recognize all types of T mismatch and 'all-type endonuclease' or Topoisomerase I is capable of detecting all 8 mismatches, but does so with varying efficiencies, depending on both the type of mismatch and the neighboring sequence.

The MutS gene product is the methyl-directed repair protein which binds to the mismatch. Purified MutS protein has been used for mutation detection in several ways. Gel mobility assays can be performed in which DNA bound to the MutS protein migrates more slowly through an acrylamide gel than free DNA. This system has been used to detect single base mismatches.

An alternative version of MutS mismatch recognition, which does not require gel electrophoresis, involves the immobilization of MutS protein on nitrocellulose membranes. Labeled heteroduplexed DNA is used to probe the membrane in a dot-blot format. When both DNA strands are used, all mismatches can be recognized by binding of the DNA to the protein attached to the membrane. Although C/C mismatches are not detected, the corresponding G/G mismatch derived from the other strand is recognized. The technique is very attractive in every way, it being simple, cheap, and amenable to automation. The detection efficiency however may be limited by the size of the DNA fragment. The system works well for very short fragments.

Sequencing by Hybridization (SBH)

In this method, arrays of short (8–10 base long) oligonucleotides are immobilized on a solid support in a manner similar to the reverse dot-blot and probed with a target DNA fragment.

The system is based on advanced chemistry in which the oligonucleotides are not synthesized separately and then fixed onto the support, but are synthesized together directly on the support. The synthesis system begins with a silicon chip coated with a nucleotide linked to a light-sensitive chemical group which is used to illuminate particular grid co-ordinates removing the blocking group at these positions. The chip is then exposed to the next photoprotected nucleotide, which polymerizes onto the exposed nucleotides.

In this manner, with successive rounds of nucleotide additions, oligonucleotides of different sequences can be synthesized at different positions on the solid support. Thirty-two cycles of specific additions (i.e., 8 additions of each of the four nucleotides) should enable the production of all 65,536 possible 8-mer oligonucleotides at defined positions on the chip.

When the chip is probed with a DNA molecule, e.g., a fluorescently labeled PCR product, fully matched hybrids should give a high intensity of fluorescence and hybrids with one or more mismatches should give substantially less intense fluorescence. The combination of the position and intensity of the signals on the chip enables computers to derive the sequence.

Allele-Specific Oligonucleotide Hybridization

Under specific hybridization conditions, an oligonucleotide will only bind to a PCR product if the two are fully matched. A single base pair mismatch is sufficient to prevent hybridization. The use of a pair of oligonucleotides, one carrying the mutant base and the other carrying the wild type base can be used to determine a PCR product as being homozygous wild type, heterozygous wild type mutant or homozygous mutant for a particular known mutation. This is termed allele-specific oligonucleotide (ASO) hybridization or the 'dot-blot'. In conventional dot blots, the PCR product is fixed onto a nylon membrane and probed with a labeled oligonucleotide. In the 'reverse dot blot', an oligonucleotide is fixed to a membrane and probed with a labeled PCR product. The probe may be isotopically labeled, or non-isotopically labeled. In addition, a number of Pcr amplified samples may be typed for a single known mutation.

Allele-Specific PCR

Many mutation diagnostic methods are procedures which analyze PCR-amplified DNA. The allele-specific polymerase chain reaction (also called the amplification refractory mutation system or ARMS) differs in that the assay occurs within the PCR reaction itself Sequence-specific PCR primers which differ from each other at their terminal 3' nucleotide are used to only amplify the normal allele in one reaction, and only the mutant allele in another reaction. When the 3' end of a specific primer is fully matched, amplification occurs. When the 3' end of a specific primer is mismatched, amplification fails to occur. Amplification is scored by agarose gel electrophoresis analysis of several known mutations. The genotype of a (homozygous) wild-type sample is characterized by amplification products in both reactions, and a homozygous mutant sample generates product in only the mutant reaction.

In a variation of this assay, the 5' ends of the allele-specific primers are labeled with different fluorescent labels, and the 5' end of the common primers are biotin labeled. The wild-type specific and the mutant-specific reactions then may be performed in a single tube. The advantages of this approach is that gel electrophoresis is not required and the method is amenable to automation.

Primer-Introduced Restriction Analysis

Primer-introduced restriction analysis (PIRA) is a technique which allows known mutations to be diagnosed by restriction digestion. By introducing a base change close to the position of a known mutation by a mismatch in the PCR primer, it is possible to create a restriction endonuclease recognition site that is diagnostic for the mutation. The combination of the altered base in the primer sequence and the altered base at the mutation site, has the effect of creating a new restriction target site. The approach may be used to create a new target site on either the wild-type allele or the mutant allele. In such a situation, the homozygous wild-type form would be characterized by a single band of the full-length size. The homozygous mutant form is characterized by a single band of the reduced size and the heterozygous form by bands of both sizes. The different size wild-type vs. mutant PCR fragments following restriction digestion, are analyzed by gel electrophoresis.

Oligonucleotide Ligation Assay

When two oligonucleotides, annealed to a strand of DNA are exactly juxtaposed, they can be joined by the enzyme DNA ligase. A single base pair mismatch at the junction of the two oligonucleotides is sufficient to prevent ligation. Rather than assaying ligation by gel electrophoresis an and visualization of a new larger sized DNA fragment, ligation is scored by assaying for labels on the two oligonucleotides becoming present on a single molecule.

When ligation is scored by ELISA and reactions are conducted in 96-well microtiter plates, the oligonucleotide ligation assay can be performed by robot and the results analyzed by plate reader and fed directly into a computer. The method is therefore excellent for scoring of a known mutation in a large number of samples. The assay comes in two main forms: the oligonucleotide ligation assay, which is performed on PCR-amplified DNA, and the ligase chain reaction, which is performed on genomic DNA and amplified with a thermostable DNA ligase.

Direct DNA Sequencing

Mutation detection according to the invention also may be carried out by directly sequencing the mutant DNA sample in the region of the gene of interest, using DNA sequencing procedures well-known in the art.

Mini-Sequencing

The technique of mini-sequencing (also known as single nucleotide primer extension) can be used to diagnose any known point mutation, deletion or insertion. Obtaining sequence information at just a single base pair only requires the sequencing of that particular base. This can be done by including only one base in the sequencing reaction rather than all four. When this base is labeled and complementary to the first base immediately 3' to the primer (on the target strand), the label will not be incorporated. Thus, a given base pair can be sequenced on the basis of label incorporation or failure of incorporation without the need for electrophoretic size separation.

5' Nuclease Assay

The 5' nuclease assay is a technique that monitors the extent of amplification in a PCR reaction on the basis of the degree of fluorescence of the reaction mix. Low fluorescence indicates no or very poor amplification and high fluorescence indicates good amplification. This system can be adapted for identification of known mutations, without the need for any post-PCR analysis other than fluorescence emission analysis. The 5' to 3' exonuclease activity of Taq polymerase is utilized to assay for PCR amplification. The enzyme cleaves 5' terminal nucleotides of double stranded DNA. Its preferred substrate is a partially double stranded molecule, cleaving the strand with the closest free 5' end. In the 5' nuclease assay, an oligonucleotide 'probe' which is phosphorylatcd at its 3' end so that it cannot act as a DNA synthesis primer is included in the PCR reaction. The probe is designed to anneal to a position between the two amplification primers. When an actively extending Taq polymerase molecule reaches the probe molecule, it partially displaces it and then cleaves the probe at or near the single stranded/double stranded cleavage until the entire probe is broken up and removed from the template. The polymerase continues this process of displacement and cleavage until the entire probe is broken up and removed from the template. The labeling system monitors removal of the probe. The probe is labeled with two different fluorescent labels at different positions. One label has a localized quenching effect on the fluorescence of the other (reporter) label. This effect is mediated by energy transfer from one dye to the other, but requires the two dyes to be in close proximity. The cleavage of the probe between the reporter and the quencher dyes physically separates the two dyes and so results in an increase in fluorescence which is proportional to the yield of the PCR product.

Representational Difference Analysis (RDA)

RDA is described in detail in Lisitsyn et al., 1993, *Science* 259:946, and an adaptation which combines selective breeding with RDA is described in Lisitsyn et al., 1993, *Nat. Gen.* 6:57. RDA finds dissimilarities through the application of a powerful approach to subtractive hybridization. To compare tester and driver genomes, one first creates simplified representation, called amplicons, from both samples (consisting, for example, of those BglII fragments that are small enough to be amplified by the polymerase chain reaction (PCR)). The iterative subtraction step begins with the ligation of a special adaptor to the 5' end of fragments in the tester amplicon. The tester amplicon is then melted and briefly reannealed in the presence of a large excess of competing driver amplicon. Those tester fragments that reanneal (which are preferentially those absent from the driver) can serve as a template for the addition of the adaptor sequence to its partner's 3'-end, which allow those fragments to be exponentially amplified by PCR. This procedure is then repeated to achieve successively higher enrichment.

RDA may be used to clone sequences that are either wholly absent or present in the driver DNA, but in a restriction fragment too large to be amplified in the amplicon. The former case may arise from a total deletion; the latter from a restriction fragment length polymorphism with the short allele present in the tester but not the driver. It is easy to conceive of myriad uses for RDA including subtracting tumor DNA from normal DNA to identify regions showing homozygous or heterozygous deletions; finding fragments present in a parent with a dominant disorder but absent in his unaffected offspring; and finding mRNAs expressed in normal but absent in mutant tissue.

EXAMPLE 1

Extensive studies of ENU mutagenesis in mice have shown that a phenotypic trait induced by mutation of a single gene appears in ENU treated mice at an average frequency of I per 1000 mice (Russell et al., 1979, *Proc. Natl. Acad. Sci. U.S.A.* 76:5818; Favor et al., 1983, *Mut. Res.* 110:367; and Favor, 1986, *Mut. Res.* 162:69). By performing DNA mutation analysis of a gene in thousands of ENU treated mice, it is predicted that independent mutations will be found which have an affect on the function of the gene product. The mutations may be detected directly in the genomic DNA or by converting mRNA to cDNA and testing cDNA.

ENU mutagenesis of an animal may be performed as follows.

Three hundred and fifty 10–12 week old C3H male mice (GO) (GSF—Forschungs Zentium Inst. For Mammalian Genetics, Oberschleissheim, Germany) are injected intraperitoneally with ENU (Serva, Heidelberg, Germany) in 1 ml or less of 55 mM phosphate buffer pH 6.0. Single doses are administered weekly for a total of 3 doses at 100 mg/kg animal weight. This treatment regime maximizes the mutation frequency without severely impairing fertility. Following a brief period of sterility, (8–12 weeks), these mice are permanently mated to C3H females. Mutagenized offspring (F1) are produced at a rate of 2000 per month, based on a litter size of 4–6 animals. The GO males are allowed to produce 50–75 F1 animals. Many more mice than this can be generated by a single GO male, but going beyond this range dramatically increases the chance of producing offspring with recurrent identical mutations. A tail clipping is taken from each mouse at weaning and used to prepare high molecular weight genomic DNA for genomic mutation analysis.

From a 10 day old mouse; approximately one-third of the tail is removed and placed in 500 µl TB buffer (50 mM Tris-HCl, pH 8, 100 mM NaCl, 1% SDS, 600 µg/ml proteinase K) and incubated overnight at 55° C. The sample is then extracted with 500 µl 1:1 (w/w) phenol/chloroform and precipitated with two volumes of ethanol. DNA pellets are resuspended in 500 µl water.

EXAMPLE 2

Mutation detection analysis is performed as follows. For a comprehensive SSCP screen of a target gene in genomic DNA, the DNA sequence must be known together with the intron/exon structure in the mouse genome or, alternatively, where intron regions are not known, primers are designed for targeting exon regions only, e.g., using cDNA sequence information, and are tested on genomic DNA. It is contemplated according to the inventive methods to screen genomic DNA from an organism, as this is the most cost effective procedure. Alternatively, where the structure and organization of the intron/exon region is not known, and genomic DNA screening is not preferred cDNA may be prepared from each organism and screened instead of genomic DNA.

For maximum mutation detection sensitivity by SSCP the target gene is PCR amplified in fragments of 150–300 base pairs. It is estimated that the average screening will cover 2,000 base pairs and will require up to 15 PCR amplifications. PCR primer pairs containing one fluorescently labeled and one un-labeled primer, or both primers labeled, are designed to amplify the entire coding region including intron/exon boundaries, with some overlap between adjacent amplicons to ensure screening of the primer regions. Each primer pair is tested and conditions optimized for their ability to amplify a unique fragment of the appropriate size (1–2 weeks for 15 primer pairs). Two thousand genomic DNA samples are prepared each month. These samples, together with DNA from 8000 F1 mice generated in the previous 4 months, are screened for mutations. All of the mice from which DNA is screened are kept alive for further (phenotypic) analysis of the mice containing mutations in the gene being screened. The DNA from 5 mutagenized mice is pooled and all five DNA samples concomitantly amplified in a single PCR reaction. Approximately 2,000 PCR reactions is required to screen 10,000 mouse DNA samples with each PCR primer pair (one amplimer).

The PCR amplifications will be performed in machines with multiple, independent thermocycling blocks each having 192 reaction capacity (1 day/amplimer). The amplification products will be assayed using a modified ABI 377 automated sequencing machine. Detection of mutations by SSCP is maximized at temperatures of 4–15° C., the current 377 automated sequencer can be modified by ABI technicians to enable the gels to be cooled.

At present there are 4 different fluorescent dye labels which are compatible (at least one additional dye currently under development). and can be distinguished by its unique fluorescence when run in a single lane.

Therefore, allowing one fluorescent dye for use as a size standard, three different amplimers may be run concurrently. In a gel, 15 samples can be run per electrophoretic run in each of 36 lanes per gel (of the ABI 377 machine), which is equal to 540 samples per gel. If a gene is analyzed in 10 amplimers, then 10,000 samples are tested (10 amplimers per gene×10,000 mice). To analyze the 100,000 samples (one gene in 10,000 mice), 185 gels are used (100,000/540). Each ABI machine can run approximately 2 gels per (lay. Therefore, where 4 machines are employed, 185 gels are run in 23 days. Similarly, if a gene is analyzed using 15 amplimers, then the same type of calculation results in 277 gels; using 4 machines, the results are available in 35 days. This type of numerical analysis of feasibility of a given mutagenesis/mutation detection combination permits a determination of the technical feasibility of employing that combination of techniques. It is possible to use any mutation inducing agent, even one which produces as low as 1 mutation per genome, in a given combination, provided a mutation detection technique is available, e.g., SSCP, and the capability of testing a large number of samples of a given gene or genes of interest.

If desired, the region of DNA containing the mutation identified as described herein may be cloned or, alternatively, the gene containing the PCR-amplified region, and thus the mutation, also may be cloned, using conventional cloning techniques.

EXAMPLE 3

It is contemplated according to the invention that a plurality of DNA samples from different organisms may be pooled and screened in a single mutation detection assay. For example, where the mutation detection technique is fluorescence SCCP, the number of samples which may be combined is determined as follows.

For high throughput screening, DNA samples from different organisms may be combined (pooled) prior to amplification of the gene of interest. Using fluorescence SSCP, for example, a mutated allele appears as an aberrantly migrating peak of fluorescence. In pooled samples from, for example, 5 organisms, if 1 allele of 1 organism is mutated then $\frac{1}{10}$ of the signal (2 alleles per organism, or 10 alleles per pool of 5 organisms) is present in the shifted peak and 9 times that amount of signal is present in the normal (unmutated) migration peak. The sensitivity of fSSCP permits visualization of a peak corresponding to a shift in mobility (corresponding to a mutated allele) which is $\frac{1}{10}$ the signal of the normal unmutated alleles.

According to the invention, it is contemplated that as few as 5 DNA samples from different organisms may be pooled, or a larger number of DNA samples from different organisms may be pooled, e.g., 10 samples, 15 samples, 20 samples, 50 samples, etc. The limit of the number of different organism DNA samples which may be pooled is determined by the limits of detection of a given single sample above background in the detection technique used. For example, for fSSCP, data is produced as a peak of units of fluorescence. A peak of about 6000 units is near the practical maximum level of detection. A peak of 50 units is easily detected above background fluorescence levels. Therefore, greater than a 100-fold range of minimum–maximum detection levels is permitted using fSSCP between peak heights. If amplification of 1 allele produces a value of 50 units of fluorescence, then a pool of DNA samples from 60 different organisms (i.e., 120 alleles), where a DNA sample from a single organism contains a mutation in 1 allele, then the mutated allele produces a value of 50 fluorescence units and the combined 119 normal (unmutated) alleles produces a value of 5650 fluorescence units.

EXAMPLE 4

Phenotypic Analysis Subsequent to Identification of a Mutation in a Gene of Interest.

If desired, analysis of any phenotypes associated with a detected mutation and establishing the mode of inheritance may follow identification of a mutation in a gene of interest.

It may be useful according to the invention to subsequently analyze mice generated according to the invention to perform a second, more traditional screening regime in which the mutagenized mice described above are phenotypically screened to identify unknown genes associated with a phenotype. All F1 mice can be screened routinely for a spectrum of visible phenotypic abnormalities, for example, skeletal dysmorphologies and eye defects.

Approximately 200 F1 mice per year are bred to F2 and backcrossed to produce an F3 which produces mice that are homozygous for many of the loci mutated in the F1. Phenotypic screens may be visual, biochemical (requiring blood component analysis) or behavioral in nature. Loci identified in the phenotypic screens may be further analyzed by backcross mapping and positional cloning to identify candidate genes. The advantage of using mice for these phenotypic screens is that they are inbred and have no natural polymorphisms. That is, any changes detected in the candidate genes will have been induced by the ENU mutagenesis treatment. These candidate genes can then be screened for mutations as described above, to determine whether the function of any of the candidate genes can be related to a disease phenotype, if known. Alternatively, the invention does not require sequencing and isolation of a mutant gene, but merely the identification of a DNA mutation. Therefore, according to the invention, it is not necessary to sequence and clone a gene containing a mutation, but instead one may wish to simply map the region of the genome containing the mutation, and/or use positional cloning techniques to identify 5–10 candidate genes which are associated (positionally) with the mutation.

EXAMPLE 5

Sox-3 (both mouse Sox-3 and the human homologue SOX3) is a member of the Sox gene family, i.e., a family of about 20 genes which all contain an ~240 bp DNA sequence corresponding to a 80 amino acid segment (which is called an "HMG box") that contains about 60% or greater amino acid similarity to the SRY gene. Outside of the HMG box, the genes are very different. The HMG box is a DNA binding domain and the SOX genes which have been studied bind to DNA via this region of the protein and are likely modulators of gene expression, such as transcription factors. Sox-3 is expressed in the developing central nervous system. The complete sequence is known (see Collignon et al., 1996, *Development* 122:509 for Sox3 sequence, and Stevanovic et al., 1993, *Hum. Mol. Genet.* 2:2013 for the SOX3 gene sequence) and has an open reading frame of 1125 base pairs. FIG. 1 is a diagram of the Sox3 gene showing the location of primers which are useful according to the invention for detection of mutations in the Sox3 gene. The open reading frame of the Sox3 gene is represented by an open box, with flanking non-coding DNA represented by solid bars. Lines labeled A-I indicate fragments (amplimers) amplified by PCR using the primer pairs listed below. The size of the open reading frame in based pairs is 1150. PCR primer pairs useful to generate amplimers in the Sox3 gene to detect gene mutations have the following sequences (F=forward; R=reverse):

| A-F | GCACCTCCTTCCCGCCCC | (SEQ ID NO:1) |
| A-R | TTCGCGCCCCCGCTGCCC | (SEQ ID NO:2) |
| B-F | GAGTGGCGCGAACCCAGC | (SEQ ID NO:3) |

-continued

| | | |
|---|---|---|
| B-R | TTGGGGTTCTCCAGGGCC | (SEQ ID NO:4) |
| C-F | GAACGCGTTCATGGTGTG | (SEQ ID NO:5) |
| C-R | TACTCCTTCATGTGCACC | (SEQ ID NO:6) |
| D-F | GGAGAAGCGGCCGTTCAT | (SEQ ID NO:7) |
| D-R | GCGGCGGCGACGGCGGCG | (SEQ ID NO:8) |
| E-F | CTCGCTGCCCGGCGGCCT | (SEQ ID NO:9) |
| E-R | GGCTGCGCGTAGCCCAGC | (SEQ ID NO:10) |
| F-F | GAACGGCTGGGCCAACGG | (SEQ ID NO:11) |
| F-R | GCGGCGTTCATGTAGCTC | (SEQ ID NO:12) |
| G-F | GGCCGGCCTGCAGTACAG | (SEQ ID NO:13) |
| G-R | GCGGCGGCGGCGGCGGCC | (SEQ ID NO:14) |
| H-F | CGCCGCCGCCTACGGGCA | (SEQ ID NO:15) |
| H-R | TACATGCTGATCATGTCG | (SEQ ID NO:16) |
| I-F | CATCCGTTCGCACTCGCA | (SEQ ID NO:17) |
| I-R | TCAGATGTGGGTCAGCGG | (SEQ ID NO:18) |

The primers are located throughout the gene and therefore are unique to the Sox3 gene.

Mutations in the Sox3 gene are generated, identified, and analyzed according to the invention as follows. Mice are mutagenized using ENU mutagenesis, as described hereinabove. ENU mutagenized mice are tested by PCR with each primer set and fSSCP analysis. Several mutations in the Sox3 gene are identified.

Mice with mutations in the Sox3 open reading frame may impair or destroy Sox3 protein function. These mice may be examined and bred to observe their phenotype. Prior to ENU mutagenesis of mice, it is known that in the human SOX3 homolog, there is an individual who has a deletion which removes (minimally) SOX3 and the factor IX (blood clotting) gene. This individual has mental retardation and hemophilia. SOX3 may be linked to X-linked mental retardation. It is also known that Sox3 mRNA in mice is abundant in the central nervous system. Therefore, in the several ENU mutagenized mice for which a mutation in the Sox3 gene is identified, the phenotype of the Sox3 mutant mice are observed for, for example, neural defects, thus providing a mouse model for a mutant Sox3 gene.

EXAMPLE 6

It is contemplated according to the invention that cells in culture are mutagenized prior to producing an organism and analyzed for a mutation in a gene of interest, for example, the Sox3 gene, as described herein. One such example includes mutagenesis of ES cells, as follows.

ES cells are prepared from mice as described in Gossler et al. 1989, *Science* 244:463, and Skarnes, 1990, *Biotechnology (NY)* 8:827, and are mutagenized using retroviral mutagenesis, or gene- or promoter-trapping mutagenesis, as described in detail hereinabove. If desired, another method of mutagenesis may be used, e.g., any of the above-described mutagenesis techniques suitable for such cells, for example, by ENU mutagenesis, UV mutagenesis. 10,000–1,000,000 mutagenized ES clones are screened by ISSCP analysis using one or more primer pairs, as described in Example 5, for a mutation in the Sox3 gene, or by any other mutagenesis screening technique described herein. A mutagenized ES clone in which a Sox3 mutation is identified is then introduced by micro-injection into a mouse embryo at the blastocyst stage, and the mouse is produced via normal gestation and birth. A mouse thus produced from a Sox3 mutant ES clone will itself contain the Sox3 mutation, and thus be available for further phenotypic or biochemical studies.

EXAMPLE 7

Sox-2 (both mouse Sox-2 and the human homolog (SOX2) is also a member of the Sox gene family. Sox-2 is involved in the transcriptional regulation of the FGF-4 gene. Fibroblast growth factor 4 (FGF-4) has been shown to be a signaling molecule whose expression is essential for postimplantation mouse development and, at later embryonic stages, for limb patterning and growth. The FGF-4 gene is expressed in the blastocyst inner cell mass and later in distinct embryonic tissues, but is transcriptionally silent in the adult. The mouse Sox2 nucleotide sequence is known (see Yuan et al., 199, *Genes Dev.* 9:2635) and has an open reading frame of 956 base pairs. The human SOX2 gene is expressed in fetal brain tissue. The SOX2 cDNA is 1085 bp long and contains an open reading frame of 317 amino acids, and displays a high degree of similarity with the mouse Sox2 gene. The nucleotide sequence of the SOX2 gene is known (Stevanovic et al., 1994, *Mamm. Genome* 5:640.) PCR primer pairs useful to generate amplimers in the Sox2 gene to detect gene mutations have the following sequences (F=forward; R=reverse):

| | | |
|---|---|---|
| A-F | CCACAGTCCCGGCCGGGC | (SEQ ID NO:19) |
| A-R | GGGCTGTTCTTCTGGTTG | (SEQ ID NO:20) |
| B-F | CGGCGGCGGAGGAGGCAA | (SEQ ID NO:21) |
| B-R | TCCGCGCCCAGGCGCTTG | (SEQ ID NO:22) |
| C-F | GATGGCCCAGGAGAACCC | (SEQ ID NO:23) |
| C-R | GTCTTGGTTTTCCGCCGC | (SEQ ID NO:24) |
| D-F | CGCTCTGCACATGAAGGA | (SEQ ID NO:25) |
| D-R | CTGTCCATGCGCTGGTTC | (SEQ ID NO:26) |
| E-F | GGCGAGCGGGGTTGGGGT | (SEQ ID NO:27) |
| E-R | CGGTGCATCGGTTGCATC | (SEQ ID NO:28) |
| F-F | CTACCCGCAGCACCCGGG | (SEQ ID NO:29) |
| F-R | GAGCCCAGCGCCATACCG | (SEQ ID NO:30) |
| G-F | CTCGCCCACCTACAGCAT | (SEQ ID NO:31) |
| G-R | GGGAGGTACATGCTGATC | (SEQ ID NO:32) |
| H-F | CCACTCCAGGGCGCCCTG | (SEQ ID NO:33) |
| H-R | CCTCACATGTGCGACAGG | (SEQ ID NO:34) |
| I-F | GTGCGGCCCGGTGCCCGG | (SEQ ID NO:35) |
| I-R | AACCACCAAAAAAAGGAA | (SEQ ID NO:36) |

Mice with mutations in the Sox2 open reading frame may impair or destroy Sox2 protein function. These mice may be examined and bred to observe their phenotype and thus to gain more information of Sox2 and SOX2 gene function. Prior to ENU mutagenesis of mice, very little is known about the human SOX2 homolog other than its expression in fetal brain tissue. More is known with respect to Sox2 function as it relates to transcriptional regulation of the FGF-4 gene. Therefore, in the several ENU mutagenized mice for which a mutation in the Sox2 gene is identified, the phenotype of the Sox3 mutant mice are observed for, for example, postembryonic fetal development and limb formation, thus providing a mouse model for a mutant Sox2 gene.

Alternatively, instead of mutagenizing a mouse and analyzing DNA from the mutated mouse, or an F1 offspring of the mouse, for Sox2 mutations, ES cells from a mouse may be mutated and analyzed using the above-described Sox 2 primers, as described in Example 6 for the Sox3 gene.

EXAMPLE 8

A Drosophila gene is provided which appears to function in controlling cell growth during certain stages of the cell cycle. Drosophila cells lacking this gene grow uncontrollably in culture. Approximately 200 bp of the Drosophila gene sequence has been determined. The Drosophila gene has been used as a probe in a high stringency hybridization to identify a human clone. Cells containing the human clone are isolated and a partial sequence is available for the corresponding human gene; however, its function is not known.

The partial human gene sequence is used as a probe in a Southern analysis to hybridize to the mouse genome in order to identify a corresponding mouse sequence. The results of the hybridization indicate that the corresponding mouse sequence is a single unique sequence in the mouse genome. It is desired that mutations be identified in the corresponding mouse sequence in order to ascertain the human gene function. Therefore, PCR primers are designed. The primer sequences are either based on the partial human sequence which is available or based on the nucleotide sequence of the corresponding mouse sequence, and used according to the invention to identify mutations in a mouse homolog of the human gene.

That is, DNA samples from the F1 generation of ENU or MMU mutagenized inbred mice are screened using the primers in fSSCP to generate amplimers. Several amplimers containing a mutation are identified via a change in mobility of the amplimer. The mutated organism from which the DNA sample giving rise to the amplimer was obtained is identified, and observed with respect to its phenotype. Because the corresponding Drosophila gene is believed to function to control cell growth, phenotypes relating to loss of control of cell growth are observed. Therefore, mice containing mutations in the gene of interest are observed phenotypically for cancer-like conditions.

Alternatively, instead of obtaining DNA samples from the F1 generation of a mutagenized mouse, mouse ES cells are mutagenized with ENU or MMU and DNA samples are prepared from each ES clone. These DNA samples are then analyzed for mutations, as above, using PCR primers unique to the sequence of interest. Several mutations in the mouse sequence of interest are identified, and each corresponding ES clone containing a mutation is transferred to a mouse embryo, and the resultant newborn mouse is observed phenotypically for loss of control of cell growth.

The mutants obtained as described above indicate that the gene of interest has a role in the control of cell growth, not only in Drosophila, but also in a mammalian model system. Based on this information, the human gene is completely sequenced, and studied further for function relating to control of cell growth.

Therefore, starting with a random coding sequence, mice are identified which carry mutant copies of the gene. A phenotype associated with these mutations is identified, which could not have been predicted from the sequence alone and which was not previously known to be associated with the gene; further, mice, both heterozygous and homozygous, carrying mutant copies of the gene are produced by breeding. These mice are used for disease study and modeling, and the human homologue of the gene is identified as a target for further research.

EXAMPLE 9

Albinism I is an autosomal recessive disease characterized by absence of pigment in hair, skin and eyes which occurs with a frequency of approximately 1 in 70,000 individuals in Canada and 1 in 10,000 in Northern Ireland. In addition to the lack of pigment, common features include reduced visual acuity and photophobia (intolerance to light). The disease results from mutation in the gene encoding tyrosinase. Various phenotypes in humans have been associated with specific mutations within the gene, for example, the tyrosinase alleles "yellow" and "minimal pigment". Mutations in the homologous gene of the mouse *Mus musculus* correspondingly lead to albino mice. The mouse is a useful tool for studying many human disorders, and the identification of additional alleles of tyrosinase in mouse would allow a greater understanding of the gene function in a mammalian system. Mutations which cause a phenotype identify functionally critical regions of the protein. Mutations occurring in the DNA which change an amino acid in the tyrosinase protein, but do not disrupt protein function so as to result in an albino phenotype in the animal, define regions of the gene which are less important for protein function. To isolate tyrosinase gene mutations which either cause or do not cause a phenotype, the tyrosinase gene must be screened at the level of the DNA sequence, as a lack of phenotype (or the presence of an unpredicted phenotype) does not reveal that any given mouse may have a tyrosinase mutation.

Spontaneous mutation of DNA is a relatively infrequent event. having been observed at a frequency of 1 phenotype inducing mutation per gene per 80,000–100,000 mice. Direct screening of DNA sequence in these numbers of animals is impractical, but the mutation frequency in mouse DNA can be increased by treatment with a DNA mutagen. For example, ethylnitrosourea (ENU) induces DNA mutations to a frequency of 80-fold or greater than that of naturally induced mutations. Treatment of male mice with ENU mutates the sperm producing cells; to establish (fix) these mutations into the somatic tissue and germ cells of a mouse, ENU treated males are mated to non-mutagenised females. The resulting offspring (F1 mice) will have mutations in some of the genes from the father, while the other allele contributed by the mother will be non-mutant. Albinism I is a recessive disease, requiring that both alleles have protein-disrupting mutations to result in the albino phenotype. The maternal allele, being normal, will provide appropriate function so none of the F1 will be albino as a result of mutation of the paternal tyrosinase gene. To find mutation in the tyrosinase gene, that region of genomic DNA or nucleic acid molecules deriving from it must be scanned. One effective method for detecting unknown mutations is the Single Strand Conformation Polymorphism (SSCP) assay. which tests regions of DNA generated by PCR using probes specific to the gene being studied. An appropriate set of probes for studying the tyrosinase protein coding region of the tyrosinase gene are shown in Table 2. In this table, as in all subsequent tables listing PCR primer sequences for use in fSSCP, features of the primers are described as follows:

Amplimer name is assigned to the PCR product amplified by the corresponding pair of PCR primers. Sequencing tail sequence is the DNA sequence incorporated onto the end of each primer and is not specific to the gene; these are used to prime sequencing reactions to determine the DNA sequence of the fragment amplified by the primers. Gene Specific Annealing Sequences are the DNA sequences in each primer specific to the gene. Primer Label Color is the color of fluorescent label attached to each primer. Gene Tm is the temperature at which one-half of the primer is dissociated from the specific genomic sequence; this serves as a guide to PCR annealing temperatures. Other columns have labels which are self explanatory.

The PCR primers listed in Table 2 will test 98% of the protein coding region of the tyrosinase gene (Table 3). Information included in this summary table and all such subsequent tables is as follows: Exon # indicates the exon number of the gene corresponding to the position of the primer pair. Primer Color is the color of fluorescent label attached to the pair of primers for that amplimer. Primer Pair SSCP Coverage indicates the amount and position of sequence tested in SSCP using the corresponding primer pair. Total SSCP Coverage of ORF indicates the cumulative coverage of the gene being tested taking into account amplimer overlap. Fluorescence SSCP (fSSCP) can be used to increase the throughput rate of samples tested in an SSCP experiment. The PCR primers in Table 2 are labeled for SSCP. Multiple colored PCR products and multiple products of the same color but of different size can be run in a single lane of an fSSCP gel. For example, primer pairs A (yellow), C (green), D (blue; 306 basepair product) and J (blue, 206 basepair product) (see Table 2) can be used to probe and amplify DNA from an animal, and the products pooled and run in a single lane. In this example, 1042 DNA base pairs, corresponding to 65% of the protein-coding region of the tyrosinase gene, are examined in a single lane of a gel. By running gels with many lanes, for example 66 lanes per gel, and running many gels, for example 250 gels, 10,000 ENU F1 mice can be tested for mutation in the tyrosinase gene. ENU is known to induce mutations in the tyrosinase gene at a frequency as high as approximately 1 phenotype producing mutation per 700 mice (Hitotsumachi, et al., 1985, *Proc. Natl. Acad Sci. U.S.A.*, 82:6619–6621). In this way, multiple independent mutations in the tyrosinase gene will be discovered.

As albinism I is recessive, the F1 mice with tyrosinase mutations will not be albino. To study which mice have mutations that alter the function of the tyrosinase gene, it is necessary to first cross each F1 mutant mouse to a normal mouse to generate additional mice heterozygous for the mutation. Once a mutation has been identified, it is easy, by sequencing for example, to determine which offspring have the mutation passed on to them from their mutated parent. These F2 generation mice which are heterozygous for the mutation are bred together, and one-quarter of the offspring will be homozygous for the mutated tyrosinase gene. Examination of pigmentation (e.g. fur color) in the homozygous mutation mice will reveal the effect, if any, of each DNA mutation on tyrosinase protein function.

EXAMPLE 10

Mutations which are single nucleotide changes (base substitutions), or "point mutations", in the DNA sequence of the protein coding region of a gene can bring about any of three outcomes with regard to the primary protein sequence encoded by a gene. First, a base substitution can occur which does not alter the amino acid at that position in the protein (referred to as a "silent" mutation). Second, the base substitution can result in a "stop" signal being inserted where there is normally an amino acid present, resulting in premature termination of translation to yield a truncated protein (nonsense mutations). Third, the base substitution can cause an amino acid other than the normal one to be incorporated into the protein (missense mutations). Using amino acid distribution and codon frequencies in mammals, the probability of each of these classes of mutations resulting from a random base substitution can be calculated to be 23% silent mutations, 4% nonsense mutations and 73% missense mutations. Each class of mutation may result in no change in a protein function, complete loss of function, reductions or increases in function, or a completely different protein function altogether. Silent mutations very rarely result in changes to an protein activity, and nonsense mutations usually cause a significant change in protein function. The effect of amino acid substitutions (from missense mutations) on a protein function is highly variable depending on the position in the protein and the type of change, and is largely unpredictable.

In vitro studies of gene mutation/protein function relationships suggest that the majority of amino acid substitutions within a protein do not severely affect protein function. The elucidation of mutations in the past has used phenotype as a guide to testing a gene for mutation. This method does not discover DNA mutations which change an amino acid but do not alter the protein function. To study the proportion of mutations which cause amino acid changes that do not affect protein function enough to cause a phenotype, it is necessary to examine the DNA sequence of the gene in an animal without consideration of an associated phenotype. The mouse is an appropriate tool for studying mammalian gene function. ENU mutagenesis of male mice, followed by generation of F1 offspring by breeding to non-mutagenised female mice, yields a population of mice with induced mutations to screen at the nucleic acid level for mutations in a gene of interest.

As the type of gene being studied will have particular sensitivities to amino acid changes, it is useful to study different types of genes for mutations. The T protein is vital for the formation of posterior mesoderm and axial development in all vertebrates. Mutations of the T gene in mice are dominant, and result in a phenotype called Brachyury, involving posterior somite and notochord malformations. The T protein functions as a transcription factor, modulating the expression of other genes by interacting with DNA control regions of these genes. Tyrosine related protein-1 (Tyrp-1) is a melanocyte-specific enzyme involved in melanin synthesis. Recessive mutant alleles in mice cause a brown coat color, while a dominant allele causes an almost white appearance in black mice. fSSCP can be used to screen the ENU F1 population for mutation in these genes. Tables 4, 5, 6 and 7 show appropriate primers for generating PCR products for use in fSSCP evaluation of these two genes. Screening a large population of ENU F1 mice will identify animals with mutations in the genes being studied. The F1 animals can be examined for the Brachyury or brown phenotype caused by dominant mutations. The mice are then outbred and inbred to generate animals which are homozygous for the mutation being studied. These animals are examined for the appropriate phenotype. Some of the animals will have phenotypes associated with the DNA mutations; other mice will carry mutations that will not cause a discernible phenotype. Comparison of the type of DNA change and the presence or absence of phenotype will provide information as to the frequency of amino acid changing mutations which do not disrupt function of each of the proteins.

EXAMPLE 11

The SRY gene is the Y-chromosome-located dominant inducer of male development. Mutations in the DNA binding domain of the SRY gene in humans have been found which disable SRY protein function and result in individuals with a Y chromosome who develop as females. A single mutation outside of the DNA binding domain has been found which results in this "sex reversal". Mice with a Y chromosome carrying a deletion of Sry develop as females. No mutations involving only a single base pair of the mouse Sry gene are known. This is because sex reversed mice are not easily spotted: they appear as normal females and their sex reversal is not noted in the absence of DNA tests for the presence of the Sry gene. It is presumed, but not known, that mutations within the gene will lead to sex reversal in mice. The types and location of Sry mutations which can lead to sex reversal in the mouse are not known. In humans, some SRY mutations have variable penetrance. They sometimes do not cause sex reversal, but in subsequent generations the Y-chromosome-bearing offspring with the mutant SRY develop as females. It is unknown if such mutations exist in mice, in which they would be valuable for the study of sex determination and development abnormalities which have a parallel in humans. These "conditional" mutations cannot be discovered in males by phenotypic assays as there is no phenotype in those individuals. The mutation needs to be known and studied in subsequent generations, including studies which transfer the mutated gene to other genetic backgrounds to test the effect of modifier alleles which may be present therein.

Mutations in the DNA of mice are generated and discovered by the invention as follows: male mice are treated with ENU to provide a source of gametes bearing, mutant Sry genes. The ENU treated males are bred to normal females to provide F1 mice carrying mutations induced in the father. Screening of the Sry gene in DNA from the mutagenized mice by fSSCP identifies Y-chromosome-carrying mice with Sry mutations. Primers for examining the entire protein-coding region of the Sry gene by fSSCP are shown in Table 8, and details of tile position of the primers in the Sry gene are shown in Table 9. Animals with mutations in the Sry gene can be examined for sexual phenotype, and mutations in the gene causing sex reversal identified. The location of the mutations in the mouse Sry gene can be compared to those known in humans to be sex-reversing. Sry mutations in phenotypic males (i.e. those which are not sex-reversed) can be tested for variable penetrance by breeding to females of the same strain and of different strains. The offspring are tested for the mutated Sry gene and the sexual phenotype examined to find if the mutation being studied causes sex reversal. In this way, animal models of human sex reversal can be derived.

EXAMPLE 12

The binding of a ligand to a receptor located on the surface of a cell leads to the transmission of a signal into the cell, where a subsequent cascade of events leads to a cellular response. Ligand-receptor interactions are selective: particular ligands "fit" particular receptors correctly to direct further signalling events. Mutations in the ligand, or in the receptor, can alter the "fit" such that interactions no longer trigger signalling. It is useful to identify mutations in receptors and ligands, both those which do- and those which do not affect interactions, as a means by which to define regions of the proteins critical for function. Mast cell growth factor (MGF in mice, in humans known as stem cell factor, or SCF) is the ligand for the c-kit tyrosine kinase receptor (in humans, c-KIT). MGF/SCF is a hematopoetic growth factor critical to growth of several distinct cell lineages. Dominant mutations of the MGF and c-kit gene in mouse effects germ cell development, coat color and hematopoiesis. Mutation of c-KIT in humans can cause piebaldism, a pigmentation defect, and c-KIT mutations have been found in mast cell leukemias. Identification of multiple c-kit and MGF mutations in mice would allow molecular dissection of the respective proteins and an assessment of their phenotypes following mutation identification. Mutations which do not result in a phenotype can be studied further by breeding to mice with phenotype causing mutations in the corresponding partner gene and testing for modulation of the phenotype, thus providing a sensitive assay for subtle protein changes.

Mutations in the MGF gene and c-kit gene are identified by means of the invention as follows: F1 offspring from ENU mutagenised males and non-mutagenized females are tested for MGF and c-kit mutations by fSSCP using the fluorescent PCR primer pairs detailed in Tables 10, 11, 12 and 13. F1 mice with mutations in either gene are phenotypical ly examined for abnormalities in germ cell development, coat color and hematopoiesis resulting from dominant mutations. A mutated mouse being studied is bred to a normal mouse, and offspring carrying the heterozygous mutation are bred to one another to yield homozygotes for that mutation. On average, these mutant homozygotes make up one-fourth of the individuals in the litter. They are phenotypically examined for abnormalities in germ cell development, coat color and hematopoiesis resulting from recessive mutations. Correlations between mutations and the presence or absence of phenotypes provide information as to the locations of essential functional regions of the genes. Animals with mutations in either gene which are phenotypically silent are bred to mice with phenotype-causing mutations in the corresponding partner gene and tested for modulations of phenotype.

EXAMPLE 13

PAX6 mutations lead to a variety of anterior segment mnalformnations most commonly characterized by eye development defects broadly described as aniridia. The phenotype is panocular and variable, with features ranging from a readily visible, nearly complete absence of the iris, to small slit-like defects in the anterior layer seen only with a slit lamp. Mice with Pax-6 mutations display similar phenotypes. The disease is dominant and apparently results from haploinsufficiency: loss of function of one of the PAX6 (or Pax-6) alleles in the presence of a normal allele. Variability in the phenotype makes ascertainment of all eye abnormalities associated with Pax-6 difficult. In examination of mice for eye abnormalities, subtle phenotypes resulting from mutation of Pax-6 can be missed. It is therefore useful to first identify Pax-6 mutations in individual mice and then look carefully for associated phenotypes. Such mice can be identified by the invention by screening mice which carry ENU induced mutations. F1 mice which are the progeny of ENU-mutagenized fathers and normal mothers are screened by fSSCP to detect heterozygous mutations in the PAX6 gene. Appropriate primers for screening a portion of the Pax-6 gene are described in Tables 14 and 15. Mice which are identified as carrying mutations in the Pax-6 gene are thoroughly and carefully tested for eye abnormalities, including anterior segment anomalies. In this way, the phenotypic spectrum associated with Pax-6 mutations in mice is identified and mouse models for varying severities of aniridia in humans are identified.

EXAMPLE 14

To demonstrate the efficacy of screening DNA for mutations without using a phenotypic guide, an experiment was performed to chemically induce DNA mutations in mice, and screen the DNA from offspring of the mutagenized mice by fSSCP (fluorescent single strand conformation assay) for induced mutations without the use of phenotype information. One hundred male C3HeB/Fej inbred mice were treated with the DNA mutagen ethylnitrosourea (ENU), a DNA alkylating agent. The mutations induced by ENU are predominantly single-basepair changes in DNA. ENU is cytotoxic, killing many of the prerneiotic spermatogonia which produce sperm, and it takes time for the mutagenized spermatogonia to repopulate the testes to levels required for fertility.

Fifty mice were injected with 160 mg/kg body weight of ENU and fifty mice were given 3 injections of 80 mg/kg body weight of ethylnitrosourea at one-week intervals. The mice underwent a period of sterility ranging from 60 to 120 days, with a mean sterility of 72 days. After fertility was regained, the mice were bred with untreated female C3HeB/Fej mice to produce offspring (the F1 generation). As the mother was not mutagenized, DNA mutations induced by ENU were present as heterozygous changes in the offspring. Tail clips were taken from the F1 mice after weaning (21 days after birth) and DNA was isolated, as described above. No phenotypic data was considered in collecting or screening the samples.

Figure 2:
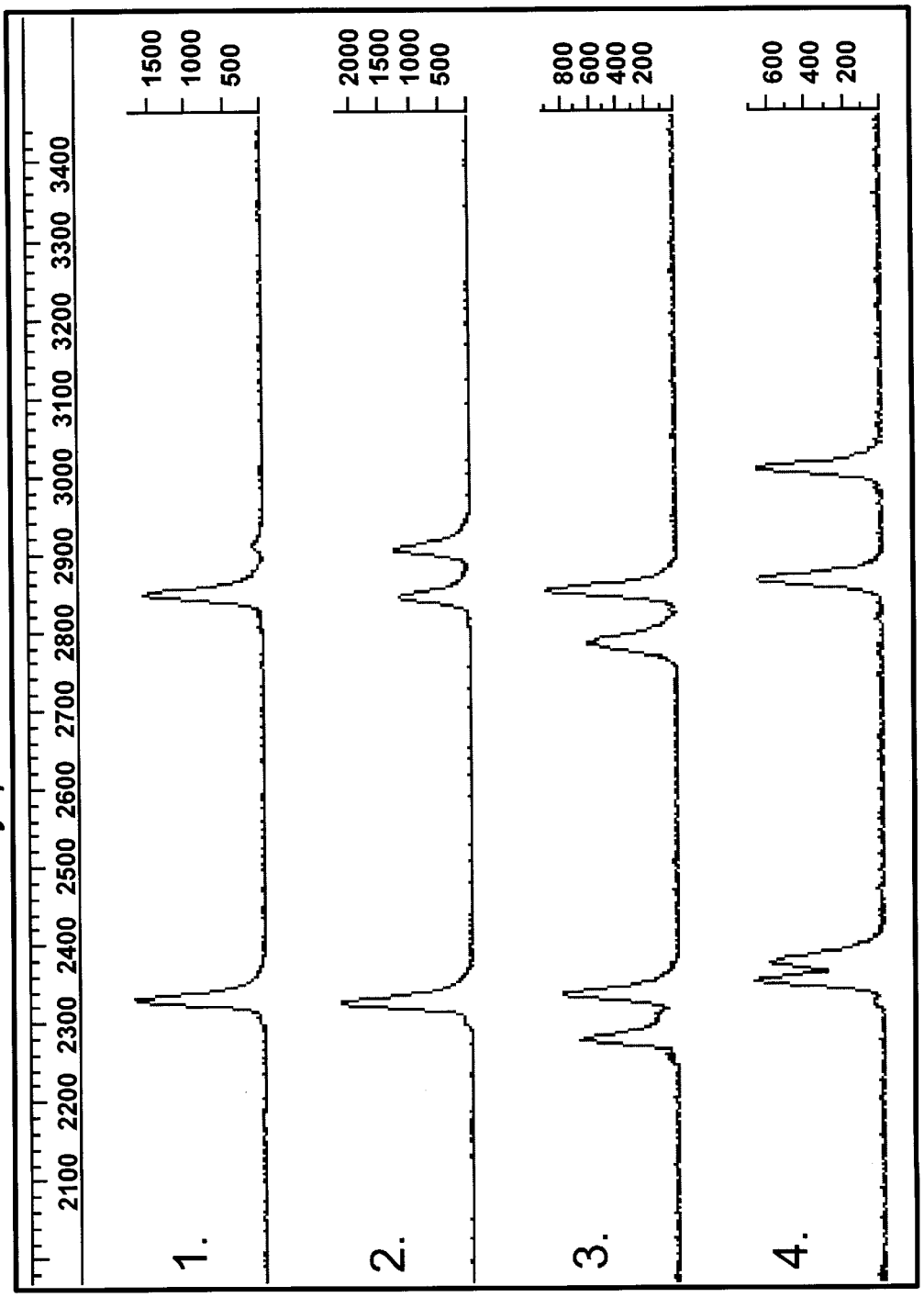
FIG. 2 presents fSSCP analysis of exon 4 open-reading-frame and splice-junction regions of the mouse Tyrp-1 gene.

The Tyrp-1 gene was chosen as a model gene to screen for induced mutations. This gene spans more than 18 kilobase-pairs (kbp) of genomic DNA, producing an RNA transcript with 8 cxons separated by 7 introns. Following splicing of the immature transcript, the mRNA contains an open reading frame that encodes a protein of 537 amino acids. Primers (Tables 6 and 7) for fSSCP were designed to test the open reading frame and splice junctions of this gene in the genomic DNA of the F1 mice. 2500 F1 mice were screened by fSSCP, which revealed aberrantly-migrating PCR products in five different mice. Three of these mutations occurred within 100 bp of one another and were detected with the same PCR primer pair; their fSSCP profiles are presented in FIG. 2. Lane 1 shows the fSSCP pattern of a normal homozygous mouse. Both alleles in this mouse have the same sequence and, consequently, generate identical PCR products; however, as the two opposing strands of these PCR products are complementary (therefore of unlike sequence), the single strands migrate with different mobilities. As the primers used to amplify both strands were labeled, two peaks are observed on the tracing. Lanes 2, 3 and 4 show fSSCP data for three different offspring of ENU mutagenized fathers, each with an independently-generated heterozygous mutation in this region of the Tyrp-1 gene. Peaks that co-migrate with those in lane 1 are from the nonmutant allele; extra peaks are the result of altered mobilities of single-strands from the mutated allele.

Sequencing confirmed that each of the five mice had a heterozvgous mutation in the open reading frame of the Tyrp-1 gene, and that all of the mutations were different. Mutations of the Tyrp-1 gene have been extensively studied, and it is known that most mutations in this gene are recessive, so that the characteristic brown phenotype is only seen when an animal carries homozygous Tyrp-1 mutations. Consistent with this, none of these heterozygous animals had an abnormal coat color. Two of the mutations are predicted not to change the sequence of the encoded protein, while three should change an amino acid within the primary protein sequence. (Table 16).

Not all DNA mutations will cause a phenotype, i.e. some DNA changes do not change the protein or otherwise affect the gene function; therefore, the phenotypically observed mutation frequency is less than the number of actual Tyrp-1 DNA mutations in the phenotypically studied mouse populations. A published study of spontaneous mutation of the Tyrp-1 locus found 3 recessive phenotype causing mutations arising in 919,699 mice tested (1 in 306,566 mice), for a phenotypic frequency of $3.3 \times 10^{-6}$ (Schlager and Dickie, 1971, *Mutation Res.*, 11: 89–96). In contrast, the SSCP study described in the present Example detected DNA mutations at a frequency of 5 in 2500 (1 in 500) among progeny of ENU-mutagenized mice for a frequency of $2.0 \times 10^{-3}$. The observed DNA mutation frequency in the ENU-treated mice is over 600 times that of the observed spontaneous phenotypic mutation frequency at this locus. Estimates of the ratio of phenotypically silent to phenotypically expressed DNA mutations range from 1:4 to 1:9. Using the higher estimate of non-phenotypic causing mutations to compare the DNA mutation frequency observed in the F1 offspring of ENU-treated mice to spontaneous phenotypic frequency (i.e. multiplying the phenotypic frequency by 10 to convert to DNA change frequency), a 61-fold increase in mutation frequency in the ENU mutagenized mice over spontaneous mutation is observed.

These data are consistent with reports of ENU inducing phenotypic mutations at a rate 87 times that of background phenotypic mutations (Russell et al., 1979, supra). Such mutagenesis, followed by large-scale mutation screening, allows the identification of a living organism carrying mutations in a gene to be studied without the need to use phenotype as a guide as to the identity of the animals carrying the mutation. Subsequent breeding of the carriers to homozygosity for the mutated gene allows a test of the effects of the mutations on the function of the encoded protein and the phenotype of the mutant animals.

USE

The invention is useful in the discovery and characterization of a gene or genes of interest, with an aim toward the development of therapeutic agents or therapeutic targets for treating human disease or for treating animal diseases. The invention is also useful for DNA mutation screening of a class or family of genes, rather than single genes. The invention provides a rapid assay for the identification of mutant genes and overcomes one of the major obstacles toward the functional analysis of gene function, i.e., the need for a phenotypic screen to identify a mutation in a gene of interest.

Screening methods of the invention are thus useful for determining the function of a gene for which a function is unknown; for determining the range of phenotypes associated with different mutations in a gene for which a function may or may not have been known; and to identify specified mutations in a gene of interest.

The invention results in the production of organisms which can be used in a number of ways for drug discovery. For example, a mouse containing a mutation in a gene of interest may provide a model for the study and treatment of the disease state; cells derived from the mutant mouse will allow in vitro assessment of drug activity; and interbreeding of a mutant mouse which each have a mutation in a gene involved in a polygenic disorder will allow investigation of gene interactions in the overall phenotype.

TABLE 2

Tyrosinase Gene SSCP Primers

| Primer Pair | Amplimer | Oligo Name | Sequencing Tail Sequence |
|---|---|---|---|
| A | cMm100 | cMm100f [SEQ ID NO: 37] | GTAAAACGACGGCCAGT |
|   | cMm100 | cMm100r [SEQ ID NO: 38] | GGAAACAGCTATGACCAT |
| B | cMm120 | cMm120f [SEQ ID NO: 39] | GTAAAACGACGGCCAGT |
|   | cMm120 | cMm120r [SEQ ID NO: 40] | GGAAACAGCTATGACCAT |
| C | cMm140 | cMm140f [SEQ ID NO: 41] | GTAAAACGACGGCCAGT |
|   | cMm140 | cMm140r [SEQ ID NO: 42] | GGAAACAGCTATGACCAT |
| D | cMm160 | cMm160f [SEQ ID NO: 43] | GTAAAACGACGGCCAGT |
|   | cMm160 | cMm160r [SEQ ID NO: 44] | GGAAACAGCTATGACCAT |
| E | cMm180 | cMm180f [SEQ ID NO: 45] | GTAAAACGACGGCCAGT |
|   | cMm180 | cMm180r [SEQ ID NO: 46] | GGAAACAGCTATGACCAT |
| F | cMm200 | cMm200f [SEQ ID NO: 47] | GTAAAACGACGGCCAGT |
|   | cMm200 | cMm200r [SEQ ID NO: 48] | GGAAACAGCTATGACCAT |
| G | cMm210 | cMm210f [SEQ ID NO: 49] | TGTAAAACGACGGCCAGT |
|   | cMm210 | cMm210r [SEQ ID NO: 50] | CAGGAAACAGCTATGACCAT |
| H | cMm220 | cMm220f [SEQ ID NO: 51] | GTAAAACGACGGCCAGT |
|   | cMm220 | cMm220r [SEQ ID NO: 52] | GGAAACAGCTATGACCAT |
| I | cMm240 | cMm240f [SEQ ID NO: 53] | GTAAAACGACGGCCAGT |
|   | cMm240 | cMm240r [SEQ ID NO: 54] | GGAAACAGCTATGACCAT |
| J | cMm260 | cMm260f [SEQ ID NO: 55] | GTAAAACGACGGCCAGT |
|   | cMm260 | cMm260r [SEQ ID NO: 56] | GGAAACAGCTATGACCAT |
| K | cMm280 | cMm280f [SEQ ID NO: 57] | GTAAAACGACGGCCAGT |
|   | cMm280 | cMm280r [SEQ ID NO: 58] | GGAAACAGCTATGACCAT |

| Primer Pair | Gene Specific Annealing Sequence | Primer Length | Primer Label Color | Gene Tm | Product Size (bp) |
|---|---|---|---|---|---|
| A | TCATTAACCTATTGGTGCAG | 37 | Yellow | 53.8 | 287 |
|   | GGAACTGAGGTCCAGATGGTG | 39 | Yellow | 58.1 |   |
| B | CTTTCAGGCAGAGGTTCCTG | 37 | Blue | 60 | 184 |
|   | GTCTCTGTACAATTTGGGCCC | 39 | Blue | 60.1 |   |
| C | AATAGGACCTGCCAGTGCTC | 37 | Green | 59.3 | 243 |
|   | GGCCTGTGGGGATGACATAGA | 39 | Green | 60.9 |   |
| D | TTGAGTGTCTCCGAAAAGAA | 37 | Blue | 56 | 306 |
|   | GCAAGAAAAGTCTGTGCCAAG | 39 | Blue | 56.1 |   |
| E | GATTTTGCCCATGAAGCACC | 37 | Green | 62.7 | 271 |
|   | GTGCATCTTACCTGCCAGGAG | 39 | Green | 61.3 |   |
| F | TCACTTTAACATCAAATTGTT | 38 | Yellow | 50.1 | 292 |
|   | GTTATATTACCTTCCAGTGTGTT | 41 | Yellow | 50.9 |   |
| G | ACATCAAATTGTTTTTCACCAG | 40 | Yellow | 56.7 | 284 |
|   | ATATTACCTTCCAGTGTGTTTCT | 43 | Yellow | 53.8 |   |
| H | TTTAATTTCCCTTTATTCAAC | 38 | Blue | 50.8 | 217 |
|   | GGTCAACCAACCTGTCCACAA | 39 | Blue | 59.4 |   |
| I | TCCTGACTCTGAGTAACCCT | 37 | Yellow | 53.8 | 259 |
|   | GTGAGCTTTACCTGACTCTTG | 39 | Yellow | 53.2 |   |
| J | TCTGTGAAAACAGCTTGATC | 37 | Blue | 53.9 | 206 |
|   | GAGGCATAGCCTACTGCTAAG | 39 | Blue | 54.2 |   |
| K | ACTGGTGGGAGCTGTTATTG | 37 | Green | 57.7 | 233 |
|   | GGAGGTAAAACCTTTCAGTCC | 39 | Green | 53 |   |

TABLE 3

Tyrosinase Gene SSCP Summary

| Exon # | Exon Size | Primer Pair | Primer Color | Amplimer Size | Primer Pair SSCP Coverage | Sequence Tested per Primer Pair | Total SSCP Coverage of ORF |
|---|---|---|---|---|---|---|---|
| 1 | 818 bp | cMm100f/r | Yellow | 287 bp | 62–248 | 186 bp | 186 bp |
| 1 | 818 bp | cMm120f/r | Blue | 184 bp | 226–384 | 153 bp | 322 bp |
| 1 | 818 bp | cMm140f/r | Green | 243 bp | 337–503 | 166 bp | 441 bp |
| 1 | 818 bp | cMm160f/r | Blue | 306 bp | 457–686 | 229 bp | 229 bp |
| 1 | 818 bp | cMm180f/r | Green | 271 bp | 676–870 | 194 bp | 808 bp |
| 2 | 213 bp | cMm200f/r | Yellow | 292 bp | 881–1085 | 204 bp | 1037 bp |
| 2 | 213 bp | cMm210f/r | Yellow | 284 bp | 881–1081 | 200 bp | 1008 bp |
| 3 | 147 bp | cMm220f/r | Blue | 217 bp | 1098–1236 | 138 bp | 1146 bp |
| 4 | 181 bp | cMm240f/r | Yellow | 259 bp | 1246–1417 | 171 bp | 1317 bp |
| 5 | 235 bp | cMm260f/r | Blue | 206 bp | 1428–1543 | 115 bp | 1432 bp |
| 5 | 235 bp | cMm280f/r | Yellow | 233 bp | 1527–1663 | 136 bp | 1568 bp |
| Open Reading Frame: | 1594 bp |   |   |   |   | Total SSCP Coverage: | 1568 bp |

TABLE 4

T Gene SSCP Primers

| Primer Pair | Amplimer | Oligo Name | Tail Sequence |
|---|---|---|---|
| A | TMm100 | TMm100f [SEQ ID NO: 59] | TGTAAAACGACGGCCAGT |
|   | TMm100 | TMm100r [SEQ ID NO: 60] | CAGGAAACAGCTATGACCAT |
| B | TMm120 | TMm120f [SEQ ID NO: 61] | TGTAAAACGACGGCCAGT |
|   | TMm120 | TMm120r [SEQ ID NO: 62] | CAGGAAACAGCTATGACCAT |
| C | TMm140 | TMm140f [SEQ ID NO: 63] | TGTAAAACGACGGCCAGT |
|   | TMm140 | TMm140r [SEQ ID NO: 64] | CAGGAAACAGCTATGACCAT |
| D | TMm160 | TMm160f [SEQ ID NO: 65] | TGTAAAACGACGGCCAGT |
|   | TMm160 | TMm160r [SEQ ID NO: 66] | CAGGAAACAGCTATGACCAT |
| E | TMm180 | TMm180f [SEQ ID NO: 67] | TGTAAAACGACGGCCAGT |
|   | TMm180 | TMm180r [SEQ ID NO: 68] | CAGGAAACAGCTATGACCAT |
| F | TMm200 | TMm200f [SEQ ID NO: 69] | TGTAAAACGACGGCCAGT |
|   | TMm200 | TMm200r [SEQ ID NO: 70] | CAGGAAACAGCTATGACCAT |
| G | TMm220 | TMm220f [SEQ ID NO: 71] | TGTAAAACGACGGCCAGT |
|   | TMm220 | TMm220r [SEQ ID NO: 72] | CAGGAAACAGCTATGACCAT |
| H | TMm240 | TMm240f [SEQ ID NO: 73] | TGTAAAACGACGGCCAGT |
|   | TMm240 | TMm240r [SEQ ID NO: 74] | CAGGAAACAGCTATGACCAT |
| I | TMm260 | TMm260f [SEQ ID NO: 75] | TGTAAAACGACGGCCAGT |
|   | TMm260 | TMm260r [SEQ ID NO: 76] | CAGGAAACAGCTATGACCAT |

| Primer Pair | Annealing Sequence | Primer Length | Gene Label Color | Tm | Product Size (bp) |
|---|---|---|---|---|---|
| A | CCGCAGAGTGACCCTTTTC | 38 | Blue | 53.7 | 250 |
|   | GTCTCCCTTCTCGCTGCC | 38 | Blue | 51.9 |   |
| B | TGGAAGGTGGAGAGGGTG | 36 | Yellow | 50 | 268 |
|   | GCCGTTCTTGGTCACAATC | 39 | Yellow | 50.1 |   |
| C | GAGGATGTTCCCGGTGCTG | 37 | Green | 64 | 164 |
|   | GGTACCCACTCCCCGTTCAC | 40 | Green | 63.8 |   |
| D | TCTTGCTGGACTTCGTGACG | 38 | Yellow | 63 | 241 |
|   | CTGTCCCCCTCCATTGAGC | 39 | Yellow | 63 |   |
| E | AAACTCCTTGCATAAGTATGAACC | 42 | Green | 50.7 | 164 |
|   | TCCTCATTCTGGTAGGCAGTC | 41 | Green | 50.8 |   |
| F | GTGGCTTGTTCCTGGTGC | 36 | Green | 50.8 | 208 |
|   | TTGGAGAGCTGTTCCGATG | 39 | Green | 50.8 |   |
| G | CCTATGCGGACAATTCATCTG | 39 | Blue | 52.2 | 157 |
|   | AGGTGGGCTGGCGTTATG | 38 | Blue | 53.2 |   |
| H | CAGTATCCCAGTCTCTGGTCTG | 40 | Yellow | 50.4 | 249 |
|   | GGCTGTCAGAAATGTCTGTGAC | 42 | Yellow | 51.2 |   |
| I | ACATTACACACCACTGACGCAC | 40 | Blue | 52.4 | 303 |
|   | TATTTTTCCCTTGTCCCAAGAG | 42 | Blue | 51.9 |   |

TABLE 5

T Gene SSCP Summary

| Exon # | Exon Size | Primer Pair | Primer Color | Amplimer Size | Primer Pair SSCP Coverage | Sequence Tested per Primer Pair | Total SSCP Coverage of ORF |
|---|---|---|---|---|---|---|---|
| 1 | 206 bp | TMm100f/r | Blue | 250 bp | 109–198 | 89 bp | 89 bp |
| 1 | 206 bp | TMm120f/r | Yellow | 268 bp | 101–293 | 192 bp | 184 bp |
| 2 | 264 bp | TMm140f/r | Green | 164 bp | 333–420 | 87 bp | 271 bp |
| 2 | 264 bp | TMm160f/r | Yellow | 241 bp | 407–560 | 153 bp | 411 bp |
| 3 | 134 bp | TMm180f/r | Green | 164 bp | 612–692 | 80 bp | 491 bp |
| 6 | 173 bp | TMm200f/r | Green | 208 bp | 861–993 | 132 bp | 623 bp |
| 7 | 129 bp | TMm220f/r | Blue | 157 bp | 1034–1113 | 79 bp | 702 bp |
| 8 | 276 bp | TMm240f/r | Yellow | 249 bp | 1166–1332 | 166 bp | 868 bp |
| 8 | 276 bp | TMm260f/r | Blue | 303 bp | 1273–1419 | 146 bp | 955 bp |
| Open Reading Frame: | 1310 bp |   |   |   |   | Total SSCP Coverage | 955 bp |

TABLE 6

Tryp-1 Gene SSCP Primers

| Primer Pair | Amplimer | Oligo Name | Sequencing Tail Sequence |
|---|---|---|---|
| A | bMm100 | bMm100f [SEQ ID NO: 77] | TGTAAAACGACGGCCAGT |
|   | bMm100 | bMm100r [SEQ ID NO: 78] | CAGGAAACAGCTATGACCAT |
| B | bMm120 | bMm120f [SEQ ID NO: 79] | TGTAAAACGACGGCCAGT |
|   | bMm120 | bMm120r [SEQ ID NO: 80] | CAGGAAACAGCTATGACCAT |
| C | bMm140 | bMm140f [SEQ ID NO: 81] | TGTAAAACGACGGCCAGT |
|   | bMm140 | bMm140r [SEQ ID NO: 82] | CAGGAAACAGCTATGACCAT |
| D | bMm160 | bMm160f [SEQ ID NO: 83] | TGTAAAACGACGGCCAGT |
|   | bMm160 | bMm160r [SEQ ID NO: 84] | CAGGAAACAGCTATGACCAT |
| E | bMm180 | bMm180f [SEQ ID NO: 85] | TGTAAAACGACGGCCAGT |
|   | bMm180 | bMm180r [SEQ ID NO: 86] | CAGGAAACAGCTATGACCAT |
| F | bMm200 | bMm200f [SEQ ID NO: 87] | TGTAAAACGACGGCCAGT |
|   | bMm200 | bMm200r [SEQ ID NO: 88] | CAGGAAACAGCTATGACCAT |
| G | bMm220 | bMm220f [SEQ ID NO: 89] | TGTAAAACGACGGCCAGT |
|   | bMm220 | bMm220r [SEQ ID NO: 90] | CAGGAAACAGCTATGACCAT |
| H | bMm240 | bMm240f [SEQ ID NO: 91] | TGTAAAACGACGGCCAGT |
|   | bMm240 | bMm240r [SEQ ID NO: 92] | CAGGAAACAGCTATGACCAT |
| I | bMm260 | bMm260f [SEQ ID NO: 93] | TGTAAAACGACGGCCAGT |
|   | bMm260 | bMm260r [SEQ ID NO: 94] | CAGGAAACAGCTATGACCAT |
| J | bMm280 | bMm280f [SEQ ID NO: 95] | TGTAAAACGACGGCCAGT |
|   | bMm280 | bMm280r [SEQ ID NO: 96] | CAGGAAACAGCTATGACCAT |

| Primer Pair | Gene Specific Annealing Sequence | Primer Length | Primer Label Color | Gene Tm | Product Size (bp) |
|---|---|---|---|---|---|
| A | TTCTCCATGCAAAGAGCAGC | 38 | Yellow | 61.6 | 304 |
|   | CAATCACAGCCACACACCTG | 40 | Yellow | 61.2 |   |
| B | GACCCTTGTGGCTCATCATC | 38 | Blue | 60.5 | 289 |
|   | TGTCTTCCCCGCCTTTCTAC | 40 | Blue | 61.5 |   |
| C | CTTTTCATGTTTAAAGTCAGG | 39 | Blue | 51.9 | 238 |
|   | CAAACAAAGTAGTTATAAACGG | 42 | Blue | 51.5 |   |
| D | TTAGAAGACATACTGGGACC | 38 | Yellow | 51.7 | 276 |
|   | ACCTAAAAACCAAGAATCAG | 40 | Yellow | 51.2 |   |
| E | ATTTCTATGATCTAGGAGATGC | 40 | Yellow | 52 | 282 |
|   | TAGTAGCTGTCATTTGGGTC | 40 | Yellow | 52.8 |   |
| F | TTCCTTTCCTCCCCAGGC | 36 | Green | 62.4 | 247 |
|   | CAAAACACCAATTTTGTTTACTTGC | 45 | Green | 61 |   |
| G | CTTTCAAATGTAGGTTACAGTG | 40 | Green | 51.9 | 253 |
|   | AAAACATAGGAAAGCATCTC | 40 | Green | 51.2 |   |
| H | GCCTTTGGAATATTTTAGAT | 38 | Blue | 50.6 | 228 |
|   | GTAAAAATACCCTGACAAAAC | 41 | Blue | 50.8 |   |
| I | TCTTATCTTTCAAATAGGTCAG | 40 | Blue | 50.8 | 216 |
|   | ATAGCGTTGATAGTGATCAG | 40 | Blue | 50.3 |   |
| J | ATTACCATTGCTGTAGTGGC | 38 | Green | 55.3 | 273 |
|   | TGTTTCAATCAGGTTGCTTC | 40 | Green | 56.3 |   |

TABLE 7

Tyrp-1 Gene SSCP Summary

| Exon # | Exon Size | Primer Pair | Primer Color | Amplimer Size | Primer Pair SSCP Coverage | Sequence Tested per Primer Pair | Total SSCP Coverage of ORF |
|---|---|---|---|---|---|---|---|
| 2 | 469 bp | cMm100f/r | Yellow | 304 bp | 175–362 | 187 bp | 187 bp |
| 2 | 496 bp | cMm120f/r | Blue | 289 bp | 354–559 | 205 bp | 384 bp |
| 3 | 322 bp | cMm140f/r | Blue | 238 bp | 565–731 | 166 bp | 556 bp |
| 3 | 322 bp | cMm160f/r | Yellow | 276 bp | 690–882 | 192 bp | 707 bp |
| 4 | 204 bp | cMm180f/r | Yellow | 282 bp | 890–1087 | 197 bp | 904 bp |
| 5 | 167 bp | cMm200f/r | Green | 247 bp | 1088–1255 | 167 bp | 1071 bp |
| 6 | 179 bp | cMm220f/r | Green | 253 bp | 1265–1435 | 170 bp | 1241 bp |
| 7 | 146 bp | cMm240f/r | Blue | 228 bp | 1438–1582 | 144 bp | 1385 bp |
| 8 | 205 bp | cMm260f/r | Blue | 216 bp | 1588–1720 | 132 bp | 1517 bp |
| 8 | 205 bp | cMm280f/r | Green | 273 bp | 1629–1786 | 194 bp | 1583 bp |
| Open Reading Frame: | 1613 bp |   |   |   |   | Total SSCP Coverage: | 1583 bp |

TABLE 8

Sry Gene SSCP Primers

| Pair | Amplimer | Oligo Name | Sequencing Tail Sequence |
|---|---|---|---|
| A | SryMm100 | SryMm100f [SEQ ID NO; 97] | TGTAAAACGACGGCCAGT |
|   | SryMm100 | SryMm100r [SEQ ID NO: 98] | CAGGAAACAGCTATGACCAT |
| B | SryMm120 | SryMm120f [SEQ ID NO: 99] | TGTAAAACGACGGCCAGT |
|   | SryMm120 | SryMm120r [SEQ ID NO: 100] | CAGGAAACAGCTATGACCAT |
| C | SryMm140 | SryMm140f [SEQ ID NO: 101] | TGTAAAACGACGGCCAGT |
|   | SryMm140 | SryMm140r [SEQ ID NO: 102] | CAGGAAACAGCTATGACCAT |
| D | SryMm160 | SryMm160f [SEQ ID NO: 103] | TGTAAAACGACGGCCAGT |
|   | SryMm160 | SryMm160r [SEQ ID NO: 104] | CAGGAAACAGCTATGACCAT |
| E | SryMm180 | SryMm180f [SEQ ID NO: 105] | TGTAAAACGACGGCCAGT |
|   | SryMm180 | SryMm180r [SEQ ID NO: 106] | CAGGAAACAGCTATGACCAT |
| F | SryMm200 | SryMm200f [SEQ ID NO: 107] | TGTAAAACGACGGCCAGT |
|   | SryMm200 | SryMm200r [SEQ ID NO: 108] | CAGGAAACAGCTATGACCAT |
| G | SryMm220 | SryMm220f [SEQ ID NO: 109] | TGTAAAACGACGGCCAGT |
|   | SryMm220 | SryMm220r [SEQ ID NO: 110] | CAGGAAACAGCTATGACCAT |
| H | SryMm240 | SryMm240f [SEQ ID NO: 111] | TGTAAAACGACGGCCAGT |
|   | SryMm240 | SryMm240r [SEQ ID NO: 112] | CAGGAAACAGCTATGACCAT |
| I | SryMm260 | SryMm260f [SEQ ID NO: 113] | TGTAAAACGACGGCCAGT |
|   | SryMm260 | SryMm260r [SEQ ID NO: 114] | CAGGAAACAGCTATGACCAT |

| Pair | Gene Specific Annealing Sequence | Primer Length | Primer Color Label Color | Gene Tm | Product Size (bp) |
|---|---|---|---|---|---|
| A | CAAGTTTTGGGACTGGTGAC | 38 | Blue | 58.0 | 220 |
|   | GGCTTCTGTAAGGCTTTTCC | 40 | Blue | 58.1 |  |
| B | CAAGTTGGCCCAGCAGAATC | 38 | Yellow | 63.0 | 263 |
|   | GTTGAGGCAACTGCAGGCTG | 40 | Yellow | 64.4 |  |
| C | GAGGGCTAAAGTGTCACAGAGGAG | 42 | Yellow | 62.8 | 304 |
|   | CATAGAACTGCTGTTGCTGCTGG | 43 | Yellow | 64.4 |  |
| D | CAGCAGCAGCAGTTCCATAACC | 40 | Blue | 64.4 | 223 |
|   | GCTCCTGGTGGTGGTGGTG | 39 | Blue | 65.1 |  |
| E | CAGCAGAAGCAGCAGTTT | 36 | Green | 55.2 | 248 |
|   | TTGGTGGTGGTGGTGGTC | 38 | Green | 61.3 |  |
| F | ACCACCACCACCAGGAGC | 36 | Green | 62.1 | 261 |
|   | TGATGCTGCTGCTGCTGG | 38 | Green | 63.6 |  |
| G | CACCACCACCACCAAC | 34 | Blue | 54.3 | 180 |
|   | GTTGCTGCTGGGGGTG | 36 | Blue | 59.7 |  |
| H | CATCAGTTCCATGACCACCC | 38 | Green | 61.2 | 243 |
|   | GGTCATGGAACTGCTGTTGC | 40 | Green | 61.7 |  |
| I | GAAGCAGCAGTTCCATGACC | 38 | Yellow | 60.8 | 282 |
|   | CATAGCAAGGGGGAGTGTTG | 40 | Yellow | 60.5 |  |

TABLE 9

Sry Gene SSCP Summary

| Exon # | Exon Size | Primer Pair | Primer Color | Amplimer Size | Primer Pair SSCP Coverage | Sequence Tested per Primer Pair | Total SSCP Coverage of ORF |
|---|---|---|---|---|---|---|---|
| 1 | 1187 bp | sryMm100f/r | Blue | 220 bp | 51–177 | 126 bp | 126 bp |
| 1 | 1187 bp | sryMm120f/r | Yellow | 263 bp | 133–317 | 184 bp | 266 bp |
| 1 | 1187 bp | sryMm140f/r | Yellow | 304 bp | 308–526 | 218 bp | 475 bp |
| 1 | 1187 bp | sryMm160f/r | Blue | 223 bp | 500–665 | 165 bp | 614 bp |
| 1 | 1187 bp | sryMm180f/r | Green | 248 bp | 628–800 | 172 bp | 749 bp |
| 1 | 1187 bp | sryMm200f/r | Green | 261 bp | 685–870 | 185 bp | 819 bp |
| 1 | 1187 bp | sryMm220f/r | Blue | 180 bp | 820–929 | 109 bp | 878 bp |
| 1 | 1187 bp | sryMm240f/r | Green | 243 bp | 903–1069 | 166 bp | 1018 bp |
| 1 | 1187 bp | sryMm260f/r | Yellow | 282 bp | 1060–1238 | 178 bp | 1187 bp |
| Open Reading Frame: | 1187 bp |  |  |  |  | Total SSCP Coverage: | 1187 bp |

TABLE 10

MGF Gene SSCP Primers

| Primer Pair | Amplimer | Oligo Name | Sequencing Tail Sequence |
|---|---|---|---|
| A | MgfMm100 | MgfMm100f [SEQ ID NO: 115] | TGTAAAACGACGGCCAGT |
|   | MgfMm100 | MgfMm100r [SEQ ID NO: 116] | CAGGAAACAGCTATGACCAT |
| B | MgfMm120 | MgfMm120f [SEQ ID NO: 117] | TGTAAAACGACGGCCAGT |
|   | MgfMm120 | MgfMm120r [SEQ ID NO: 118] | CAGGAAACAGCTATGACCAT |
| C | MgfMm140 | MgfMm140f [SEQ ID NO: 119] | TGTAAAACGACGGCCAGT |
|   | MgfMm140 | MgfMm140r [SEQ ID NO: 120] | CAGGAAACAGCTATGACCAT |
| D | MgfMm160 | MgfMm160f [SEQ ID NO: 121] | TGTAAAACGACGGCCAGT |
|   | MgfMm160 | MgfMm160r [SEQ ID NO: 122] | CAGGAAACAGCTATGACCAT |
| E | MgfMm180 | MgfMm180f [SEQ ID NO: 123] | TGTAAAACGACGGCCAGT |
|   | MgfMm180 | MgfMm180r [SEQ ID NO: 124] | CAGGAAACAGCTATGACCAT |

| Primer Pair | Gene Specific Annealing Sequence | Primer Length | Primer Label Color | Gene Tm | Product Size (bp) |
|---|---|---|---|---|---|
| A | CTTCATTTGCTGTCTGTCAC | 38 | Yellow | 54.2 | 246 |
|   | TTGTGTCTTCTTCATAAGGAAAG | 43 | Yellow | 55.5 |   |
| B | ACTTGGATTATCACTTGCAT | 38 | Blue | 52.2 | 152 |
|   | CAGTTTTGTAATGTCTTTTACAT | 43 | Blue | 50.9 |   |
| C | CCTAGTCATTGTTGGCTACGAG | 40 | Blue | 58.9 | 209 |
|   | CTTCGGTGCGTTTTCTTCC | 39 | Blue | 60.8 |   |
| D | AATATAAAAGAATCTCCGAAGAG | 41 | Green | 53.2 | 195 |
|   | CTTTCTCGGGACCTAATG | 38 | Green | 53.1 |   |
| E | GGAAAGCCGCAAAGGCCC | 36 | Blue | 67.3 | 148 |
|   | CTTCCAGTATAAGGCTCCAAAAGC | 44 | Blue | 61.7 |   |

TABLE 11

MGF Gene SSCP Summary

| Exon # | Exon Size | Primer Pair | Primer Color | Amplimer Size | Primer Pair SSCP Coverage | Sequence Tested per Primer Pair | Total SSCP Coverage of ORF |
|---|---|---|---|---|---|---|---|
| 1 | 14 bp | mgfMm100f/r | Yellow | 246 bp | (all 5'UTR) | 0 | 0 bp |
| 2 | 114 bp | mgfMm120f/r | Blue | 152 bp | 233–305 | 72 bp | 72 bp |
| 4 | 171 bp | mgfMm140f/r | Blue | 209 bp | 412–541 | 129 bp | 201 bp |
| 5 | 157 bp | mgfMm160f/r | Green | 195 bp | 584–699 | 115 bp | 316 bp |
| 7 | 110 bp | mgfMm180f/r | Blue | 148 bp | 820–882 | 62 bp | 378 bp |
| Open Reading Frame: | 821 bp |   |   |   |   | Total SSCP Coverage: | 378 bp |

TABLE 12 c-kit Gene SSCP Primers

| Primer Pair | Amplimer | Oligo Name | Sequencing Tail Sequence |
|---|---|---|---|
| A | cKitMm100 | cKitMm100f [SEQ ID NO: 125] | TGTAAAACGACGGCCAGT |
|   | cKitMm100 | cKitMm100r [SEQ ID NO: 126] | CAGGAAACAGCTATGACCAT |
| B | cKitMm120 | cKitMm120f [SEQ ID NO: 127] | TGTAAAACGACGGCCAGT |
|   | cKitMm120 | cKitMm120r [SEQ ID NO: 128] | CAGGAAACAGCTATGACCAT |
| C | cKitMm140 | cKitMm140f [SEQ ID NO: 129] | TGTAAAACGACGGCCAGT |
|   | cKitMm140 | cKitMm140r [SEQ ID NO: 130] | CAGGAAACAGCTATGACCAT |
| D | cKitMm160 | cKitMm160f [SEQ ID NO: 131] | TGTAAAACGACGGCCAGT |
|   | cKitMm160 | cKitMm160r [SEQ ID NO: 132] | CAGGAAACAGCTATGACCAT |
| E | cKitMm180 | cKitMm180f [SEQ ID NO: 133] | TGTAAAACGACGGCCAGT |
|   | cKitMm180 | cKitMm180r [SEQ ID NO: 134] | CAGGAAACAGCTATGACCAT |
| F | cKitMm200 | cKitMm200f [SEQ ID NO: 135] | TGTAAAACGACGGCCAGT |
|   | cKitMm200 | cKitMm200r [SEQ ID NO: 136] | CAGGAAACAGCTATGACCAT |
| G | cKitMm220 | cKitMm220f [SEQ ID NO: 137] | TGTAAAACGACGGCCAGT |
|   | cKitMm220 | cKitMm220r [SEQ ID NO: 138] | CAGGAAACAGCTATGACCAT |
| H | cKitMm240 | cKitMm240f [SEQ ID NO: 139] | TGTAAAACGACGGCCAGT |
|   | cKitMm240 | cKitMm240r [SEQ ID NO: 140] | CAGGAAACAGCTATGACCAT |
| I | cKitMm260 | cKitMm260f [SEQ ID NO: 141] | TGTAAAACGACGGCCAGT |
|   | cKitMm260 | cKitMm260r [SEQ ID NO: 142] | CAGGAAACAGCTATGACCAT |
| J | cKitMm280 | cKitMm280f [SEQ ID NO: 143] | TGTAAAACGACGGCCAGT |
|   | cKitMm280 | cKitMm280r [SEQ ID NO: 144] | CAGGAAACAGCTATGACCAT |
| K | cKitMm300 | cKitMm300f [SEQ ID NO: 145] | TGTAAAACGACGGCCAGT |

TABLE 12-continued c-kit Gene SSCP Primers

| | | | |
|---|---|---|---|
| | cKitMm300 | cKitMm300r [SEQ ID NO: 146] | CAGGAAACAGCTATGACCAT |
| L | cKitMm320 | cKitMm320f [SEQ ID NO: 147] | TGTAAAACGACGGCCAGT |
| | cKitMm320 | cKitMm320r [SEQ ID NO: 148] | CAGGAAACAGCTATGACCAT |

| Primer Pair | Gene Specific Annealing Sequence | Primer Length | Primer Label Color | Gene Tm | Product Size (bp) |
|---|---|---|---|---|---|
| A | CCACGTCTCAGCCATCTG | 36 | Blue | 58.5 | 311 |
|   | CTCTAACAAACACGTAAATAGAACTC | 46 | Blue | 55.1 | |
| B | ATCCTGCCAAACTTTTCCTG | 38 | Blue | 59.2 | 146 |
|   | TGAGGGAATAATTGGACACC | 40 | Blue | 57.3 | |
| C | AAGAAGACAGCGACGCGCTG | 38 | Blue | 66.3 | 278 |
|   | CTTCCCGCACTTTGAGGGTG | 40 | Blue | 65.2 | |
| D | CCATCAAGGCTATCCCTG | 36 | Green | 56.5 | 175 |
|   | CTGAGGGTTCATCTTTAGCC | 40 | Green | 56.5 | |
| E | CCTCAGCACATAGCCCAG | 36 | Yellow | 57.9 | 213 |
|   | CTACTACTTTCAAGGTTGTTGTGAC | 45 | Yellow | 56.4 | |
| F | AAAAAGGATTCATCAACATC | 38 | Yellow | 51.6 | 228 |
|   | CTGATGTTGCTTTTGTTATC | 40 | Yellow | 50.9 | |
| G | GTGTACCACTCCTGTCTCAC | 38 | Yellow | 52.7 | 220 |
|   | CTTTAAATGCAAAGTTAAAGAAG | 43 | Yellow | 52.7 | |
| H | AAACCCATGTATGAAGTACAATGG | 42 | Green | 59.1 | 192 |
|   | CGAAGGCACCAGCTCCC | 37 | Green | 63 | |
| I | GGCCCACCCTGGTCATTAC | 37 | Green | 62.5 | 189 |
|   | CAGGAAGGCTCCGTTGAGTG | 40 | Green | 63.3 | |
| J | ACTCGTACATAGAAAGAGACGTGAC | 43 | Blue | 58.1 | 166 |
|   | ATTCTTGGAGGCGAGGAAC | 39 | Blue | 59.2 | |
| K | TGTATTCACAGAGATTTGGC | 38 | Blue | 53.7 | 161 |
|   | ATTTCCTTTGACCACGTAAT | 40 | Blue | 53.8 | |
| L | ATTACTCCAACTTGGCAAACTG | 41 | Blue | 59.6 | 278 |
|   | CGCTACCCTGGAATAGGATGC | 40 | Blue | 58.6 | |

TABLE 13 c-kit Gene SSCP Summary

| Exon # | Exon Size | Primer Pair | Primer Color | Amplimer Size | Primer Pair SSCP Coverage | Sequence Tested per Primer Pair | Total SSCP Coverage of ORF |
|---|---|---|---|---|---|---|---|
| 2 | 270 pb | kitMm100f/r | Blue | 311 bp | 89–335 | 246 bp | 246 bp |
| 3 | 282 bp | kitMm120f/r | Blue | 146 bp | 382–449 | 67 bp | 313 bp |
| 3 | 282 bp | kitMm140f/r | Blue | 278 bp | 424–623 | 199 bp | 487 bp |
| 4 | 137 bp | kitMm160f/r | Green | 175 bp | 662–760 | 98 bp | 585 bp |
| 5 | 169 bp | kitMm180f/r | Yellow | 213 bp | 799–930 | 131 bp | 716 bp |
| 6 | 190 bp | kitMm200f/r | Yellow | 228 bp | 976–1125 | 149 bp | 865 bp |
| 9 | 194 bp | kitMm220f/r | Yellow | 220 bp | 1397–1535 | 138 bp | 1003 bp |
| 11 | 127 bp | kitMm240f/r | Green | 192 bp | 1690–1801 | 111 bp | 1114 bp |
| 14 | 151 bp | kitMm260f/r | Green | 189 bp | 2028–2139 | 111 bp | 1225 bp |
| 16 | 128 bp | kitMm280f/r | Blue | 166 bp | 2274–2357 | 83 bp | 1308 bp |
| 17 | 123 bp | kitMm300f/r | Blue | 161 bp | 2397–2479 | 82 bp | 1390 bp |
| 21 | 130 bp | kitMm320f/r | Blue | 278 bp | 2841–2949 | 108 bp | 1498 bp |
| Open Reading Frame: | 2927 bp | | | | | Total SSCP Coverage: | 1498 bp |

TABLE 14

Pax-6 gene SSCP primers

| Primer Pair | Amplimer | Oligo Name | Sequencing Tail Sequence |
|---|---|---|---|
| A | Pax6Mm121 | Pax6Mm121f [SEQ ID NO: 149] | TGTAAAACGACGGCCAGT |
|   | Pax6Mm121 | Pax6Mm121r [SEQ ID NO: 150] | CAGGAAACAGCTATGACCAT |
| B | Pax6Mm161 | Pax6Mm161f [SEQ ID NO: 151] | TGTAAAACGACGGCCAGT |
|   | Pax6Mm161 | Pax6Mm161r [SEQ ID NO: 152] | CAGGAAACAGCTATGACCAT |
| C | Pax6Mm180 | Pax6Mm180f [SEQ ID NO: 153] | TGTAAAACGACGGCCAGT |
|   | Pax6Mm180 | Pax6Mm180r [SEQ ID NO: 154] | CAGGAAACAGCTATGACCAT |
| D | Pax6Mm200 | Pax6Mm200f [SEQ ID NO: 155] | TGTAAAACGACGGCCAGT |
|   | Pax6Mm200 | Pax6Mm200r [SEQ ID NO: 156] | CAGGAAACAGCTATGACCAT |
| E | Pax6Mm220 | Pax6Mm220f [SEQ ID NO: 157] | TGTAAAACGACGGCCAGT |
|   | Pax6Mm220 | Pax6Mm220r [SEQ ID NO: 158] | CAGGAAACAGCTATGACCAT |

TABLE 14-continued

Pax-6 gene SSCP primers

| | | | |
|---|---|---|---|
| F | Pax6Mm240 | Pax6Mm240f [SEQ ID NO: 159] | TGTAAAACGACGGCCAGT |
| | Pax6Mm240 | Pax6Mm240r [SEQ ID NO: 160] | CAGGAAACAGCTATGACCAT |
| G | Pax6Mm260 | Pax6Mm260f [SEQ ID NO: 161] | TGTAAAACGACGGCCAGT |
| | Pax6Mm260 | Pax6Mm260r [SEQ ID NO: 162] | CAGGAAACAGCTATGACCAT |

| Primer Pair | Gene Specific Annealing Sequence | Primer Length | Primer Label Color | Gene Tm | Product Size (bp) |
|---|---|---|---|---|---|
| A | GTCACAGCGGAGTGAATCAG | 38 | Blue | 59.4 | 168 bp |
| | TGCAGAATTCGGGAAATGTC | 40 | Blue | 61 | |
| B | GTATCCAACGGTTGTGTGAG | 38 | Yellow | 56.4 | 254 bp |
| | ACTGGGTATGTTATCGTTGG | 40 | Yellow | 55 | |
| C | GTGTCATCAATAAACAGAGTTCTTC | 43 | Yellow | 56.2 | 200 bp |
| | CGTGGGTTGCCCTGGTAC | 38 | Yellow | 62.4 | |
| D | ATGGCTGCCAGCAACAGG | 36 | Green | 63.4 | 197 bp |
| | CTTTCTCCAGAGCCTCAATCTGC | 43 | Green | 63.9 | |
| E | GTATGGTTTTCTAATCGAAGGGC | 41 | Green | 60.2 | 189 bp |
| | CAGGTGTGGTGGGCTGTG | 38 | Green | 62.3 | |
| F | CCCCCAGTCCCCAGTCAG | 36 | Blue | 64 | 189 bp |
| | CTGTTGAAGTGGTCCCCGAG | 40 | Blue | 63 | |
| G | GACTCATTTCACCTGGAGTG | 38 | Blue | 55.5 | 297 bp |
| | AAGGTCCTTGGTTCTAGTCC | 40 | Blue | 54.9 | |

TABLE 15

Pax-6 Gene SSCP Summary

| Exon # | Exon Size | Primer Pair | Primer Color | Amplimer Size | Primer Pair SSCP Coverage | Sequence Tested per Primer Pair | Total SSCP Coverage of ORF |
|---|---|---|---|---|---|---|---|
| 5 | 130 bp | paxMm100f/r | Blue | 168 pb | 191–282 | 91 bp | 91 pb |
| 6 | 215 bp | paxMm120f/r | Yellow | 254 bp | 366–541 | 175 bp | 266 bp |
| 7 | 165 bp | paxMm140f/r | Yellow | 200 bp | 587–705 | 118 bp | 384 bp |
| 8 | 158 bp | paxMm160f/r | Green | 197 bp | 746–863 | 117 bp | 501 bp |
| 10 | 150 bp | paxMm180f/r | Green | 189 bp | 993–1102 | 109 bp | 610 bp |
| 12 | 150 bp | paxMm200f/r | Blue | 189 bp | 1255–1367 | 112 bp | 722 bp |
| 13 | 85 bp | PaxMm220f/r | Blue | 297 bp | 1407–1473 | 66 bp | 788 bp |
| Open Reading Frame: | 2098 bp | | | | | Total SSCP Coverage: | 788 bp |

TABLE 16

| amplimer | sex | ENU dose mg/kg | base change | Open Reading Frame position nucleotide | amino acid | Effect on protein sequence |
|---|---|---|---|---|---|---|
| bMm240 | Female | 160 | A > T | 1301 | 434 | CAT His to CTT Leu |
| bMm240 | Female | 160 | A > G | 1395 | 465 | GAA Glu to GAG Glu (silent) |
| bMm240 | Female | 80 | C > T | 1347 | 449 | AAC Asn to AAT Asn (silent) |
| bMm220 | Male | 160 | A > T | 1175 | 392 | CAT His to CTT Leu |
| bMm200 | Male | 160 | T > C | 998 | 333 | GTC Val to GCC Ala |

OTHER EMBODIMENTS

Other embodiments will be evident to those of skill in the art. It should be understood that the foregoing detailed description is provided for clarity only and is merely exemplary. The spirit and scope of the present invention are not limited to the above examples, but are encompassed by the following claims.

I claim:

1. A method of identifying a mutation in a gene of interest in a tissue, comprising
mutagenizing an ES cell to produce a mutated ES cell; and
testing DNA from said mutated ES cell for a mutation in said gene of interest without the prior observation of a phenotypic alteration in said mutated ES cell.

2. A method of identifying a mutation in a gene of interest in a tissue, comprising
mutagenizing plural ES cells to produce a plurality of mutated ES cells; and
testing a DNA sample from each said mutated ES cell or a DNA sample comprising DNA from a plurality of mutated ES cells for a mutation in said gene of interest without the prior observation of a phenotypic alteration in said mutated ES cell.

3. The method of claim 1 or 2 wherein said testing step includes PCR amplification and fSSCP analysis using a pair of PCR primers from a region of said gene of interest.

4. The method of claim 1 or 2, further comprising the steps of:
transferring said mutated ES cell to a developing embryo of the same organism species from which said ES cell is derived; and
permitting said embryo to develop into a newborn organism.

* * * * *

SEQUENCE LISTING (1) GENERAL INFORMATION:

(iii) NUMBER OF SEQUENCES: 162

(2) INFORMATION FOR SEQ ID NO: 1:

(i) SEQUENCE CHARACTERISTICS:
      (A) LENGTH: 18 bases
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO: 1:

GCACCTCCTT CCCGCCCC                                                                 18

(2) INFORMATION FOR SEQ ID NO: 2:

(i) SEQUENCE CHARACTERISTICS:
      (A) LENGTH: 18 bases
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO: 2:

TTCGCGCCCC CGCTGCCC                                                                 18

(2) INFORMATION FOR SEQ ID NO: 3:

(i) SEQUENCE CHARACTERISTICS:
      (A) LENGTH: 18 bases
      (B) TYPE:  nucleic acid
      (C) STRANDEDNESS: single
      (D) TOPOLOGY: linear (ii) MOLECULE TYPE: other nucleic acid (xi) SEQUENCE DESCRIPTION: SEQ ID NO: 3:

GAGTGGCGCG AACCCAGC                                                                 18

(2) INFORMATION FOR SEQ ID NO: 4:

(i) SEQUENCE CHARACTERISTICS:
      (A) LENGTH: 18 bases
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO: 4:

TTGGGGTTCT CCAGGGCC                                                                 18

(2) INFORMATION FOR SEQ ID NO: 5:

(i) SEQUENCE CHARACTERISTICS:
      (A) LENGTH: 18 bases
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO: 5:

```
GAACGCGTTC ATGGTGTG                                                          18

(2) INFORMATION FOR SEQ ID NO: 6:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 6:

TACTCCTTCA TGTGCACC                                                          18

(2) INFORMATION FOR SEQ ID NO: 7:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 7:

GGAGAAGCGG CCGTTCAT                                                          18

(2) INFORMATION FOR SEQ ID NO: 8:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 8:

GCGGCGGCGA CGGCGGCG                                                          18

(2) INFORMATION FOR SEQ ID NO: 9:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 9:

CTCGCTGCCC GGCGGCCT                                                          18

(2) INFORMATION FOR SEQ ID NO: 10:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 10:

GGCTGCGCGT AGCCCAGC                                                          18

(2) INFORMATION FOR SEQ ID NO: 11:
```

-continued (i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 11:

GAACGGCTGG GCCAACGG                                                    18

(2) INFORMATION FOR SEQ ID NO: 12:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 12:

GCGGCGTTCA TGTAGCTC                                                    18

(2) INFORMATION FOR SEQ ID NO: 13:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 13:

GGCCGGCCTG CAGTACAG                                                    18

(2) INFORMATION FOR SEQ ID NO: 14:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 14:

GCGGCGGCGG CGGCGGCC                                                    18

(2) INFORMATION FOR SEQ ID NO: 15:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 15:

CGCCGCCGCC TACGGGCA                                                    18

(2) INFORMATION FOR SEQ ID NO: 16:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 16:

TACATGCTGA TCATGTCG                                                        18

(2) INFORMATION FOR SEQ ID NO: 17:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 17:

CATCCGTTCG CACTCGCA                                                        18

(2) INFORMATION FOR SEQ ID NO: 18:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 18:

TCAGATGTGG GTCAGCGG                                                        18

(2) INFORMATION FOR SEQ ID NO: 19:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 19:

CCACAGTCCC GGCCGGGC                                                        18

(2) INFORMATION FOR SEQ ID NO: 20:

(i) SEQUENCE CHARACTERISTICS:
        (A) LENGTH: 18 bases
        (B) TYPE: nucleic acid
        (C) STRANDEDNESS: single
        (D) TOPOLOGY: linear (xi) SEQUENCE DESCRIPTION: SEQ ID NO: 20:

GGGCTGTTCT TCTGGTTG                                                        18

(2) INFORMATION FOR SEQ ID NO: 21:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 21:

CGGCGGCGGA GGAGGCAA                                                        18

(2) INFORMATION FOR SEQ ID NO: 22:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 22:

TCCGCGCCCA GGCGCTTG                                    18

(2) INFORMATION FOR SEQ ID NO: 23:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 23:

GATGGCCCAG GAGAACCC                                  18

(2) INFORMATION FOR SEQ ID NO: 24:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 24:

GTCTTGGTTT TCCGCCGC                                    18

(2) INFORMATION FOR SEQ ID NO:25:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:25:

CGCTCTGCAC ATGAAGGA                                    18

(2) INFORMATION FOR SEQ ID NO:26:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:26:

CTGTCCATGC GCTGGTTC                                    18

(2) INFORMATION FOR SEQ ID NO:27:

(i) SEQUENCE CHARACTERISTICS:
        (A) LENGTH: 18 bases (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:27:

GGCGAGCGGG GTTGGGGT                                                      18

(2) INFORMATION FOR SEQ ID NO:28:

(i) SEQUENCE CHARACTERISTICS:
            (A) LENGTH: 18 bases
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:28:

CGGTGCATCG GTTGCATC                                                      18

(2) INFORMATION FOR SEQ ID NO:29:

(i) SEQUENCE CHARACTERISTICS:
            (A) LENGTH: 18 bases
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:29:

CTACCCGCAG CACCCGGG                                                      18

(2) INFORMATION FOR SEQ ID NO:30:

(i) SEQUENCE CHARACTERISTICS:
            (A) LENGTH: 18 bases
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:30:

GAGCCCAGCG CCATACCG                                                      18

(2) INFORMATION FOR SEQ ID NO:31:

(i) SEQUENCE CHARACTERISTICS:
            (A) LENGTH: 18 bases
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:31:

CTCGCCCACC TACAGCAT                                                      18

(2) INFORMATION FOR SEQ ID NO:32:

(i) SEQUENCE CHARACTERISTICS:
            (A) LENGTH: 18 bases
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:32:

GGGAGGTACA TGCTGATC                                                            18

(2) INFORMATION FOR SEQ ID NO:33:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:33:

CCACTCCAGG GCGCCCTG                                                            18

(2) INFORMATION FOR SEQ ID NO:34:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:34:

CCTCACATGT GCGACAGG                                                            18

(2) INFORMATION FOR SEQ ID NO:35:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:35:

GTGCGGCCCG GTGCCCGG                                                            18

(2) INFORMATION FOR SEQ ID NO:36:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:36:

AACCACCAAA AAAAGGAA                                                            18

(2) INFORMATION FOR SEQ ID NO:37:

(i) SEQUENCE CHARACTERISTICS:
        (A) LENGTH: 37 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer cMm100f (xi) SEQUENCE DESCRIPTION: SEQ ID NO:37:

```
GTAAAACGAC GGCCAGTTCA TTAACCTATT GGTGCAG                              37

(2) INFORMATION FOR SEQ ID NO:38:

(i) SEQUENCE CHARACTERISTICS:
        (A) LENGTH: 39 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer cMm100r (xi) SEQUENCE DESCRIPTION: SEQ ID NO:38:

GGAAACAGCT ATGACCATGG AACTGAGGTC CAGATGGTG                            39

(2) INFORMATION FOR SEQ ID NO:39:

(i) SEQUENCE CHARACTERISTICS:
        (A) LENGTH: 37 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer cMm120f (xi) SEQUENCE DESCRIPTION: SEQ ID NO:39:

GTAAAACGAC GGCCAGTCTT TCAGGCAGAG GTTCCTG                              37

(2) INFORMATION FOR SEQ ID NO:40:

(i) SEQUENCE CHARACTERISTICS:
        (A) LENGTH: 39
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer cMm120r (xi) SEQUENCE DESCRIPTION: SEQ ID NO:40:

GGAAACAGCT ATGACCATGT CTCTGTACAA TTTGGGCCC                            39

(2) INFORMATION FOR SEQ ID NO:41:

(i) SEQUENCE CHARACTERISTICS:
        (A) LENGTH: 37 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer cMm140f (xi) SEQUENCE DESCRIPTION: SEQ ID NO:41:

GTAAAACGAC GGCCAGTAAT AGGACCTGCC AGTGCTC                              37

(2) INFORMATION FOR SEQ ID NO:42:

(i) SEQUENCE CHARACTERISTICS:
        (A) LENGTH: 39 bases
```

-continued (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer cMm140r (xi) SEQUENCE DESCRIPTION: SEQ ID NO:42:

GGAAACAGCT ATGACCATGG CCTGTGGGGA TGACATAGA                39

(2) INFORMATION FOR SEQ ID NO:43:

(i) SEQUENCE CHARACTERISTICS:
        (A) LENGTH: 37 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer cMm160f (xi) SEQUENCE DESCRIPTION: SEQ ID NO:43:

GTAAAACGAC GGCCAGTTTG AGTGTCTCCG AAAAGAA                  37

(2) INFORMATION FOR SEQ ID NO:44:

(i) SEQUENCE CHARACTERISTICS:
        (A) LENGTH: 39 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer cMm160r (xi) SEQUENCE DESCRIPTION: SEQ ID NO:44:

GGAAACAGCT ATGACCATGC AAGAAAAGTC TGTGCCAAG                39

(2) INFORMATION FOR SEQ ID NO:45:

(i) SEQUENCE CHARACTERISTICS:
        (A) LENGTH: 37 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer cMm180f (xi) SEQUENCE DESCRIPTION: SEQ ID NO:45:

GTAAAACGAC GGCCAGTGAT TTTGCCCATG AAGCACC                  37

(2) INFORMATION FOR SEQ ID NO:46:

(i) SEQUENCE CHARACTERISTICS:
        (A) LENGTH: 39 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer cMm180r (xi) SEQUENCE DESCRIPTION: SEQ ID NO:46:

GGAAACAGCT ATGACCATGT GCATCTTACC TGCCAGGAG                    39

(2) INFORMATION FOR SEQ ID NO:47:

(i) SEQUENCE CHARACTERISTICS:
        (A) LENGTH: 38 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer cMm200f (xi) SEQUENCE DESCRIPTION: SEQ ID NO:47:

GTAAAACGAC GGCCAGTTCA CTTTAACATC AAATTGTT                     38

(2) INFORMATION FOR SEQ ID NO:48:

(i) SEQUENCE CHARACTERISTICS:
        (A) LENGTH: 41 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer cMm200r (xi) SEQUENCE DESCRIPTION: SEQ ID NO:48:

GGAAACAGCT ATGACCATGT TATATTACCT TCCAGTGTGT T                 41

(2) INFORMATION FOR SEQ ID NO:49:

(i) SEQUENCE CHARACTERISTICS:
        (A) LENGTH: 40 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer cMm210f (xi) SEQUENCE DESCRIPTION: SEQ ID NO:49:

TGTAAAACGA CGGCCAGTAC ATCAAATTGT TTTTCACCAG                   40

(2) INFORMATION FOR SEQ ID NO:50:

(i) SEQUENCE CHARACTERISTICS:
        (A) LENGTH: 43 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer cMm210r (xi) SEQUENCE DESCRIPTION: SEQ ID NO:50:

CAGGAAACAG CTATGACCAT ATATTACCTT CCAGTGTGTT TCT               43

(2) INFORMATION FOR SEQ ID NO:51:

```
        (i) SEQUENCE CHARACTERISTICS:
             (A) LENGTH: 38 bases
             (B) TYPE: nucleic acid
             (C) STRANDEDNESS: single
             (D) TOPOLOGY: linear (ii) MOLECULE TYPE: other nucleic acid (ix) FEATURE:
             (A) NAME/KEY: primer cMm220f (xi) SEQUENCE DESCRIPTION: SEQ ID NO:51:

GTAAAACGAC GGCCAGTTTT AATTTCCCTT TATTCAAC                           38

(2) INFORMATION FOR SEQ ID NO:52:

(i) SEQUENCE CHARACTERISTICS:
             (A) LENGTH: 39 bases
             (B) TYPE: nucleic acid
             (C) STRANDEDNESS: single
             (D) TOPOLOGY: linear (ii) MOLECULE TYPE: other nucleic acid (ix) FEATURE:
             (A) NAME/KEY: primer cMm220r (xi) SEQUENCE DESCRIPTION: SEQ ID NO:52:

GGAAACAGCT ATGACCATGG TCAACCAACC TGTCCACAA                          39

(2) INFORMATION FOR SEQ ID NO:53:

(i) SEQUENCE CHARACTERISTICS:
             (A) LENGTH: 37 bases
             (B) TYPE: nucleic acid
             (C) STRANDEDNESS: single
             (D) TOPOLOGY: linear (ii) MOLECULE TYPE: other nucleic acid (ix) FEATURE:
             (A) NAME/KEY: primer cMm240f (xi) SEQUENCE DESCRIPTION: SEQ ID NO:53:

GTAAAACGAC GGCCAGTTCC TGACTCTGAG TAACCCT                            37

(2) INFORMATION FOR SEQ ID NO:54:

(i) SEQUENCE CHARACTERISTICS:
             (A) LENGTH: 39 bases
             (B) TYPE: nucleic acid
             (C) STRANDEDNESS: single
             (D) TOPOLOGY: linear (ii) MOLECULE TYPE: other nucleic acid (ix) FEATURE:
             (A) NAME/KEY: primer cMm240r (xi) SEQUENCE DESCRIPTION: SEQ ID NO:54:

GGAAACAGCT ATGACCATGT GAGCTTTACC TGACTCTTG                          39

(2) INFORMATION FOR SEQ ID NO:55:

(i) SEQUENCE CHARACTERISTICS:
             (A) LENGTH: 37 bases
             (B) TYPE: nucleic acid
             (C) STRANDEDNESS: single
             (D) TOPOLOGY: linear (ii) MOLECULE TYPE: other nucleic acid
```

```
    (ix) FEATURE:
         (A) NAME/KEY: primer cMm260f (xi) SEQUENCE DESCRIPTION: SEQ ID NO:55:

GTAAAACGAC GGCCAGTTCT GTGAAAACAG CTTGATC                                37

(2) INFORMATION FOR SEQ ID NO:56:

(i) SEQUENCE CHARACTERISTICS:
         (A) LENGTH: 39 bases
         (B) TYPE: nucleic acid
         (C) STRANDEDNESS: single
         (D) TOPOLOGY: linear (ii) MOLECULE TYPE: other nucleic acid (ix) FEATURE:
         (A) NAME/KEY: primer cMm260r (xi) SEQUENCE DESCRIPTION: SEQ ID NO:56:

GGAAACAGCT ATGACCATGA GGCATAGCCT ACTGCTAAG                               39

(2) INFORMATION FOR SEQ ID NO:57:

(i) SEQUENCE CHARACTERISTICS:
         (A) LENGTH: 37 bases
         (B) TYPE: nucleic acid
         (C) STRANDEDNESS: single
         (D) TOPOLOGY: linear (ii) MOLECULE TYPE: other nucleic acid (ix) FEATURE:
         (A) NAME/KEY: primer cMm280f (xi) SEQUENCE DESCRIPTION: SEQ ID NO:57:

GTAAAACGAC GGCCAGTACT GGTGGGAGCT GTTATTG                                 37

(2) INFORMATION FOR SEQ ID NO:58:

(i) SEQUENCE CHARACTERISTICS:
         (A) LENGTH: 39 bases
         (B) TYPE: nucleic acid
         (C) STRANDEDNESS: single
         (D) TOPOLOGY: linear (ii) MOLECULE TYPE: other nucleic acid (ix) FEATURE:
         (A) NAME/KEY: primer cMm280r (xi) SEQUENCE DESCRIPTION: SEQ ID NO:58:

GGAAACAGCT ATGACCATGG AGGTAAAACC TTTCAGTCC                               39

(2) INFORMATION FOR SEQ ID NO:59:

(i) SEQUENCE CHARACTERISTICS:
         (A) LENGTH: 38 bases
         (B) TYPE: nucleic acid
         (C) STRANDEDNESS: single
         (D) TOPOLOGY: linear (ii) MOLECULE TYPE: other nucleic acid (ix) FEATURE:
         (A) NAME/KEY: primer TMm100f (xi) SEQUENCE DESCRIPTION: SEQ ID NO:59:

TGTAAAACGA CGGCCAGTCC GCAGAGTGAC CCTTTTTC                                38
```

(2) INFORMATION FOR SEQ ID NO:60:

(i) SEQUENCE CHARACTERISTICS:
        (A) LENGTH: 38 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer TMm100r (xi) SEQUENCE DESCRIPTION: SEQ ID NO:60:

CAGGAAACAG CTATGACCAT GTCTCCCTTC TCGCTGCC                   38

(2) INFORMATION FOR SEQ ID NO:61:

(i) SEQUENCE CHARACTERISTICS:
        (A) LENGTH: 36 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer TMm120f (xi) SEQUENCE DESCRIPTION: SEQ ID NO:61:

TGTAAAACGA CGGCCAGTTG GAAGGTGGAG AGGGTG                     36

(2) INFORMATION FOR SEQ ID NO:62:

(i) SEQUENCE CHARACTERISTICS:
        (A) LENGTH: 39 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer TMm120r (xi) SEQUENCE DESCRIPTION: SEQ ID NO:62:

CAGGAAACAG CTATGACCAT GCCGTTCTTG GTCACAATC                  39

(2) INFORMATION FOR SEQ ID NO:63:

(i) SEQUENCE CHARACTERISTICS:
        (A) LENGTH: 37 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer TMm140f (xi) SEQUENCE DESCRIPTION: SEQ ID NO:63:

TGTAAAACGA CGGCCAGTGA GGATGTTCCC GGTGCTG                    37

(2) INFORMATION FOR SEQ ID NO:64:

(i) SEQUENCE CHARACTERISTICS:
        (A) LENGTH: 40 bases
        (B) TYPE: nucleic acid
        (C) STRANDEDNESS: single
        (D) TOPOLOGY: linear

```
       (ii) MOLECULE TYPE: other nucleic acid (ix) FEATURE:
            (A) NAME/KEY: primer TMm140r (xi) SEQUENCE DESCRIPTION: SEQ ID NO:64:

CAGGAAACAG CTATGACCAT GGTACCCACT CCCCGTTCAC                          40

(2) INFORMATION FOR SEQ ID NO:65:

(i) SEQUENCE CHARACTERISTICS:
            (A) LENGTH: 38 bases
            (B) TYPE: nucleic acid
            (C) STRANDEDNESS: single
            (D) TOPOLOGY: linear (ii) MOLECULE TYPE: other nucleic acid (ix) FEATURE:
            (A) NAME/KEY: primer TMm160f (xi) SEQUENCE DESCRIPTION: SEQ ID NO:65:

TGTAAAACGA CGGCCAGTTC TTGCTGGACT TCGTGACG                            38

(2) INFORMATION FOR SEQ ID NO:66:

(i) SEQUENCE CHARACTERISTICS:
            (A) LENGTH: 39 bases
            (B) TYPE: nucleic acid
            (C) STRANDEDNESS: single
            (D) TOPOLOGY: linear (ii) MOLECULE TYPE: other nucleic acid (ix) FEATURE:
            (A) NAME/KEY: primer TMm160r (xi) SEQUENCE DESCRIPTION: SEQ ID NO:66:

CAGGAAACAG CTATGACCAT CTGTCCCCCT CCATTGAGC                           39

(2) INFORMATION FOR SEQ ID NO:67:

(i) SEQUENCE CHARACTERISTICS:
            (A) LENGTH: 42 bases
            (B) TYPE: nucleic acid
            (C) STRANDEDNESS: single
            (D) TOPOLOGY: linear (ii) MOLECULE TYPE: other nucleic acid (ix) FEATURE:
            (A) NAME/KEY: primer TMm180f (xi) SEQUENCE DESCRIPTION: SEQ ID NO:67:

TGTAAAACGA CGGCCAGTAA ACTCCTTGCA TAAGTATGAA CC                       42

(2) INFORMATION FOR SEQ ID NO:68:

(i) SEQUENCE CHARACTERISTICS:
            (A) LENGTH: 41 bases
            (B) TYPE: nucleic acid
            (C) STRANDEDNESS: single
            (D) TOPOLOGY: linear (ii) MOLECULE TYPE: other nucleic acid (ix) FEATURE:
            (A) NAME/KEY: primer TMm180r (xi) SEQUENCE DESCRIPTION: SEQ ID NO:68:

CAGGAAACAG CTATGACCAT TCCTCATTCT GGTAGGCAGT C                        41
```

(2) INFORMATION FOR SEQ ID NO:69:

(i) SEQUENCE CHARACTERISTICS:
        (A) LENGTH: 36 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer TMm200f (xi) SEQUENCE DESCRIPTION: SEQ ID NO:69:

TGTAAAACGA CGGCCAGTGT GGCTTGTTCC TGGTGC                      36

(2) INFORMATION FOR SEQ ID NO:70:

(i) SEQUENCE CHARACTERISTICS:
        (A) LENGTH: 39 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer TMm200r (xi) SEQUENCE DESCRIPTION: SEQ ID NO:70:

CAGGAAACAG CTATGACCAT TTGGAGAGCT GTTCCGATG                 39

(2) INFORMATION FOR SEQ ID NO:71:

(i) SEQUENCE CHARACTERISTICS:
        (A) LENGTH: 39 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer TMm220f (xi) SEQUENCE DESCRIPTION: SEQ ID NO:71:

TGTAAAACGA CGGCCAGTCC TATGCGGACA ATTCATCTG                 39

(2) INFORMATION FOR SEQ ID NO:72:

(i) SEQUENCE CHARACTERISTICS:
        (A) LENGTH: 38 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer TMm220r (xi) SEQUENCE DESCRIPTION: SEQ ID NO:72:

CAGGAAACAG CTATGACCAT AGGTGGGCTG GCGTTATG                  38

(2) INFORMATION FOR SEQ ID NO:73:

(i) SEQUENCE CHARACTERISTICS:
        (A) LENGTH: 40 bases
        (B) TYPE: nucleic acid
        (C) STRANDEDNESS: single (D) TOPOLOGY: linear (ii) MOLECULE TYPE: other nucleic acid (ix) FEATURE:
         (A) NAME/KEY: primer TMm240f (xi) SEQUENCE DESCRIPTION: SEQ ID NO:73:

TGTAAAACGA CGGCCAGTCA GTATCCCAGT CTCTGGTCTG                             40

(2) INFORMATION FOR SEQ ID NO:74:

(i) SEQUENCE CHARACTERISTICS:
         (A) LENGTH: 42 bases
         (B) TYPE: nucleic acid
         (C) STRANDEDNESS: single
         (D) TOPOLOGY: linear (ii) MOLECULE TYPE: other nucleic acid (ix) FEATURE:
         (A) NAME/KEY: primer TMm240r (xi) SEQUENCE DESCRIPTION: SEQ ID NO:74:

CAGGAAACAG CTATGACCAT GGCTGTCAGA AATGTCTGTG AC                          42

(2) INFORMATION FOR SEQ ID NO:75:

(i) SEQUENCE CHARACTERISTICS:
         (A) LENGTH: 40 bases
         (B) TYPE: nucleic acid
         (C) STRANDEDNESS: single
         (D) TOPOLOGY: linear (ii) MOLECULE TYPE: other nucleic acid (ix) FEATURE:
         (A) NAME/KEY: primer TMm260f (xi) SEQUENCE DESCRIPTION: SEQ ID NO:75:

TGTAAAACGA CGGCCAGTAC ATTACACACC ACTGACGCAC                             40

(2) INFORMATION FOR SEQ ID NO:76:

(i) SEQUENCE CHARACTERISTICS:
         (A) LENGTH: 42 bases
         (B) TYPE: nucleic acid
         (C) STRANDEDNESS: single
         (D) TOPOLOGY: linear (ii) MOLECULE TYPE: other nucleic acid (ix) FEATURE:
         (A) NAME/KEY: primer TMm260r (xi) SEQUENCE DESCRIPTION: SEQ ID NO:76:

CAGGAAACAG CTATGACCAT TATTTTTCCC TTGTCCCAAG AG                          42

(2) INFORMATION FOR SEQ ID NO:77:

(i) SEQUENCE CHARACTERISTICS:
         (A) LENGTH: 38 bases
         (B) TYPE: nucleic acid
         (C) STRANDEDNESS: single
         (D) TOPOLOGY: linear (ii) MOLECULE TYPE: other nucleic acid (ix) FEATURE:
         (A) NAME/KEY: primer bMm100f (xi) SEQUENCE DESCRIPTION: SEQ ID NO:77:

```
TGTAAAACGA CGGCCAGTTT CTCCATGCAA AGAGCAGC                                          38

(2) INFORMATION FOR SEQ ID NO:78:

(i) SEQUENCE CHARACTERISTICS:
           (A) LENGTH: 40 bases
           (B) TYPE: nucleic acid
           (C) STRANDEDNESS: single
           (D) TOPOLOGY: linear (ii) MOLECULE TYPE: other nucleic acid (ix) FEATURE:
           (A) NAME/KEY: primer bMm100r (xi) SEQUENCE DESCRIPTION: SEQ ID NO:78:

CAGGAAACAG CTATGACCAT CAATCACAGC CACACACCTG                                        40

(2) INFORMATION FOR SEQ ID NO:79:

(i) SEQUENCE CHARACTERISTICS:
           (A) LENGTH: 38 bases
           (B) TYPE: nucleic acid
           (C) STRANDEDNESS: single
           (D) TOPOLOGY: linear (ii) MOLECULE TYPE: other nucleic acid (ix) FEATURE:
           (A) NAME/KEY: primer bMm120f (xi) SEQUENCE DESCRIPTION: SEQ ID NO:79:

TGTAAAACGA CGGCCAGTGA CCCTTGTGGC TCATCATC                                          38

(2) INFORMATION FOR SEQ ID NO:80:

(i) SEQUENCE CHARACTERISTICS:
           (A) LENGTH: 40 bases
           (B) TYPE: nucleic acid
           (C) STRANDEDNESS: single
           (D) TOPOLOGY: linear (ii) MOLECULE TYPE: other nucleic acid (ix) FEATURE:
           (A) NAME/KEY: primer bMm120r (xi) SEQUENCE DESCRIPTION: SEQ ID NO:80:

CAGGAAACAG CTATGACCAT TGTCTTCCCC GCCTTTCTAC                                        40

(2) INFORMATION FOR SEQ ID NO:81:

(i) SEQUENCE CHARACTERISTICS:
           (A) LENGTH: 39 bases
           (B) TYPE: nucleic acid
           (C) STRANDEDNESS: single
           (D) TOPOLOGY: linear (ii) MOLECULE TYPE: other nucleic acid (ix) FEATURE:
           (A) NAME/KEY: primer bMm140f (xi) SEQUENCE DESCRIPTION: SEQ ID NO:81:

TGTAAAACGA CGGCCAGTCT TTTCATGTTT AAAGTCAGG                                         39

(2) INFORMATION FOR SEQ ID NO:82:

(i) SEQUENCE CHARACTERISTICS:
           (A) LENGTH: 42 bases
```

```
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer bMm140r (xi) SEQUENCE DESCRIPTION: SEQ ID NO:82:

CAGGAAACAG CTATGACCAT CAAACAAAGT AGTTATAAAC GG                              42

(2) INFORMATION FOR SEQ ID NO:83:

(i) SEQUENCE CHARACTERISTICS:
        (A) LENGTH: 38 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer bMm160f (xi) SEQUENCE DESCRIPTION: SEQ ID NO:83:

TGTAAAACGA CGGCCAGTTT AGAAGACATA CTGGGACC                                   38

(2) INFORMATION FOR SEQ ID NO:84:

(i) SEQUENCE CHARACTERISTICS:
        (A) LENGTH: 40 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer bMm160r (xi) SEQUENCE DESCRIPTION: SEQ ID NO:84:

CAGGAAACAG CTATGACCAT ACCTAAAAAC CAAGAATCAG                                 40

(2) INFORMATION FOR SEQ ID NO:85:

(i) SEQUENCE CHARACTERISTICS:
        (A) LENGTH: 40 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer bMm180f (xi) SEQUENCE DESCRIPTION: SEQ ID NO:85:

TGTAAAACGA CGGCCAGTAT TTCTATGATC TAGGAGATGC                                 40

(2) INFORMATION FOR SEQ ID NO:86:

(i) SEQUENCE CHARACTERISTICS:
        (A) LENGTH: 40 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer bMm180r
```

(xi) SEQUENCE DESCRIPTION: SEQ ID NO:86:

CAGGAAACAG CTATGACCAT TAGTAGCTGT CATTTGGGTC                40

(2) INFORMATION FOR SEQ ID NO:87:

(i) SEQUENCE CHARACTERISTICS:
        (A) LENGTH: 36 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer bMm200f (xi) SEQUENCE DESCRIPTION: SEQ ID NO:87:

TGTAAAACGA CGGCCAGTTT CCTTTCCTCC CCAGGC                    36

(2) INFORMATION FOR SEQ ID NO:88:

(i) SEQUENCE CHARACTERISTICS:
        (A) LENGTH: 45 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer bMm200r (xi) SEQUENCE DESCRIPTION: SEQ ID NO:88:

CAGGAAACAG CTATGACCAT CAAAACACCA ATTTTGTTTA CTTGC          45

(2) INFORMATION FOR SEQ ID NO:89:

(i) SEQUENCE CHARACTERISTICS:
        (A) LENGTH: 40 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer bMm220f (xi) SEQUENCE DESCRIPTION: SEQ ID NO:89:

TGTAAAACGA CGGCCAGTCT TTCAAATGTA GGTTACAGTG                40

(2) INFORMATION FOR SEQ ID NO:90:

(i) SEQUENCE CHARACTERISTICS:
        (A) LENGTH: 40 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer bMm220r (xi) SEQUENCE DESCRIPTION: SEQ ID NO:90:

CAGGAAACAG CTATGACCAT AAAACATAGG AAAGCATCTC                40

(2) INFORMATION FOR SEQ ID NO:91:

(i) SEQUENCE CHARACTERISTICS:
            (A) LENGTH: 38 bases
            (B) TYPE: nucleic acid
            (C) STRANDEDNESS: single
            (D) TOPOLOGY: linear (ii) MOLECULE TYPE: other nucleic acid (ix) FEATURE:
            (A) NAME/KEY: primer bMm240f (xi) SEQUENCE DESCRIPTION: SEQ ID NO:91:

TGTAAAACGA CGGCCAGTGC CTTTGGAATA TTTTAGAT                                    38

(2) INFORMATION FOR SEQ ID NO:92:

(i) SEQUENCE CHARACTERISTICS:
            (A) LENGTH: 41 bases
            (B) TYPE: nucleic acid
            (C) STRANDEDNESS: single
            (D) TOPOLOGY: linear (ii) MOLECULE TYPE: other nucleic acid (ix) FEATURE:
            (A) NAME/KEY: primer bMm240r (xi) SEQUENCE DESCRIPTION: SEQ ID NO:92:

CAGGAAACAG CTATGACCAT GTAAAAATAC CCTGACAAAA C                                41

(2) INFORMATION FOR SEQ ID NO:93:

(i) SEQUENCE CHARACTERISTICS:
            (A) LENGTH: 40 bases
            (B) TYPE: nucleic acid
            (C) STRANDEDNESS: single
            (D) TOPOLOGY: linear (ii) MOLECULE TYPE: other nucleic acid (ix) FEATURE:
            (A) NAME/KEY: primer bMm260f (xi) SEQUENCE DESCRIPTION: SEQ ID NO:93:

TGTAAAACGA CGGCCAGTTC TTATCTTTCA AATAGGTCAG                                  40

(2) INFORMATION FOR SEQ ID NO:94:

(i) SEQUENCE CHARACTERISTICS:
            (A) LENGTH: 40 bases
            (B) TYPE: nucleic acid
            (C) STRANDEDNESS: single
            (D) TOPOLOGY: linear (ii) MOLECULE TYPE: other nucleic acid (ix) FEATURE:
            (A) NAME/KEY: primer bMm260r (xi) SEQUENCE DESCRIPTION: SEQ ID NO:94:

CAGGAAACAG CTATGACCAT ATAGCGTTGA TAGTGATCAG                                  40

(2) INFORMATION FOR SEQ ID NO:95:

(i) SEQUENCE CHARACTERISTICS:
            (A) LENGTH: 38 bases
            (B) TYPE: nucleic acid
            (C) STRANDEDNESS: single
            (D) TOPOLOGY: linear (ii) MOLECULE TYPE: other nucleic acid (ix) FEATURE:
              (A) NAME/KEY: primer bMm280f (xi) SEQUENCE DESCRIPTION: SEQ ID NO:95:

TGTAAAACGA CGGCCAGTAT TACCATTGCT GTAGTGGC                                      38

(2) INFORMATION FOR SEQ ID NO:96:

(i) SEQUENCE CHARACTERISTICS:
              (A) LENGTH: 40 bases
              (B) TYPE: nucleic acid
              (C) STRANDEDNESS: single
              (D) TOPOLOGY: linear (ii) MOLECULE TYPE: other nucleic acid (ix) FEATURE:
              (A) NAME/KEY: primer bMm280r (xi) SEQUENCE DESCRIPTION: SEQ ID NO:96:

CAGGAAACAG CTATGACCAT TGTTTCAATC AGGTTGCTTC                                    40

(2) INFORMATION FOR SEQ ID NO:97:

(i) SEQUENCE CHARACTERISTICS:
              (A) LENGTH: 38 bases
              (B) TYPE: nucleic acid
              (C) STRANDEDNESS: single
              (D) TOPOLOGY: linear (ii) MOLECULE TYPE: other nucleic acid (ix) FEATURE:
              (A) NAME/KEY: primer SryMm100f (xi) SEQUENCE DESCRIPTION: SEQ ID NO:97:

TGTAAAACGA CGGCCAGTCA AGTTTTGGGA CTGGTGAC                                      38

(2) INFORMATION FOR SEQ ID NO:98:

(i) SEQUENCE CHARACTERISTICS:
              (A) LENGTH: 40 bases
              (B) TYPE: nucleic acid
              (C) STRANDEDNESS: single
              (D) TOPOLOGY: linear (ii) MOLECULE TYPE: other nucleic acid (ix) FEATURE:
              (A) NAME/KEY: primer SryMm100r (xi) SEQUENCE DESCRIPTION: SEQ ID NO:98:

CAGGAAACAG CTATGACCAT GGCTTCTGTA AGGCTTTTCC                                    40

(2) INFORMATION FOR SEQ ID NO:99:

(i) SEQUENCE CHARACTERISTICS:
              (A) LENGTH: 38 bases
              (B) TYPE: nucleic acid
              (C) STRANDEDNESS: single
              (D) TOPOLOGY: linear (ii) MOLECULE TYPE: other nucleic acid (ix) FEATURE:
              (A) NAME/KEY: primer SryMm120f (xi) SEQUENCE DESCRIPTION: SEQ ID NO:99:

TGTAAAACGA CGGCCAGTCA AGTTGGCCCA GCAGAATC                                      38

(2) INFORMATION FOR SEQ ID NO:100:

(i) SEQUENCE CHARACTERISTICS:
        (A) LENGTH: 40
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer Sry100Mm120r (xi) SEQUENCE DESCRIPTION: SEQ ID NO:100:

CAGGAAACAG CTATGACCAT GTTGAGGCAA CTGCAGGCTG                            40

(2) INFORMATION FOR SEQ ID NO:101:

(i) SEQUENCE CHARACTERISTICS:
        (A) LENGTH: 42 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer SryMm140f (xi) SEQUENCE DESCRIPTION: SEQ ID NO:101:

TGTAAAACGA CGGCCAGTGA GGGCTAAAGT GTCACAGAGG AG                         42

(2) INFORMATION FOR SEQ ID NO:102:

(i) SEQUENCE CHARACTERISTICS:
        (A) LENGTH: 43 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer SryMm140r (xi) SEQUENCE DESCRIPTION: SEQ ID NO:102:

CAGGAAACAG CTATGACCAT CATAGAACTG CTGTTGCTGC TGG                        43

(2) INFORMATION FOR SEQ ID NO:103:

(i) SEQUENCE CHARACTERISTICS:
        (A) LENGTH: 40 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer SryMm160f (xi) SEQUENCE DESCRIPTION: SEQ ID NO:103:

TGTAAAACGA CGGCCAGTCA GCAGCAGCAG TTCCATAACC                            40

(2) INFORMATION FOR SEQ ID NO:104:

(i) SEQUENCE CHARACTERISTICS:
        (A) LENGTH: 39 bases
        (B) TYPE: nucleic acid
        (C) STRANDEDNESS: single
        (D) TOPOLOGY: linear (ii) MOLECULE TYPE: other nucleic acid (ix) FEATURE:
             (A) NAME/KEY: primer SryMm160r (xi) SEQUENCE DESCRIPTION: SEQ ID NO:104:

CAGGAAACAG CTATGACCAT GCTCCTGGTG GTGGTGGTG                                    39

(2) INFORMATION FOR SEQ ID NO:105:

(i) SEQUENCE CHARACTERISTICS:
             (A) LENGTH: 36 bases
             (B) TYPE: nucleic acid
             (C) STRANDEDNESS: single
             (D) TOPOLOGY: linear (ii) MOLECULE TYPE: other nucleic acid (ix) FEATURE:
             (A) NAME/KEY: primer SryMm180f (xi) SEQUENCE DESCRIPTION: SEQ ID NO:105:

TGTAAAACGA CGGCCAGTCA GCAGAAGCAG CAGTTT                                       36

(2) INFORMATION FOR SEQ ID NO:106:

(i) SEQUENCE CHARACTERISTICS:
             (A) LENGTH: 38 bases
             (B) TYPE: nucleic acid
             (C) STRANDEDNESS: single
             (D) TOPOLOGY: linear (ii) MOLECULE TYPE: other nucleic acid (ix) FEATURE:
             (A) NAME/KEY: primer SryMm180r (xi) SEQUENCE DESCRIPTION: SEQ ID NO:106:

CAGGAAACAG CTATGACCAT TTGGTGGTGG TGGTGGTC                                     38

(2) INFORMATION FOR SEQ ID NO:107:

(i) SEQUENCE CHARACTERISTICS:
             (A) LENGTH: 36 bases
             (B) TYPE: nucleic acid
             (C) STRANDEDNESS: single
             (D) TOPOLOGY: linear (ii) MOLECULE TYPE: other nucleic acid (ix) FEATURE:
             (A) NAME/KEY: primer SryMm200f (xi) SEQUENCE DESCRIPTION: SEQ ID NO:107:

TGTAAAACGA CGGCCAGTAC CACCACCACC AGGAGC                                       36

(2) INFORMATION FOR SEQ ID NO:108:

(i) SEQUENCE CHARACTERISTICS:
             (A) LENGTH: 38 bases
             (B) TYPE: nucleic acid
             (C) STRANDEDNESS: single
             (D) TOPOLOGY: linear (ii) MOLECULE TYPE: other nucleic acid (ix) FEATURE:
             (A) NAME/KEY: primer SryMm200r (xi) SEQUENCE DESCRIPTION: SEQ ID NO:108:

CAGGAAACAG CTATGACCAT TGATGCTGCT GCTGCTGG                                     38

(2) INFORMATION FOR SEQ ID NO:109:

(i) SEQUENCE CHARACTERISTICS:
        (A) LENGTH: 34 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer SryMm220f (xi) SEQUENCE DESCRIPTION: SEQ ID NO:109:

TGTAAAACGA CGGCCAGTCA CCACCACCAC CAAC                          34

(2) INFORMATION FOR SEQ ID NO:110:

(i) SEQUENCE CHARACTERISTICS:
        (A) LENGTH: 36 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer SryMm220r (xi) SEQUENCE DESCRIPTION: SEQ ID NO:110:

CAGGAAACAG CTATGACCAT GTTGCTGCTG GGGGTG                        36

(2) INFORMATION FOR SEQ ID NO:111:

(i) SEQUENCE CHARACTERISTICS:
        (A) LENGTH: 38 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer SryMm240f (xi) SEQUENCE DESCRIPTION: SEQ ID NO:111:

TGTAAAACGA CGGCCAGTCA TCAGTTCCAT GACCACCC                    38

(2) INFORMATION FOR SEQ ID NO:112:

(i) SEQUENCE CHARACTERISTICS:
        (A) LENGTH: 40 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer SryMm240r (xi) SEQUENCE DESCRIPTION: SEQ ID NO:112:

CAGGAAACAG CTATGACCAT GGTCATGGAA CTGCTGTTGC                40

(2) INFORMATION FOR SEQ ID NO:113:

(i) SEQUENCE CHARACTERISTICS:
        (A) LENGTH: 38 bases
        (B) TYPE: nucleic acid
        (C) STRANDEDNESS: single (D) TOPOLOGY: linear (ii) MOLECULE TYPE: other nucleic acid (ix) FEATURE:
        (A) NAME/KEY: primer SryMm260f (xi) SEQUENCE DESCRIPTION: SEQ ID NO:113:

TGTAAAACGA CGGCCAGTGA AGCAGCAGTT CCATGACC                                 38

(2) INFORMATION FOR SEQ ID NO:114:

(i) SEQUENCE CHARACTERISTICS:
        (A) LENGTH: 40 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer SryMm260r (xi) SEQUENCE DESCRIPTION: SEQ ID NO:114:

CAGGAAACAG CTATGACCAT CATAGCAAGG GGGAGTGTTG                               40

(2) INFORMATION FOR SEQ ID NO:115:

(i) SEQUENCE CHARACTERISTICS:
        (A) LENGTH: 38 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer MgfMm100f (xi) SEQUENCE DESCRIPTION: SEQ ID NO:115:

TGTAAAACGA CGGCCAGTCT TCATTTGCTG TCTGTCAC                                 38

(2) INFORMATION FOR SEQ ID NO:116:

(i) SEQUENCE CHARACTERISTICS:
        (A) LENGTH: 43 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer MgfMm100r (xi) SEQUENCE DESCRIPTION: SEQ ID NO:116:

CAGGAAACAG CTATGACCAT TTGTGTCTTC TTCATAAGGA AAG                           43

(2) INFORMATION FOR SEQ ID NO:117:

(i) SEQUENCE CHARACTERISTICS:
        (A) LENGTH: 38 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer MgfMm120f (xi) SEQUENCE DESCRIPTION: SEQ ID NO:117:

TGTAAAACGA CGGCCAGTAC TTGGATTATC ACTTGCAT                    38

(2) INFORMATION FOR SEQ ID NO:118:

(i) SEQUENCE CHARACTERISTICS:
        (A) LENGTH: 43 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer MgfMm120r (xi) SEQUENCE DESCRIPTION: SEQ ID NO:118:

CAGGAAACAG CTATGACCAT CAGTTTTGTA ATGTCTTTTA CAT              43

(2) INFORMATION FOR SEQ ID NO:119:

(i) SEQUENCE CHARACTERISTICS:
        (A) LENGTH: 40 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer MgfMm140f (xi) SEQUENCE DESCRIPTION: SEQ ID NO:119:

TGTAAAACGA CGGCCAGTCC TAGTCATTGT TGGCTACGAG                  40

(2) INFORMATION FOR SEQ ID NO:120:

(i) SEQUENCE CHARACTERISTICS:
        (A) LENGTH: 39 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer MgfMm140r (xi) SEQUENCE DESCRIPTION: SEQ ID NO:120:

CAGGAAACAG CTATGACCAT CTTCGGTGCG TTTTCTTCC                   39

(2) INFORMATION FOR SEQ ID NO:121:

(i) SEQUENCE CHARACTERISTICS:
        (A) LENGTH: 41 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer MgfMm160f (xi) SEQUENCE DESCRIPTION: SEQ ID NO:121:

TGTAAAACGA CGGCCAGTAA TATAAAGAA TCTCCGAAGA G                 41

(2) INFORMATION FOR SEQ ID NO:122:

(i) SEQUENCE CHARACTERISTICS:
        (A) LENGTH: 38 bases

```
          (B) TYPE: nucleic acid
          (C) STRANDEDNESS: single
          (D) TOPOLOGY: linear (ii) MOLECULE TYPE: other nucleic acid (ix) FEATURE:
          (A) NAME/KEY: primer MgfMm160r (xi) SEQUENCE DESCRIPTION: SEQ ID NO:122:

CAGGAAACAG CTATGACCAT CTTTCTCGGG ACCTAATG                                 38

(2) INFORMATION FOR SEQ ID NO:123:

(i) SEQUENCE CHARACTERISTICS:
          (A) LENGTH: 36 bases
          (B) TYPE: nucleic acid
          (C) STRANDEDNESS: single
          (D) TOPOLOGY: linear (ii) MOLECULE TYPE: other nucleic acid (ix) FEATURE:
          (A) NAME/KEY: primer MgfMm180f (xi) SEQUENCE DESCRIPTION: SEQ ID NO:123:

TGTAAAACGA CGGCCAGTGG AAAGCCGCAA AGGCCC                                   36

(2) INFORMATION FOR SEQ ID NO:124:

(i) SEQUENCE CHARACTERISTICS:
          (A) LENGTH: 44 bases
          (B) TYPE: nucleic acid
          (C) STRANDEDNESS: single
          (D) TOPOLOGY: linear (ii) MOLECULE TYPE: other nucleic acid (ix) FEATURE:
          (A) NAME/KEY: primer MgfMm180r (xi) SEQUENCE DESCRIPTION: SEQ ID NO:124:

CAGGAAACAG CTATGACCAT CTTCCAGTAT AAGGCTCCAA AAGC                          44

(2) INFORMATION FOR SEQ ID NO:125:

(i) SEQUENCE CHARACTERISTICS:
          (A) LENGTH: 36 bases
          (B) TYPE: nucleic acid
          (C) STRANDEDNESS: single
          (D) TOPOLOGY: linear (ii) MOLECULE TYPE: other nucleic acid (ix) FEATURE:
          (A) NAME/KEY: primer cKitMm100f (xi) SEQUENCE DESCRIPTION: SEQ ID NO:125:

TGTAAAACGA CGGCCAGTCC ACGTCTCAGC CATCTG                                   36

(2) INFORMATION FOR SEQ ID NO:126:

(i) SEQUENCE CHARACTERISTICS:
          (A) LENGTH: 46 bases
          (B) TYPE: nucleic acid
          (C) STRANDEDNESS: single
          (D) TOPOLOGY: linear (ii) MOLECULE TYPE: other nucleic acid (ix) FEATURE:
          (A) NAME/KEY: primer cKitMm100r
```

(xi) SEQUENCE DESCRIPTION: SEQ ID NO:126:

CAGGAAACAG CTATGACCAT CTCTAACAAA CACGTAAATA GAACTC                46

(2) INFORMATION FOR SEQ ID NO:127:

(i) SEQUENCE CHARACTERISTICS:
        (A) LENGTH: 38 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer cKitMm120f (xi) SEQUENCE DESCRIPTION: SEQ ID NO:127:

TGTAAAACGA CGGCCAGTAT CCTGCCAAAC TTTTCCTG                          38

(2) INFORMATION FOR SEQ ID NO:128:

(i) SEQUENCE CHARACTERISTICS:
        (A) LENGTH: 40 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer cKitMm120r (xi) SEQUENCE DESCRIPTION: SEQ ID NO:128:

CAGGAAACAG CTATGACCAT TGAGGGAATA ATTGGACACC                        40

(2) INFORMATION FOR SEQ ID NO:129:

(i) SEQUENCE CHARACTERISTICS:
        (A) LENGTH: 38 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer cKitMm140f (xi) SEQUENCE DESCRIPTION: SEQ ID NO:129:

TGTAAAACGA CGGCCAGTAA GAAGACAGCG ACGCGCTG                          38

(2) INFORMATION FOR SEQ ID NO:130:

(i) SEQUENCE CHARACTERISTICS:
        (A) LENGTH: 40 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer cKitMm140r (xi) SEQUENCE DESCRIPTION: SEQ ID NO:130:

CAGGAAACAG CTATGACCAT CTTCCCGCAC TTTGAGGGTG                        40

(2) INFORMATION FOR SEQ ID NO:131:

(i) SEQUENCE CHARACTERISTICS:
    (A) LENGTH: 36 bases
    (B) TYPE: nucleic acid
    (C) STRANDEDNESS: single
    (D) TOPOLOGY: linear (ii) MOLECULE TYPE: other nucleic acid (ix) FEATURE:
    (A) NAME/KEY: primer cKitMm160f (xi) SEQUENCE DESCRIPTION: SEQ ID NO:131:

TGTAAAACGA CGGCCAGTCC ATCAAGGCTA TCCCTG                36

(2) INFORMATION FOR SEQ ID NO:132:

(i) SEQUENCE CHARACTERISTICS:
       (A) LENGTH: 40 bases
       (B) TYPE: nucleic acid
       (C) STRANDEDNESS: single
       (D) TOPOLOGY: linear (ii) MOLECULE TYPE: other nucleic acid (ix) FEATURE:
       (A) NAME/KEY: primer cKitMm160r (xi) SEQUENCE DESCRIPTION: SEQ ID NO:132:

CAGGAAACAG CTATGACCAT CTGAGGGTTC ATCTTTAGCC             40

(2) INFORMATION FOR SEQ ID NO:133:

(i) SEQUENCE CHARACTERISTICS:
       (A) LENGTH: 36 bases
       (B) TYPE: nucleic acid
       (C) STRANDEDNESS: single
       (D) TOPOLOGY: linear (ii) MOLECULE TYPE: other nucleic acid (ix) FEATURE:
       (A) NAME/KEY: primer cKitMm180f (xi) SEQUENCE DESCRIPTION: SEQ ID NO:133:

TGTAAAACGA CGGCCAGTCC TCAGCACATA GCCCAG                 36

(2) INFORMATION FOR SEQ ID NO:134:

(i) SEQUENCE CHARACTERISTICS:
       (A) LENGTH: 45 bases
       (B) TYPE: nucleic acid
       (C) STRANDEDNESS: single
       (D) TOPOLOGY: linear (ii) MOLECULE TYPE: other nucleic acid (ix) FEATURE:
       (A) NAME/KEY: primer cKitMm180r (xi) SEQUENCE DESCRIPTION: SEQ ID NO:134:

CAGGAAACAG CTATGACCAT CTACTACTTT CAAGGTTGTT GTGAC       45

(2) INFORMATION FOR SEQ ID NO:135:

(i) SEQUENCE CHARACTERISTICS:
       (A) LENGTH: 38 bases
       (B) TYPE: nucleic acid
       (C) STRANDEDNESS: single
       (D) TOPOLOGY: linear (ii) MOLECULE TYPE: other nucleic acid (ix) FEATURE:
            (A) NAME/KEY: primer cKitMm200f (xi) SEQUENCE DESCRIPTION: SEQ ID NO:135:

TGTAAAACGA CGGCCAGTAA AAAGGATTCA TCAACATC                                    38

(2) INFORMATION FOR SEQ ID NO:136:

(i) SEQUENCE CHARACTERISTICS:
            (A) LENGTH: 40 bases
            (B) TYPE: nucleic acid
            (C) STRANDEDNESS: single
            (D) TOPOLOGY: linear (ii) MOLECULE TYPE: other nucleic acid (ix) FEATURE:
            (A) NAME/KEY: primer cKitMm200r (xi) SEQUENCE DESCRIPTION: SEQ ID NO:136:

CAGGAAACAG CTATGACCAT CTGATGTTGC TTTTGTTATC                                  40

(2) INFORMATION FOR SEQ ID NO:137:

(i) SEQUENCE CHARACTERISTICS:
            (A) LENGTH: 38 bases
            (B) TYPE: nucleic acid
            (C) STRANDEDNESS: single
            (D) TOPOLOGY: linear (ii) MOLECULE TYPE: other nucleic acid (ix) FEATURE:
            (A) NAME/KEY: primer cKitMm220f (xi) SEQUENCE DESCRIPTION: SEQ ID NO:137:

TGTAAAACGA CGGCCAGTGT GTACCACTCC TGTCTCAC                                    38

(2) INFORMATION FOR SEQ ID NO:138:

(i) SEQUENCE CHARACTERISTICS:
            (A) LENGTH: 43 bases
            (B) TYPE: nucleic acid
            (C) STRANDEDNESS: single
            (D) TOPOLOGY: linear (ii) MOLECULE TYPE: other nucleic acid (ix) FEATURE:
            (A) NAME/KEY: primer cKitMm220r (xi) SEQUENCE DESCRIPTION: SEQ ID NO:138:

CAGGAAACAG CTATGACCAT CTTTAAATGC AAAGTTAAAG AAG                              43

(2) INFORMATION FOR SEQ ID NO:139:

(i) SEQUENCE CHARACTERISTICS:
            (A) LENGTH: 42 bases
            (B) TYPE: nucleic acid
            (C) STRANDEDNESS: single
            (D) TOPOLOGY: linear (ii) MOLECULE TYPE: other nucleic acid (ix) FEATURE:
            (A) NAME/KEY: primer cKitMm240f (xi) SEQUENCE DESCRIPTION: SEQ ID NO:139:

TGTAAAACGA CGGCCAGTAA ACCCATGTAT GAAGTACAAT GG                               42

(2) INFORMATION FOR SEQ ID NO:140:

(i) SEQUENCE CHARACTERISTICS:
        (A) LENGTH: 37 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer cKitMm240r (xi) SEQUENCE DESCRIPTION: SEQ ID NO:140:

CAGGAAACAG CTATGACCAT CGAAGGCACC AGCTCCC                            37

(2) INFORMATION FOR SEQ ID NO:141:

(i) SEQUENCE CHARACTERISTICS:
        (A) LENGTH: 37 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer cKitMm260f (xi) SEQUENCE DESCRIPTION: SEQ ID NO:141:

TGTAAAACGA CGGCCAGTGG CCCACCCTGG TCATTAC                            37

(2) INFORMATION FOR SEQ ID NO:142:

(i) SEQUENCE CHARACTERISTICS:
        (A) LENGTH: 40 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer cKitMm260r (xi) SEQUENCE DESCRIPTION: SEQ ID NO:142:

CAGGAAACAG CTATGACCAT CAGGAAGGCT CCGTTGAGTG                        40

(2) INFORMATION FOR SEQ ID NO:143:

(i) SEQUENCE CHARACTERISTICS:
        (A) LENGTH: 43 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer cKitMm280f (xi) SEQUENCE DESCRIPTION: SEQ ID NO:143:

TGTAAAACGA CGGCCAGTAC TCGTACATAG AAAGAGACGT GAC                  43

(2) INFORMATION FOR SEQ ID NO:144:

(i) SEQUENCE CHARACTERISTICS:
        (A) LENGTH: 39 bases
        (B) TYPE: nucleic acid
        (C) STRANDEDNESS: single
        (D) TOPOLOGY: linear (ii) MOLECULE TYPE: other nucleic acid (ix) FEATURE:
    (A) NAME/KEY: primer cKitMm280r (xi) SEQUENCE DESCRIPTION: SEQ ID NO:144:

CAGGAAACAG CTATGACCAT ATTCTTGGAG GCGAGGAAC     39

(2) INFORMATION FOR SEQ ID NO:145:

(i) SEQUENCE CHARACTERISTICS:
        (A) LENGTH: 38 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer cKitMm300f (xi) SEQUENCE DESCRIPTION: SEQ ID NO:145:

TGTAAAACGA CGGCCAGTTG TATTCACAGA GATTTGGC     38

(2) INFORMATION FOR SEQ ID NO:146:

(i) SEQUENCE CHARACTERISTICS:
        (A) LENGTH: 40 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer cKitMm300r (xi) SEQUENCE DESCRIPTION: SEQ ID NO:146:

CAGGAAACAG CTATGACCAT ATTTCCTTTG ACCACGTAAT     40

(2) INFORMATION FOR SEQ ID NO:147:

(i) SEQUENCE CHARACTERISTICS:
        (A) LENGTH: 41 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer cKitMm320f (xi) SEQUENCE DESCRIPTION: SEQ ID NO:147:

TGTAAAACGA CGGCCAGTAT TTACTCCAAC TTGGCAAACT G     41

(2) INFORMATION FOR SEQ ID NO:148:

(i) SEQUENCE CHARACTERISTICS:
        (A) LENGTH: 41 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer cKitMm320r (xi) SEQUENCE DESCRIPTION: SEQ ID NO:148:

CAGGAAACAG CTATGACCAT CGCTACCCTG GAATAGGATG C     41

(2) INFORMATION FOR SEQ ID NO:149:

(i) SEQUENCE CHARACTERISTICS:
        (A) LENGTH: 38 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer Pax6Mm121f (xi) SEQUENCE DESCRIPTION: SEQ ID NO:149:

TGTAAAACGA CGGCCAGTGT CACAGCGGAG TGAATCAG                           38

(2) INFORMATION FOR SEQ ID NO:150:

(i) SEQUENCE CHARACTERISTICS:
        (A) LENGTH: 40 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer Pax6Mm121r (xi) SEQUENCE DESCRIPTION: SEQ ID NO:150:

CAGGAAACAG CTATGACCAT TGCAGAATTC GGGAAATGTC                       40

(2) INFORMATION FOR SEQ ID NO:151:

(i) SEQUENCE CHARACTERISTICS:
        (A) LENGTH: 38 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer Pax6Mm161f (xi) SEQUENCE DESCRIPTION: SEQ ID NO:151:

TGTAAAACGA CGGCCAGTGT ATCCAACGGT TGTGTGAG                           38

(2) INFORMATION FOR SEQ ID NO:152:

(i) SEQUENCE CHARACTERISTICS:
        (A) LENGTH: 40 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer Pax6Mm161r (xi) SEQUENCE DESCRIPTION: SEQ ID NO:152:

CAGGAAACAG CTATGACCAT ACTGGGTATG TTATCGTTGG                       40

(2) INFORMATION FOR SEQ ID NO:153:

(i) SEQUENCE CHARACTERISTICS:
        (A) LENGTH: 43 bases
        (B) TYPE: nucleic acid
        (C) STRANDEDNESS: single (D) TOPOLOGY: linear (ii) MOLECULE TYPE: other nucleic acid (ix) FEATURE:
         (A) NAME/KEY: primer Pax6Mm180f (xi) SEQUENCE DESCRIPTION: SEQ ID NO:153:

TGTAAAACGA CGGCCAGTGT GTCATCAATA AACAGAGTTC TTC                43

(2) INFORMATION FOR SEQ ID NO:154:

(i) SEQUENCE CHARACTERISTICS:
        (A) LENGTH: 38 bases
        (B) TYPE: nucleic acid
        (C) STRANDEDNESS: single
        (D) TOPOLOGY: linear (ii) MOLECULE TYPE: other nucleic acid (ix) FEATURE:
         (A) NAME/KEY: primer Pax6Mm180r (xi) SEQUENCE DESCRIPTION: SEQ ID NO:154:

CAGGAAACAG CTATGACCAT CGTGGGTTGC CCTGGTAC                      38

(2) INFORMATION FOR SEQ ID NO:155:

(i) SEQUENCE CHARACTERISTICS:
        (A) LENGTH: 36 bases
        (B) TYPE: nucleic acid
        (C) STRANDEDNESS: single
        (D) TOPOLOGY: linear (ii) MOLECULE TYPE: other nucleic acid (ix) FEATURE:
         (A) NAME/KEY: primer Pax6Mm200f (xi) SEQUENCE DESCRIPTION: SEQ ID NO:155:

TGTAAAACGA CGGCCAGTAT GGCTGCCAGC AACAGG                        36

(2) INFORMATION FOR SEQ ID NO:156:

(i) SEQUENCE CHARACTERISTICS:
        (A) LENGTH: 43 bases
        (B) TYPE: nucleic acid
        (C) STRANDEDNESS: single
        (D) TOPOLOGY: linear (ii) MOLECULE TYPE: other nucleic acid (ix) FEATURE:
         (A) NAME/KEY: primer Pax6Mm200r (xi) SEQUENCE DESCRIPTION: SEQ ID NO:156:

CAGGAAACAG CTATGACCAT CTTTCTCCAG AGCCTCAATC TGC                43

(2) INFORMATION FOR SEQ ID NO:157:

(i) SEQUENCE CHARACTERISTICS:
        (A) LENGTH: 41 bases
        (B) TYPE: nucleic acid
        (C) STRANDEDNESS: single
        (D) TOPOLOGY: linear (ii) MOLECULE TYPE: other nucleic acid (ix) FEATURE:
         (A) NAME/KEY: primer Pax6Mm220f (xi) SEQUENCE DESCRIPTION: SEQ ID NO:157:

TGTAAAACGA CGGCCAGTGT ATGGTTTTCT AATCGAAGGG C                       41

(2) INFORMATION FOR SEQ ID NO:158:

(i) SEQUENCE CHARACTERISTICS:
        (A) LENGTH: 38 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer Pax6Mm220r (xi) SEQUENCE DESCRIPTION: SEQ ID NO:158:

CAGGAAACAG CTATGACCAT CAGGTGTGGT GGGCTGTG                           38

(2) INFORMATION FOR SEQ ID NO:159:

(i) SEQUENCE CHARACTERISTICS:
        (A) LENGTH: 36 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer Pax6Mm240f (xi) SEQUENCE DESCRIPTION: SEQ ID NO:159:

TGTAAAACGA CGGCCAGTCC CCCAGTCCCC AGTCAG                             36

(2) INFORMATION FOR SEQ ID NO:160:

(i) SEQUENCE CHARACTERISTICS:
        (A) LENGTH: 40 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer Pax6Mm240r (xi) SEQUENCE DESCRIPTION: SEQ ID NO:160:

CAGGAAACAG CTATGACCAT CTGTTGAAGT GGTCCCCGAG                         40

(2) INFORMATION FOR SEQ ID NO:161:

(i) SEQUENCE CHARACTERISTICS:
        (A) LENGTH: 38 bases
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer Pax6Mm260f (xi) SEQUENCE DESCRIPTION: SEQ ID NO:161:

TGTAAAACGA CGGCCAGTGA CTCATTTCAC CTGGAGTG                           38

(2) INFORMATION FOR SEQ ID NO:162:

(i) SEQUENCE CHARACTERISTICS:
        (A) LENGTH: 40 bases

-continued

```
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer Pax6Mm260r (xi) SEQUENCE DESCRIPTION: SEQ ID NO:162:

CAGGAAACAG CTATGACCAT AAGGTCCTTG GTTCTAGTCC                              40
```